(12) United States Patent
Dengl et al.

(10) Patent No.: US 9,862,763 B2
(45) Date of Patent: Jan. 9, 2018

(54) HUMANIZED ANTI-TAU(PS422) ANTIBODIES AND METHODS OF USE

(71) Applicant: Hoffmann-La Roche Inc., Little Falls, NJ (US)

(72) Inventors: Stefan Dengl, Munich (DE); Thomas Emrich, Iffeldorf (DE); Guy Georges, Habach (DE); Ulrich Goepfert, Penzberg (DE); Fiona Grueninger, Arlesheim (CH); Adrian Hugenmatter, Zurich (CH); Anton Jochner, Oberammergau (DE); Hubert Kettenberger, Munich (DE); Joerg Moelleken, Munich (DE); Ekkehard Moessner, Kreuzlingen (CH); Olaf Mundigl, Weilheim (DE); Jens Niewoehner, Munich (DE); Tilman Schlothauer, Penzberg (DE); Michael Molhoj, Munich (DE); Kevin Brady, Basel (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 15/189,711

(22) Filed: Jun. 22, 2016

(65) Prior Publication Data

US 2016/0376352 A1    Dec. 29, 2016

(30) Foreign Application Priority Data

Jun. 24, 2015  (EP) .................................... 15173511

(51) Int. Cl.
*C07K 16/18* (2006.01)
*C07K 14/47* (2006.01)
*A61K 39/395* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/31* (2013.01); *C07K 2317/34* (2013.01); *C07K 2317/92* (2013.01)

(58) Field of Classification Search
None
See application file for complete search history.

(56) References Cited

FOREIGN PATENT DOCUMENTS

| WO | WO 2010142423 A2 | 12/2010 |
| WO | WO 2015091656 A1 | 6/2015 |
| WO | WO 2015101586 A1 | 7/2015 |

OTHER PUBLICATIONS

European Search Report for EP 15173511.5, dated Jan. 19, 2016.
Internationalsearch Report for PCT/EP2016/064465, dated Aug. 22, 2016.
Written Opinion of the International Searching Authority for PCT/EP2016/064465, dated Aug. 22, 2016.

*Primary Examiner* — Adam M Weidner
*Assistant Examiner* — Aurora M Fontainhas
(74) *Attorney, Agent, or Firm* — Bryan Cave LLP

(57) ABSTRACT

The invention provides humanized anti-human Tau(pS422) antibodies and methods of using the same.

13 Claims, 9 Drawing Sheets

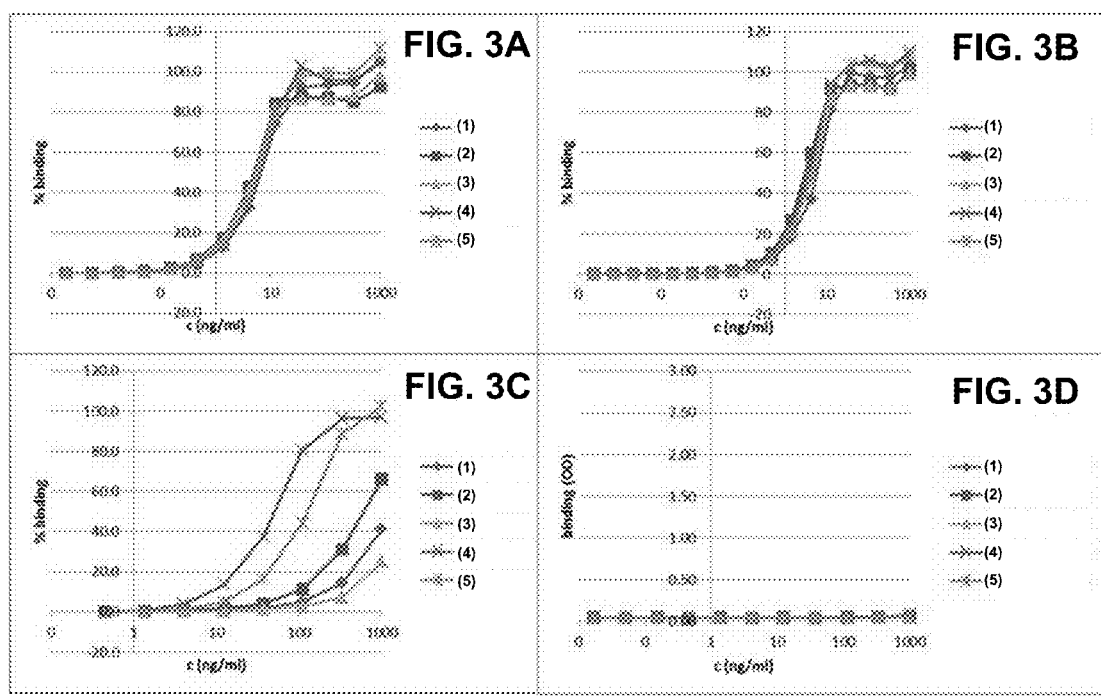

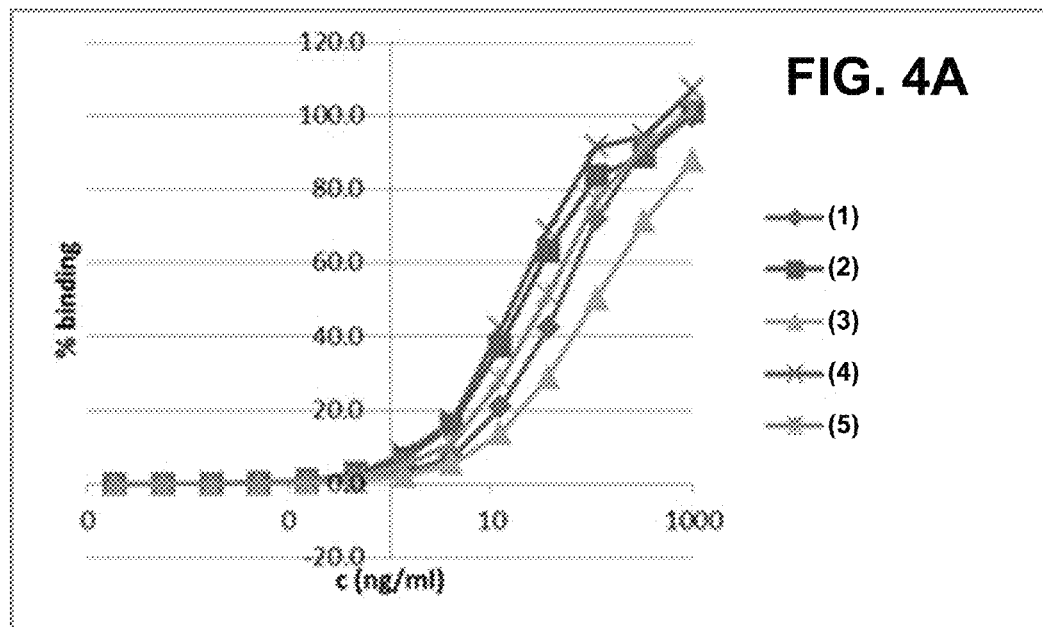
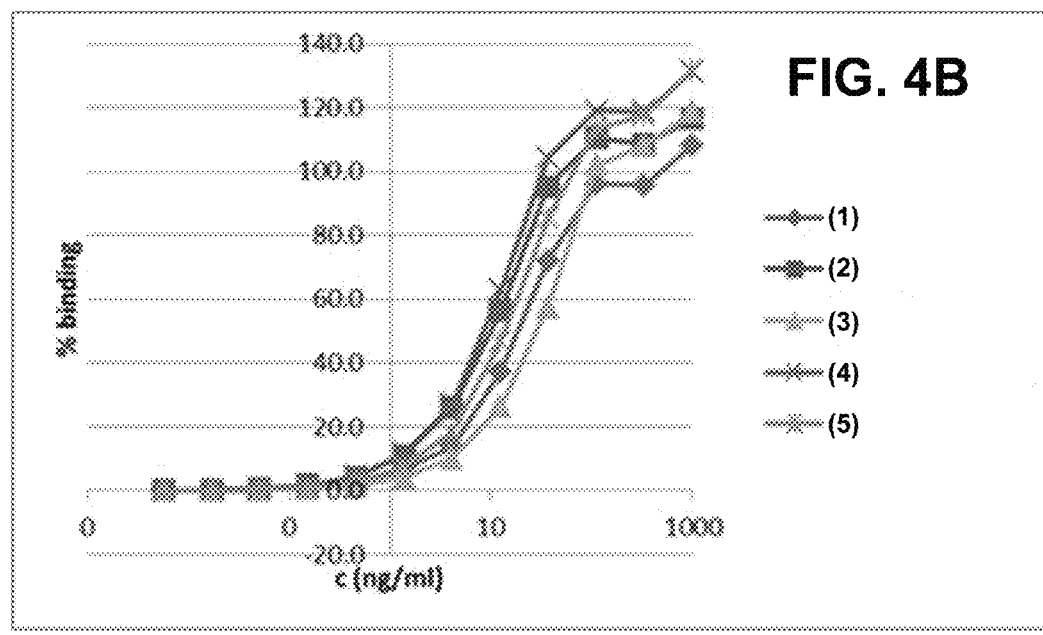

HUMANIZED ANTI-TAU(PS422) ANTIBODIES AND METHODS OF USE

CROSS REFERENCE TO RELATED APPLICATIONS

This application claims benefit of European Patent Application No. 15173511.5, filed on Jun. 24, 2015, which is incorporated by reference herein in its entirety.

FIELD OF THE INVENTION

The present invention relates to humanized anti-Tau (pS422) antibodies which specifically bind to a phosphorylated tau fragment of SEQ ID NO: 03 and their use for the treatment of brain diseases.

INCORPORATION BY REFERENCE OF SEQUENCE LISTING

This application contains references to amino acids and/or nucleic acid sequences that have been filed concurrently herewith as sequence listing text file "0399723.txt", file size of 68 KB, created on Jun. 21, 2016. The aforementioned sequence listing is hereby incorporated by reference in its entirety pursuant to 37 C.F.R. § 1.52(e)(5).

BACKGROUND OF THE INVENTION

Human tau (microtubule-associated protein tau (neurofibrillary tangle protein, paired helical filament-tau, PHF-tau)) is a neuronal microtubule-associated protein found predominantly in axons and functions to promote tubulin polymerization and to stabilize microtubules. Eight isoforms (isoform A, B, C, D, E, F, G, fetal-tau) are found in the human brain, the longest isoform comprising 441 amino acids (isoform F, Uniprot P10636-8). Tau and its properties are also described by Reynolds, C. H., et al., J. Neurochem. 69 (1997) 191-198.

Tau, in its hyperphosphorylated form, is the major component of paired helical filaments (PHF), the building block of neurofibrillary lesions in Alzheimer's disease (AD) brain. Tau can be phosphorylated at its serine or threonine residues by several different kinases including GSK3beta, cdk5, MARK and members of the MAP kinase family.

Tauopathies are characterized by abnormal hyperphosphorylation of tau and are according to Iqbal, K., et al. (Biochim. Biophys. Acta 1739 (2005) 198-210):

Alzheimer disease, including tangle-only form of the disease
Down syndrome, adult cases
Guam Parkinsonism dementia complex
Dementia pugilistica
Pick disease
Dementia with argyrophilic grains
Fronto-temporal dementia
Cortico-basal degeneration
Pallido-ponto-nigral degeneration
Progressive supranuclear palsy
Gerstmann-Sträussler-Scheinker disease with tangles.

So far nearly 40 serine (S)/threonine (T) phosphorylation sites have been found in tau from Alzheimer's disease brains (Hanger, D. P., et al., J. Biol. Chem. 282 (2007) 23645-23654). The development of tau pathology in Alzheimer's disease is related to its phosphorylation state. However, most of the 40 phosphorylation sites are not associated with disease pathology since they are also found in tau extracted from healthy, fetal brain tissue. Only a few phosphorylations are unique to the disease state and are presumably responsible for the abnormal, aggregation and characteristic insolubility that define tau in the PHFs of Alzheimer brain (Morishima-Kawashima, M., et al., J. Biol. Chem. 270 (1995) 823-829). According to Pei, J. J., et al. (J. Alzheimer's Disease 14 (2008) 385-392) the existing literature provides limited and unclear information about which of these sites are specific to AD brains. Pei used a list of phospho-specific antibodies to tau and measured their levels in homogenates of the medial temporal cortex from 22 AD patients and 10 controls.

Bussiere, T., et al. (Acta Neuropathol. 97 (1999) 221-230) described that phosphorylated serine 422 (pS422) on tau proteins is a pathological epitope found in several diseases with neurofibrillary degeneration. Augustinack, J. C., et al., (Acta Neuropathol. 103 (2002) 26-35) described pS422 as correlating with the severity of neuronal pathology in Alzheimer's disease. Guillozet-Bongaarts, A., (J. Neurochem. 97 (2006) 1005-1014) described the phosphorylation of tau at serine 422 as being part of the maturation process of PHFs. Tau pS422 is also found in association with developing pathology in various transgenic mouse models of Alzheimer's disease. Thus, Deters, N., et al., mentioned in Biochem. Biophys. Res. Commun. 379 (2009) 400-405 that double-transgenic Dom5/pR5 mice showed 7-fold increased numbers of hippocampal neurons that contain tau specifically phosphorylated the pathological 5422 epitope. Goetz, J., et al., (Science 293 (2001) 1491-1495) reported the appearance of tau phosphorylated at S422 in the brains of tau P301L transgenic mice injected with Abeta42 fibrils.

EP 2 009 104 relates to epitopes of the tau protein which occur in a phosphorylated state in tau protein from Alzheimer's disease PHFs and to the use of said epitopes for the generation of antibodies specifically detecting Alzheimer's tau protein. WO 2002/062851 and U.S. Pat. No. 7,446,180 relate to antibodies with a specificity to an abnormally truncated form of tau protein and diagnostic and therapeutic aspects in relation to Alzheimer's disease and related tauopathies.

WO 1998/22120 relates to a method of treating a patient with Alzheimer's disease comprising the step of administering to the patient an antibody against phosphorylated tau fragment of amino acids about 207 to about 222, amino acids about 224 to about 240, and amino acids about 390 to about 408. Animal studies where the phosphorylated tau fragment 379-408 [P-Ser396,404] is used to vaccinate tau transgenic mice are mentioned in Asuni, A. A., et al., J. Neuroscience 27 (2007) 9115-9129. US 2008/0050383 relates to methods of treating and preventing Alzheimer's disease or other tauopathies in a subject by administering a tau protein fragment.

Hasegawa, M., et al. (FEBS Lett. 384 (1996) 25-30) report monoclonal antibody (AP422) specific for phosphoserine 422 in microtubule-associated protein tau.

In WO 2001/55725 an antibody that specifically recognizes tau and an antibody that specifically recognizes phospho-tau (181) for use in a method for the in vivo diagnosis of a tauopathy and/or for the in vivo differential diagnosis of a tauopathy versus a non-tauopathy is reported.

In WO 2002/027017 an antibody prepared from a polypeptide immunogen having a phosphorylated serine is reported. WO 2002/062851 relates to antibodies with a specificity to an abnormally truncated form of tau protein and diagnostic and therapeutic aspects in relation to Alzheimer's disease and related tauopathies.

In WO 2004/016655 an antibody specific to a central nervous system (CNS) tau protein, wherein the antibody specifically recognizes a CNS tau protein but not a peripheral tau protein and wherein the antibody specifically recognizes an amino acid sequence of a connective portion between the amino acid sequence encoded by Exon 4 of a gene encoding a tau protein and the amino acid sequence encoded by Exon 5 thereof as an epitope is reported.

Monoclonal antibodies against Tau(pS422) are described, for example, in EP 1 876 185. Polyclonal antibodies against Tau(pS422) are commercially available (e.g., ProSci Inc. and Biosource International).

In WO 2006/055178 a method for inhibiting the phosphorylation of tau protein at Ser202/Thr205 comprising contacting a sample containing a tau protein with the antibody or antigen binding fragment that binds amyloid beta-derived diffusible ligands thereby inhibiting the phosphorylation of tau protein at Ser202/Thr205 is reported.

An antibody preparation that specifically binds to tau phosphorylated at tyr394 and/or tyr310 is reported in WO 2007/019273. Animal studies where the phosphorylated tau fragment 379-408 [P-Ser396,404] is used to vaccinate tau transgenic mice are mentioned in Asuni, A. A. et al., J. Neuroscience 27 (2007) 9115-9129.

EP 2 009 104 relates to epitopes of the tau protein which occur in a phosphorylated state in tau protein from Alzheimer's disease PHFs and to the use of said epitopes for the generation of antibodies specifically detecting Alzheimer's tau protein.

US 2008/0050383 relates to methods of treating and preventing Alzheimer's disease or other tauopathies in a subject by administering a tau protein fragment.

In WO 2010/037135 an isolated, synthetic or recombinant polypeptide or peptide comprising a first domain comprising, or consisting of, a ligand for a blood brain barrier (BBB) receptor or equivalent and a second domain comprising, or consisting of an enzyme or composition that slows the rate of aggregation of a protein aggregate, inhibits the formation of a protein aggregate, or reverses, digests or dissolves a protein aggregate is reported. An antibody, particularly a monoclonal antibody or functional parts thereof, capable of recognizing and binding to a tau protein in vitro and/or in vivo is reported in WO 2010/115843.

In WO 2011/026031 a monoclonal antibody or its fragment that specifically binds tau oligomers and does not bind soluble tau or tau fibrils, useful for treating tauopathy, e.g., Alzheimer's disease, progressive supranuclear palsy and corticobasal degeneration is reported. An isolated antibody that specifically binds human tau protein phosphorylated at one or more of Ser(238) and Thr(245) is reported in WO 2011/053565.

In WO 2012/045882 an antibody which specifically binds to a phospho-epitope on the mammalian tau protein, useful for treating neurodegenerative disorders such as tauopathies, and for treating or alleviating cognitive deficits is reported. A human monoclonal anti-tau antibody or a tau binding fragment thereof is reported in WO 2012/049570. A method of preventing or treating Alzheimer's disease or other tauopathies in a subject, comprising administering antibodies to a human in need of therapy for Alzheimer's disease or other tauopathy, the antibodies having specificity to abnormal forms of tau protein, said antibody showing no binding and/or reactivity to a normal tau protein and being administered under conditions and in an amount(s) effective to prevent or treat Alzheimer's disease or other tauopathy is reported in WO 2012/106363.

In WO 2012/149365 an antibody which shows reactivity with aggregated tau and substantially no reactivity with non-aggregated tau, wherein the aggregated tau comprises at least two tau proteins cross-linked to each other, either directly or through a linker, at one or more cysteine residues is reported.

A composition useful in treating tauopathy, e.g., Alzheimer disease comprises antibody binding to tau, phosphorylated serine modified compound at specific position specifically binding to specific phosphorylated tau and its fragment and carrier is reported in WO 2010/142423.

In EP 1 876 185 A, an antibody which recognizes phosphorylated polypeptides is reported. In WO 2013/151762 a humanized tau antibody is reported. In WO 2014/016737 novel chicken monoclonal antibodies against human phosphorylated tau and uses thereof are reported. In WO 2014/016737 novel chicken monoclonal antibodies against human phosphorylated tau and uses thereof are reported. Antibodies selective for pathological tau dimers and prefibrillar pathological tau oligomers and their uses in treatment, diagnosis and monitoring of tauopathies are reported in WO 2012/149365.

In WO 2015/091656 humanized anti-Tau(pS422) antibodies and methods of use are reported. In WO 2015/101586 bispecific anti-hapten/anti-blood brain barrier receptor antibodies, complexes thereof and their use as blood brain barrier shuttles are reported.

BRIEF SUMMARY OF THE INVENTION

The invention provides anti-human Tau(pS422) antibodies, especially humanized anti-human Tau(pS422) antibodies, and methods of using the same.

The humanized antibodies as reported herein were not available by standard humanization methods. It was required to introduce non-standard mutations in the amino acid sequence in order to obtain a humanized antibody with comparable binding characteristics and pharmacokinetic properties as the parent rabbit antibody comprising variable domains with the amino acid sequence of SEQ ID NO: 07 and SEQ ID NO: 11. This is especially important as the antibodies as reported herein are intended to cross the human blood-brain-barrier and to be effective within the human brain. Thus, the generally applied criteria for the selection of humanized antibodies are not sufficiently stringent in order to be applied directly in the current case.

One aspect as reported herein is a (humanized) antibody that specifically binds to human Tau(pS422), wherein the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to human tau that has the amino acid sequence of SEQ ID NO: 01 and that has the amino acid mutation S422A.

The antibodies as reported herein show a selectivity with respect to human tau phosphorylated at the serine at position 422, with respect to not-phosphorylated wild-type human tau and the tau mutant S422A. The not-phosphorylated wild-type human tau and the tau mutant S422A are not bound at all or with a lower affinity, respectively.

One aspect as reported herein is a (humanized) anti-human Tau(pS422) monoclonal antibody which is a humanized variant of antibody mAb 086 produced by grafting the HVRs of mAb 086 onto human framework and constant regions, wherein selected human variable region framework residues are optionally substituted as follows:

- a selected human variable region framework residue is substituted by an equivalent framework amino acid from the rabbit mAb 086 antibody when the amino acid (1) noncovalently binds antigen directly, (2) is adjacent to an HVR region, (3) otherwise interacts with an HVR region, or (4) participates in the VL-VH interface; or
- a human framework amino acid that is unusual for a human immunoglobulin at that position is substituted with an amino acid from the equivalent position of the rabbit donor antibody or from the equivalent position of a more typical human immunoglobulin.

One aspect as reported herein is a (humanized) antibody that specifically binds to human Tau(pS422) comprising the amino acid sequence of SEQ ID NO: 02, wherein the antibody has inhibitory activity against Tau(pS422)-induced cytotoxicity, and wherein the antibody binds to a fragment of the human Tau(pS422) protein, and wherein said fragment comprises the amino acids residues 416 to 430 of SEQ ID NO: 02, and wherein said antibody comprises a human constant region, wherein the antibody is selected from any of (1) to (2) below;

(1)
  (a) an antibody comprising a heavy chain having the amino acid sequence of SEQ ID NO: 08 as HVR-H1, the amino acid sequence of SEQ ID NO: 09 as HVR-H2, and the amino acid sequence of SEQ ID NO: 10 as HVR-H3, and a light chain having the amino acid sequence of SEQ ID NO: 70 as HVR-L1, the amino acid sequence of SEQ ID NO: 72 as HVR-L2, and the amino acid sequence of SEQ ID NO: 15 as HVR-L3; or
  (b) an antibody comprising a heavy chain having the amino acid sequence of SEQ ID NO: 08 as HVR-H1, the amino acid sequence of SEQ ID NO: 09 as HVR-H2, and the amino acid sequence of SEQ ID NO: 10 as HVR-H3, and a light chain having the amino acid sequence of SEQ ID NO: 12 as HVR-L1, the amino acid sequence of SEQ ID NO: 14 as HVR-L2, and the amino acid sequence of SEQ ID NO: 74 as HVR-L3; or
  (c) an antibody comprising a heavy chain having the amino acid sequence of SEQ ID NO: 08 as HVR-H1, the amino acid sequence of SEQ ID NO: 09 as HVR-H2, and the amino acid sequence of SEQ ID NO: 10 as HVR-H3, and a light chain having the amino acid sequence of SEQ ID NO: 71 as HVR-L1, the amino acid sequence of SEQ ID NO: 73 as HVR-L2, and the amino acid sequence of SEQ ID NO: 15 as HVR-L3; or
  (d) an antibody comprising a heavy chain having the amino acid sequence of SEQ ID NO: 08 as HVR-H1, the amino acid sequence of SEQ ID NO: 77 as HVR-H2, and the amino acid sequence of SEQ ID NO: 10 as HVR-H3, and a light chain having the amino acid sequence of SEQ ID NO: 12 as HVR-L1, the amino acid sequence of SEQ ID NO: 14 as HVR-L2, and the amino acid sequence of SEQ ID NO: 75 as HVR-L3;

(2) an antibody having one or more conservative amino acid substitutions in the antibody of (1), which has equivalent activity as the antibody of (1).

One aspect as reported herein is a humanized antibody that specifically binds to human Tau(pS422), wherein the antibody comprises
  a) in the heavy chain variable domain the HVRs of SEQ ID NO: 08, 18 and 10, or
  b) in the heavy chain variable domain the HVRs of SEQ ID NO: 08, 09 and 10, or
  c) in the heavy chain variable domain the HVRs of SEQ ID NO: 08, 77 and 10.

In one preferred embodiment the humanized antibody as reported herein has in the light chain variable domain at position 32 a lysine (K) amino acid residue (numbering according to Kabat).

In one embodiment the humanized antibody comprises
  a) in the light chain variable domain the HVRs of SEQ ID NO: 71, 73 and 15, or
  b) in the light chain variable domain the HVRs of SEQ ID NO: 70, 72 and 15, or
  c) in the light chain variable domain the HVRs of SEQ ID NO: 12, 14 and 79, or
  d) in the light chain variable domain the HVRs of SEQ ID NO: 71, 81 and 15.

In one embodiment the humanized antibody as reported herein comprises
  a) in the heavy chain variable domain the HVRs of SEQ ID NO: 08, 18 and 10, and in the light chain variable domain the HVRs of SEQ ID NO: 13, 14 and 15, or
  b) in the heavy chain variable domain the HVRs of SEQ ID NO: 08, 09 and 10, and in the light chain variable domain the HVRs of SEQ ID NO: 12, 05 and 15, or
  c) in the heavy chain variable domain the HVRs of SEQ ID NO: 08, 09 and 10, and in the light chain variable domain the HVRs of SEQ ID NO: 13, 14 and 15, or
  d) in the heavy chain variable domain the HVRs of SEQ ID NO: 08, 09 and 10, and in the light chain variable domain the HVRs of SEQ ID NO: 71, 73 and 15, or
  e) in the heavy chain variable domain the HVRs of SEQ ID NO: 08, 09 and 10, and in the light chain variable domain the HVRs of SEQ ID NO: 70, 72 and 15, or
  f) in the heavy chain variable domain the HVRs of SEQ ID NO: 08, 77 and 10, and in the light chain variable domain the HVRs of SEQ ID NO: 12, 14 and 79, or
  g) in the heavy chain variable domain the HVRs of SEQ ID NO: 08, 09 and 10, and in the light chain variable domain the HVRs of SEQ ID NO: 12, 14 and 79, or
  h) in the heavy chain variable domain the HVRs of SEQ ID NO: 08, 77 and 10, and in the light chain variable domain the HVRs of SEQ ID NO: 71, 81 and 15.

One preferred aspect is a humanized antibody that specifically binds to human Tau(pS422), wherein the antibody comprises the HVRs from VH35H5 and VL31A1.

In one embodiment this humanized antibody that specifically binds to human Tau(pS422) comprises in the heavy chain variable domain the HVRs of SEQ ID NO: 08, 09 and 10, and in the light chain variable domain the HVRs of SEQ ID NO: 70, 72 and 15. SEQ ID NO: 70 corresponds to the sequence of HVR-L1 and has at position 32 according to Kabat the amino acid residue lysine.

In one embodiment this humanized antibody that specifically binds to human Tau(pS422) comprises a heavy chain variable domain that has the amino acid sequence of SEQ ID NO: 65 and a light chain variable domain that has the amino acid sequence of SEQ ID NO: 66.

One preferred aspect is a humanized antibody that specifically binds to human Tau(pS422), wherein the antibody comprises the HVRs from VH35H5 and VL49G1.

In one preferred embodiment this humanized antibody that specifically binds to human Tau(pS422) comprises in the heavy chain variable domain the HVRs of SEQ ID NO: 08, 09 and 10, and in the light chain variable domain the HVRs of SEQ ID NO: 71, 73 and 15. SEQ ID NO: 71 corresponds to the sequence of HVR-L1 and has at position 32 according to Kabat the amino acid residue lysine.

In one embodiment this humanized antibody that specifically binds to human Tau(pS422) comprises a heavy chain variable domain that has the amino acid sequence of SEQ ID NO: 65 and a light chain variable domain that has the amino acid sequence of SEQ ID NO: 67.

One preferred aspect is a humanized antibody that specifically binds to human Tau(pS422), wherein the antibody comprises the HVRs from VH35H5 and VL35F2.

In one embodiment this humanized antibody that specifically binds to human Tau(pS422) comprises in the heavy chain variable domain the HVRs of SEQ ID NO: 08, 09 and 10, and in the light chain variable domain the HVRs of SEQ ID NO: 12, 14 and 74. SEQ ID NO: 12 corresponds to the sequence of HVR-L1 and has at position 32 according to Kabat the amino acid residue lysine.

In one embodiment this humanized antibody that specifically binds to human Tau(pS422) comprises a heavy chain variable domain that has the amino acid sequence of SEQ ID NO: 65 and a light chain variable domain that has the amino acid sequence of SEQ ID NO: 68.

One preferred aspect is a humanized antibody that specifically binds to human Tau(pS422), wherein the antibody comprises the HVRs from VH76A6 and VL35G4.

In one embodiment this humanized antibody that specifically binds to human Tau(pS422) comprises in the heavy chain variable domain the HVRs of SEQ ID NO: 08, 77 and 10, and in the light chain variable domain the HVRs of SEQ ID NO: 12, 14 and 75. SEQ ID NO: 12 corresponds to the sequence of HVR-L1 and has at position 32 according to Kabat the amino acid residue lysine.

In one embodiment this humanized antibody that specifically binds to human Tau(pS422) comprises a heavy chain variable domain that has the amino acid sequence of SEQ ID NO: 76 and a light chain variable domain that has the amino acid sequence of SEQ ID NO: 69.

In one embodiment the humanized antibody as reported herein comprises
a) a heavy chain variable domain of SEQ ID NO: 20 and a light chain variable domain of SEQ ID NO: 17, or
b) a heavy chain variable domain of SEQ ID NO: 19 and a light chain variable domain of SEQ ID NO: 16, or
c) a heavy chain variable domain of SEQ ID NO: 19 and a light chain variable domain of SEQ ID NO: 17, or
d) a heavy chain variable domain of SEQ ID NO: 21 and a light chain variable domain of SEQ ID NO: 17, or
e) a heavy chain variable domain of SEQ ID NO: 65 and a light chain variable domain of SEQ ID NO: 67, or
f) a heavy chain variable domain of SEQ ID NO: 65 and a light chain variable domain of SEQ ID NO: 66, or
g) a heavy chain variable domain of SEQ ID NO: 76 and a light chain variable domain of SEQ ID NO: 78, or
h) a heavy chain variable domain of SEQ ID NO: 19 and a light chain variable domain of SEQ ID NO: 78, or
i) a heavy chain variable domain of SEQ ID NO: 76 and a light chain variable domain of SEQ ID NO: 80.

In one preferred embodiment the humanized antibody comprises a heavy chain variable domain of SEQ ID NO: 65 and a light chain variable domain of SEQ ID NO: 66 or 67 or 68.

In one preferred embodiment the humanized antibody comprises a heavy chain variable domain of SEQ ID NO: 76 and a light chain variable domain of SEQ ID NO: 69.

In one embodiment the humanized antibody comprises a heavy chain variable domain of SEQ ID NO: 76 or 19 and a light chain variable domain of SEQ ID NO: 78.

In one embodiment the antibody is for use in the treatment of Alzheimer's disease.

In one embodiment the antibody is effector function silent. In one embodiment the antibody has no effector function. In one embodiment the antibody is of the human IgG1 subclass and has the mutations L234A, L235A and P329G in both heavy chains (numbering according to the EU index of Kabat).

In one embodiment the antibody
i) specifically binds to a polypeptide that has the amino acid sequence of SEQ ID NO: 03, and/or
ii) does not bind to full length human tau (SEQ ID NO: 01) at 1 µg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02).

In one embodiment the antibody has an $EC_{50}$ value for
a) the human Tau(pS422) fragment that has the amino acid sequence of SEQ ID NO: 03 of 6 ng/mL or less, and/or
b) the full length human Tau(pS422) that has the amino acid sequence of SEQ ID NO: 02 of 4.5 ng/mL or less, and/or
c) aggregates of human Tau(pS422) that has the amino acid sequence of SEQ ID NO: 02 of 30 ng/mL or less, and/or
d) the human tau that has the amino acid sequence of SEQ ID NO: 01 and that has the amino acid mutation S422A of 125 ng/mL or less.

In one embodiment the antibody specifically binds to human Tau(pS422) (SEQ ID NO: 02) and does not bind to human tau (SEQ ID NO: 01).

In one embodiment the antibody is a monoclonal antibody.

In one embodiment the antibody is an antibody fragment that binds to human Tau(pS422) and
i) specifically binds to a polypeptide that has the amino acid sequence of SEQ ID NO: 03, and/or
ii) does not bind to full length human tau (SEQ ID NO: 01) at 1 µg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or vii) has an $EC_{50}$ value for the full length human Tau (pS422) that has the amino acid sequence of SEQ ID NO: 02 of 4.5 ng/mL or less, and/or
viii) has an $EC_{50}$ value for aggregates of human Tau (pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

In one embodiment the antibody is
a) a full length antibody of the human subclass IgG1, or
b) a full length antibody of the human subclass IgG4, or
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
f) a full length antibody of the human subclass IgG4 with the mutations S228P and P329G in both heavy chains and the mutations T366W and S354C in one heavy chain and the mutations T366S, L368A, Y407V and Y349C in the respective other heavy chain.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain comprises the HVRs of SEQ ID NO: 08, SEQ ID NO: 18 and SEQ ID NO: 10,
ii) the constant region is a human IgG1 constant region, wherein the C-terminal lysine residue or the glycine-lysine dipeptide can be present or absent, and
iii) the constant region comprises the amino acid changes L234A, L235A and P329G,
b) the antibody comprises two antibody light chains each comprising a light chain variable domain and a light chain constant domain, wherein
i) the variable domain comprises the HVRs of SEQ ID NO: 13, SEQ ID NO: 14 and SEQ ID NO: 15,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 µg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(p S422) that has the amino acid sequence of SEQ ID NO: 02 of 4.5 ng/mL or less, and/or
viii) has an $EC_{50}$ value for aggregates of human Tau(p S422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain comprises the HVRs of SEQ ID NO: 08, SEQ ID NO: 09 and SEQ ID NO: 10,
ii) the constant region is a human IgG1 constant region, wherein the C-terminal lysine residue or the glycine-lysine dipeptide can be present or absent, and
iii) the constant region comprises the amino acid changes L234A, L235A and P329G,
b) the antibody comprises two antibody light chains each comprising a light chain variable domain and a light chain constant domain, wherein
i) the variable domain comprises the HVRs of SEQ ID NO: 12, SEQ ID NO: 05 and SEQ ID NO: 15,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 µg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(p S422) that has the amino acid sequence of SEQ ID NO: 02 of 4.5 ng/mL or less, and/or
viii) has an $EC_{50}$ value for aggregates of human Tau(p S422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain comprises the HVRs of SEQ ID NO: 08, SEQ ID NO: 09 and SEQ ID NO: 10,
ii) the constant region is a human IgG1 constant region, wherein the C-terminal lysine residue or the glycine-lysine dipeptide can be present or absent, and iii) the constant region comprises the amino acid changes L234A, L235A and P329G, b) the antibody comprises two antibody light chains each comprising a light chain variable domain and a light chain constant domain, wherein
   i) the variable domain comprises the HVRs of SEQ ID NO: 13, SEQ ID NO: 14 and SEQ ID NO: 15,
   ii) the constant region is a human kappa light chain constant region or a human lambda light chain constant region,
and
c) the antibody
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human Tau(pS422) fragment that has the amino acid sequence of SEQ ID NO: 03 of 6 ng/mL or less, and/or
   vii) has an $EC_{50}$ value for the full length human Tau(pS422) that has the amino acid sequence of SEQ ID NO: 02 of 4.5 ng/mL or less, and/or
   viii) has an $EC_{50}$ value for aggregates of human Tau(pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
   a) the antibody comprises two antibody heavy chains each comprising a heavy chain variable domain and a heavy chain constant region, wherein
      i) the variable domain comprises the HVRs of SEQ ID NO: 08, SEQ ID NO: 09 and SEQ ID NO: 10,
      ii) the constant region is a human IgG1 constant region, wherein the C-terminal lysine residue or the glycine-lysine dipeptide can be present or absent, and iii) the constant region comprises the amino acid changes L234A, L235A and P329G,
   b) the antibody comprises two antibody light chains each comprising a light chain variable domain and a light chain constant domain, wherein
      i) the variable domain comprises the HVRs of SEQ ID NO: 71, SEQ ID NO: 73 and SEQ ID NO: 15,
      ii) the constant region is a human kappa light chain constant region or a human lambda light chain constant region,
   and
   c) the antibody
      i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human Tau(pS422) fragment that has the amino acid sequence of SEQ ID NO: 03 of 6 ng/mL or less, and/or
      vii) has an $EC_{50}$ value for the full length human Tau(pS422) that has the amino acid sequence of SEQ ID NO: 02 of 4.5 ng/mL or less, and/or
      viii) has an $EC_{50}$ value for aggregates of human Tau(pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
   a) the antibody comprises two antibody heavy chains each comprising a heavy chain variable domain and a heavy chain constant region, wherein
      i) the variable domain comprises the HVRs of SEQ ID NO: 08, SEQ ID NO: 09 and SEQ ID NO: 10,
      ii) the constant region is a human IgG1 constant region, wherein the C-terminal lysine residue or the glycine-lysine dipeptide can be present or absent, and
      iii) the constant region comprises the amino acid changes L234A, L235A and P329G,
   b) the antibody comprises two antibody light chains each comprising a light chain variable domain and a light chain constant domain, wherein
      i) the variable domain comprises the HVRs of SEQ ID NO: 70, SEQ ID NO: 72 and SEQ ID NO: 15,
      ii) the constant region is a human kappa light chain constant region or a human lambda light chain constant region,
   and
   c) the antibody
      i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
   vi) has an $EC_{50}$ value for the human Tau(pS422) fragment that has the amino acid sequence of SEQ ID NO: 03 of 6 ng/mL or less, and/or
      vii) has an $EC_{50}$ value for the full length human Tau(pS422) that has the amino acid sequence of SEQ ID NO: 02 of 4.5 ng/mL or less, and/or
      viii) has an $EC_{50}$ value for aggregates of human Tau(pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain comprises the HVRs of SEQ ID NO: 08, SEQ ID NO: 09 and SEQ ID NO: 10,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 12, SEQ ID NO: 14 and SEQ ID NO: 79,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human Tau(pS422) fragment that has the amino acid sequence of SEQ ID NO: 03 of 6 ng/mL or less, and/or
    vii) has an $EC_{50}$ value for the full length human Tau(pS422) that has the amino acid sequence of SEQ ID NO: 02 of 4.5 ng/mL or less, and/or
    viii) has an $EC_{50}$ value for aggregates of human Tau(pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain comprises the HVRs of SEQ ID NO: 08, SEQ ID NO: 09 and SEQ ID NO: 10,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 12, SEQ ID NO: 14 and SEQ ID NO: 74,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human Tau(pS422) fragment that has the amino acid sequence of SEQ ID NO: 03 of 6 ng/mL or less, and/or
    vii) has an $EC_{50}$ value for the full length human Tau(pS422) that has the amino acid sequence of SEQ ID NO: 02 of 4.5 ng/mL or less, and/or
    viii) has an $EC_{50}$ value for aggregates of human Tau(pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain comprises the HVRs of SEQ ID NO: 08, SEQ ID NO: 77 and SEQ ID NO: 10,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 12, SEQ ID NO: 14 and SEQ ID NO: 75,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or vi) has an $EC_{50}$ value for the human Tau(pS422) fragment that has the amino acid sequence of SEQ ID NO: 03 of 6 ng/mL or less, and/or vii) has an $EC_{50}$ value for the full length human Tau(pS422) that has the amino acid sequence of SEQ ID NO: 02 of 4.5 ng/mL or less, and/or viii) has an $EC_{50}$ value for aggregates of human Tau(pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain has the amino acid sequence of SEQ ID NO: 20,
ii) the constant region is a human IgG1 constant region, wherein the C-terminal lysine residue or the glycine-lysine dipeptide can be present or absent, and
iii) the constant region comprises the amino acid changes L234A, L235A and P329G,
b) the antibody comprises two antibody light chains each comprising a light chain variable domain and a light chain constant domain, wherein
i) the variable domain has the amino acid sequence of SEQ ID NO: 17,
ii) the constant region is a human kappa light chain constant region or a human lambda light chain constant region, and
c) the antibody
i) specifically binds to a polypeptide that has the amino acid sequence of SEQ ID NO: 03, and/or
ii) does not bind to full length human tau (SEQ ID NO: 01) at 1 µg/mL, and/or iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain has the amino acid sequence of SEQ ID NO: 19,
ii) the constant region is a human IgG1 constant region, wherein the C-terminal lysine residue or the glycine-lysine dipeptide can be present or absent, and iii) the constant region comprises the amino acid changes L234A, L235A and P329G,
b) the antibody comprises two antibody light chains each comprising a light chain variable domain and a light chain constant domain, wherein
i) the variable domain has the amino acid sequence of SEQ ID NO: 16,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 µg/mL, and/or iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
i) the variable domain has the amino acid sequence of SEQ ID NO: 19,
ii) the constant region is a human IgG1 constant region, wherein the C-terminal lysine residue or the glycine-lysine dipeptide can be present or absent, and iii) the constant region comprises the amino acid changes L234A, L235A and P329G,
b) the antibody comprises two antibody light chains each comprising a light chain variable domain and a light chain constant domain, wherein
i) the variable domain has the amino acid sequence of SEQ ID NO: 17,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 µg/mL, and/or iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
a) the antibody comprises two antibody heavy chains each comprising a heavy chain variable domain and a heavy chain constant region, wherein
  i) the variable domain has the amino acid sequence of SEQ ID NO: 21,
  ii) the constant region is a human IgG1 constant region, wherein the C-terminal lysine residue or the glycine-lysine dipeptide can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain has the amino acid sequence of SEQ ID NO: 17,
  ii) the constant region is a human kappa light chain constant region or a human lambda light chain constant region,
and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau(pS422) that has the amino acid sequence of SEQ ID NO: 02 of 4.5 ng/mL or less, and/or
  viii) has an $EC_{50}$ value for aggregates of human Tau(pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
a) the antibody comprises two antibody heavy chains each comprising a heavy chain variable domain and a heavy chain constant region, wherein
  i) the variable domain has the amino acid sequence of SEQ ID NO: 65,
  ii) the constant region is a human IgG1 constant region, wherein the C-terminal lysine residue or the glycine-lysine dipeptide can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain has the amino acid sequence of SEQ ID NO: 67,
  ii) the constant region is a human kappa light chain constant region or a human lambda light chain constant region,
and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau(pS422) that has the amino acid sequence of SEQ ID NO: 02 of 4.5 ng/mL or less, and/or
  viii) has an $EC_{50}$ value for aggregates of human Tau(pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
a) the antibody comprises two antibody heavy chains each comprising a heavy chain variable domain and a heavy chain constant region, wherein
  i) the variable domain has the amino acid sequence of SEQ ID NO: 65,
  ii) the constant region is a human IgG1 constant region, wherein the C-terminal lysine residue or the glycine-lysine dipeptide can be present or absent, and
  iii) the constant region comprises the amino acid changes L234A, L235A and P329G, b) the antibody comprises two antibody light chains each comprising a light chain variable domain and a light chain constant domain, wherein
  i) the variable domain has the amino acid sequence of SEQ ID NO: 66,
  ii) the constant region is a human kappa light chain constant region or a human lambda light chain constant region,
and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau(pS422) that has the amino acid sequence of SEQ ID NO: 02 of 4.5 ng/mL or less, and/or
  viii) has an $EC_{50}$ value for aggregates of human Tau(pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain has the amino acid sequence of SEQ ID NO: 65,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain has the amino acid sequence of SEQ ID NO: 68,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human Tau(pS422) fragment that has the amino acid sequence of SEQ ID NO: 03 of 6 ng/mL or less, and/or
    vii) has an $EC_{50}$ value for the full length human Tau(pS422) that has the amino acid sequence of SEQ ID NO: 02 of 4.5 ng/mL or less, and/or
    viii) has an $EC_{50}$ value for aggregates of human Tau(pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

One aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain has the amino acid sequence of SEQ ID NO: 19,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain has the amino acid sequence of SEQ ID NO: 78,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human Tau(pS422) fragment that has the amino acid sequence of SEQ ID NO: 03 of 6 ng/mL or less, and/or
    vii) has an $EC_{50}$ value for the full length human Tau(pS422) that has the amino acid sequence of SEQ ID NO: 02 of 4.5 ng/mL or less, and/or
    viii) has an $EC_{50}$ value for aggregates of human Tau(pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

One preferred aspect as reported herein is a (humanized) anti-human Tau(pS422) antibody, characterized in that
  a) the antibody comprises two antibody heavy chains each comprising a heavy chain variable domain and a heavy chain constant region, wherein
    i) the variable domain has the amino acid sequence of SEQ ID NO: 76,
    ii) the constant region is a human IgG1 constant region, wherein the C-terminal lysine residue or the glycine-lysine dipeptide can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain has the amino acid sequence of SEQ ID NO: 69,
    ii) the constant region is a human kappa light chain constant region or a human lambda light chain constant region,
  and
  c) the antibody
    i) specifically binds to a polypeptide that has the amino acid sequence of SEQ ID NO: 03, and/or
    ii) does not bind to full length human tau (SEQ ID NO: 01) at 1 µg/mL, and/or iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human Tau(pS422) fragment that has the amino acid sequence of SEQ ID NO: 03 of 6 ng/mL or less, and/or
    vii) has an $EC_{50}$ value for the full length human Tau(pS422) that has the amino acid sequence of SEQ ID NO: 02 of 4.5 ng/mL or less, and/or
    viii) has an $EC_{50}$ value for aggregates of human Tau(pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

In one preferred embodiment of all aspects the anti-human Tau(pS422) antibody is characterized in that the antibody has in the light chain variable domain at position 32, a lysine (K) amino acid residue (numbering according to Kabat).

In one preferred embodiment of all aspects the anti-human Tau(pS422) antibody is characterized in that the antibody has in the heavy chain variable domain at positions 4, 24 and 78, a valine residue.

In one preferred embodiment of all aspects the anti-human Tau(pS422) antibody is characterized in that the antibody has in the heavy chain variable domain at position 71, an arginine residue.

One aspect as reported herein is an isolated nucleic acid encoding a (humanized) antibody as reported herein. This nucleic acid comprises a nucleic acid encoding the antibody heavy chain and one nucleic acid encoding the antibody light chain. This nucleic acid comprises at least one expression cassette. Preferably said nucleic acid comprises two expression cassettes.

One aspect as reported herein is a host cell comprising the nucleic acid as reported herein.

One aspect as reported herein is a method of producing a (humanized) antibody comprising the steps of culturing the host cell as reported herein so that the antibody is produced.

In one embodiment the method further comprises the step of recovering the antibody from the cell or the cultivation medium.

One aspect as reported herein is a pharmaceutical formulation comprising the (humanized) antibody as reported herein and a pharmaceutically acceptable carrier.

In one embodiment the pharmaceutical formulation further comprises an additional therapeutic agent.

In one embodiment the additional therapeutic agent is an anti-amyloid therapeutic agent. In one embodiment the anti-amyloid therapeutic agent is an anti-human alpha-synuclein antibody or an anti-Abeta antibody.

One aspect as reported herein is the (humanized) antibody as reported herein for use as a medicament.

One aspect as reported herein is the (humanized) antibody as reported herein for use in the treatment of Alzheimer's disease.

One aspect as reported herein is the (humanized) antibody as reported herein for use in the treatment of prodromal Alzheimer's disease.

One aspect as reported herein is the (humanized) antibody as reported herein for use in the treatment of mild Alzheimer's disease.

One aspect as reported herein is the (humanized) antibody as reported herein for use in reducing Tau(pS422)-induced neurodegeneration.

One aspect as reported herein is the (humanized) antibody as reported herein for use in maintaining cognition and function.

One aspect as reported herein is the (humanized) antibody as reported herein for use in slowing the rate of cognitive and functional decline.

One aspect as reported herein is the (humanized) antibody as reported herein for use in slowing down the rate of neurofibrillary tangle accumulation.

In one embodiment of the previous aspects the use is by reducing neurofibrillary tangle burden by clearing Tau (pS422).

In one embodiment of the previous aspects the use is by preventing neurofibrillary tangle build up.

In one embodiment of the previous aspects the use is by removing/clearing neurofibrillary tangles.

In one embodiment the preventing and/or removing is by promoting the intracellular clearance of tau aggregates.

In one embodiment of the previous aspects the use is by inhibiting neurofibrillary tangle spreading. In one embodiment the inhibiting is by preventing interneuronal transfer of pathological tau forms/seeds.

Aspects of the current invention are also methods of treatment comprising administering the (humanized) antibody as reported herein for treating Alzheimer's disease, for treating prodromal Alzheimer's disease, for treating mild Alzheimer's disease, for reducing Tau(pS422)-induced neurodegeneration, for maintaining cognition and function, for slowing the rate of cognitive and functional decline, and/or for slowing down the rate of neurofibrillary tangle accumulation.

One aspect as reported herein is the use of the (humanized) antibody as reported herein in the manufacture of a medicament.

In one embodiment the medicament is for treatment of Alzheimer's disease.

In one embodiment the medicament is for treatment of prodromal Alzheimer's disease.

In one embodiment the medicament is for treatment of mild Alzheimer's disease.

In one embodiment the medicament is for reducing Tau (pS422)-induced neurodegeneration.

In one embodiment the medicament is for maintaining cognition and function.

In one embodiment the medicament is for slowing the rate of cognitive and functional decline.

One aspect as reported herein is a method of treating an individual having Alzheimer's disease comprising administering to the individual an effective amount of a (humanized) anti-human Tau(pS422) antibody as reported herein.

One aspect as reported herein is a method of reducing Tau(pS422)-induced neurodegeneration in an individual comprising administering to the individual an effective amount of a (humanized) anti-human Tau(pS422) antibody as reported herein to reduce Tau(pS422)-induced neurodegeneration.

One aspect as reported herein is a method of maintaining cognition and function in an individual comprising administering to the individual an effective amount of a (humanized) anti-human Tau(pS422) antibody as reported herein to maintain cognition and function.

One aspect as reported herein is a method of slowing the rate of cognitive and functional decline in an individual comprising administering to the individual an effective amount of a (humanized) anti-human Tau(pS422) antibody as reported herein to slow the rate of cognitive and functional decline.

One aspect as reported herein is the use of a (humanized) anti-human Tau(pS422) antibody as reported herein in the reduction of Tau(pS422)-induced neurodegeneration.

One aspect as reported herein is the use of a (humanized) anti-human Tau(pS422) antibody as reported herein in maintaining cognition and function.

One aspect as reported herein is the use of a (humanized) anti-human Tau(pS422) antibody as reported herein in slowing the rate of cognitive and functional decline.

The antibodies as reported herein can be used in the treatment of Alzheimer's disease.

With the (humanized) antibodies as reported herein inhibition/reduction of progression of Alzheimer's disease and neuropathology can be effected.

The (humanized) antibodies as reported herein can be used to protect an animal from the development of Alzheimer's disease or even used to stop the progression of Alzheimer's disease in an animal. In one embodiment the animal is a human.

In one embodiment the (humanized) antibody as reported herein binds to Tau(pS422) on brain sections of Tau(pS422) transgenic mice and Alzheimer's disease patients; and/or labels Tau(pS422) in Tau(pS422) transgenic cells.

The (humanized) antibodies as reported herein can be used for the treatment of Alzheimer's disease.

One aspect as reported herein is a (humanized) antibody that specifically binds to the amino acid sequence of SEQ ID NO: 03 in human Tau(pS422).

The (humanized) antibodies as reported herein specifically bind to/recognize early and late stage disease-relevant forms of human Tau(pS422).

One aspect as reported herein is the use of the (humanized) antibody as reported herein for the prevention of human Tau(pS422)-related Alzheimer's disease spread.

One aspect as reported herein is the use of the (humanized) antibody as reported herein for the reduction of lysosomal membrane disintegration.

One aspect as reported herein is the use of the (humanized) antibody as reported herein for the stabilization of lysosome membrane against human Tau(pS422)-induced destabilization and/or disintegration.

One aspect as reported herein is the use of the (humanized) antibody as reported herein for the prevention of Alzheimer's disease progression.

The (humanized) antibodies as reported herein function by antibody mediated inhibition of human Tau(pS422) seeding and spreading between cells.

The (humanized) antibodies as reported herein protect lysosomes from fibrillar damage by binding to human Tau (pS422).

BRIEF DESCRIPTION OF THE DRAWINGS

FIG. 3A-FIG. 3D show biochemical binding of different combinations of humanized VH and VL to (FIG. 3A) phosphorylated tau peptide, (FIG. 3B) phosphorylated full-length human tau, (FIG. 3C) non-phosphorylated tau peptide, (FIG. 3D) non-phosphorylated full-length human tau; (1)=VH00/VL00, (2)=VH32/VL21, (3)=VH20/VL22, (4)=VH32/VL22, (5)=VH33/VL22; coating concentrations: phosphorylated tau peptide: 50 ng/ml, all other targets: 1 μg/ml; (comparable results are obtained if phosphorylated tau peptide is coated with 1 μg/ml (data not shown)).

FIG. 4A-FIG. 4B show biochemical binding of different combinations of humanized VH and VL to (FIG. 4A)=full length human tau S422A mutant, (FIG. 4B)=aggregated human Tau(pS422); (1)=VH00/VL00, (2)=VH32/VL21, (3)=VH20/VL22, (4)=VH32/VL22, (5)=VH33/VL22; coating concentrations:phosphorylated tau peptide: 50 ng/ml, all other targets: 1 μg/ml; (comparable results are obtained if phosphorylated tau peptide is coated with 1 μg/ml (data not shown)).

FIG. 7A: x-axis: Tau(pS422) [ng/mg brain]; y-axis: 1: baseline, 2: vehicle, 3: anti-Tau(pS422) antibody (VH35H5/VL31A1) @ 1.7 mg/kg, 4: anti-Tau (pS422) antibody (VH35H5/VL31A1) @ 5 mg/kg, 5: anti-Tau(pS422) antibody (VH35H5/VL31A1) @ 15 mg/kg. FIG. 7B: x-axis: Tau(pS422) [ng/mg brain]; y-axis: 1: baseline, 2: vehicle, 3: anti-Tau(pS422) antibody (VH35H5/VL49G1) @ 1.7 mg/kg, 4: anti-Tau(pS422) antibody (VH35H5/VL49G1) @ 5 mg/kg, 5: anti-Tau(pS422) antibody (VH35H5/VL49G1) @ 15 mg/kg.

FIG. 8A:

x-axis: total tau [ng/mg brain]; y-axis: 1: baseline, 2: vehicle, 3: anti-Tau(pS422) antibody (VH35H5/VL49G1) @ 1.7 mg/kg, 4: anti-Tau(pS422) antibody (VH35H5/VL49G1) @ 5 mg/kg, 5: anti-Tau(pS422) antibody (VH35H5/VL49G1) @ 15 mg/kg. FIG. 8B: x-axis: total tau [ng/mg brain]; y-axis: 1: baseline, 2: vehicle, 3: anti-Tau (pS422) antibody (VH35H5/VL31A1) @ 1.7 mg/kg, 4: anti-Tau(pS422) antibody (VH35H5/VL31A1) @ 5 mg/kg, 5: anti-Tau(pS422) antibody (VH35H5/VL31A1) @ 15 mg/kg.

FIG. 9A: Cortex; x-axis: Tau(pS422) area occupancy [%]; y-axis: 1: baseline, 2: vehicle, 3: anti-Tau(pS422) antibody (VH35H5/VL31A1) @ 1.7 mg/kg, 4: anti-Tau(pS422) antibody (VH35H5/VL31A1) @ 5 mg/kg, 5: anti-Tau(pS422) antibody (VH35H5/VL31A1) @ 15 mg/kg. FIG. 9B: Hippocampus; x-axis: area occupancy [%]; y-axis: 1: baseline, 2: vehicle, 3: anti-Tau(pS422) antibody (VH35H5/VL31A1) @ 1.7 mg/kg, 4: anti-Tau(pS422) antibody (VH35H5/VL31A1) @ 5 mg/kg, 5: anti-Tau(pS422) antibody (VH35H5/VL31A1) @ 15 mg/kg.

BRIEF DESCRIPTION OF THE SEQUENCES

Figure 1:
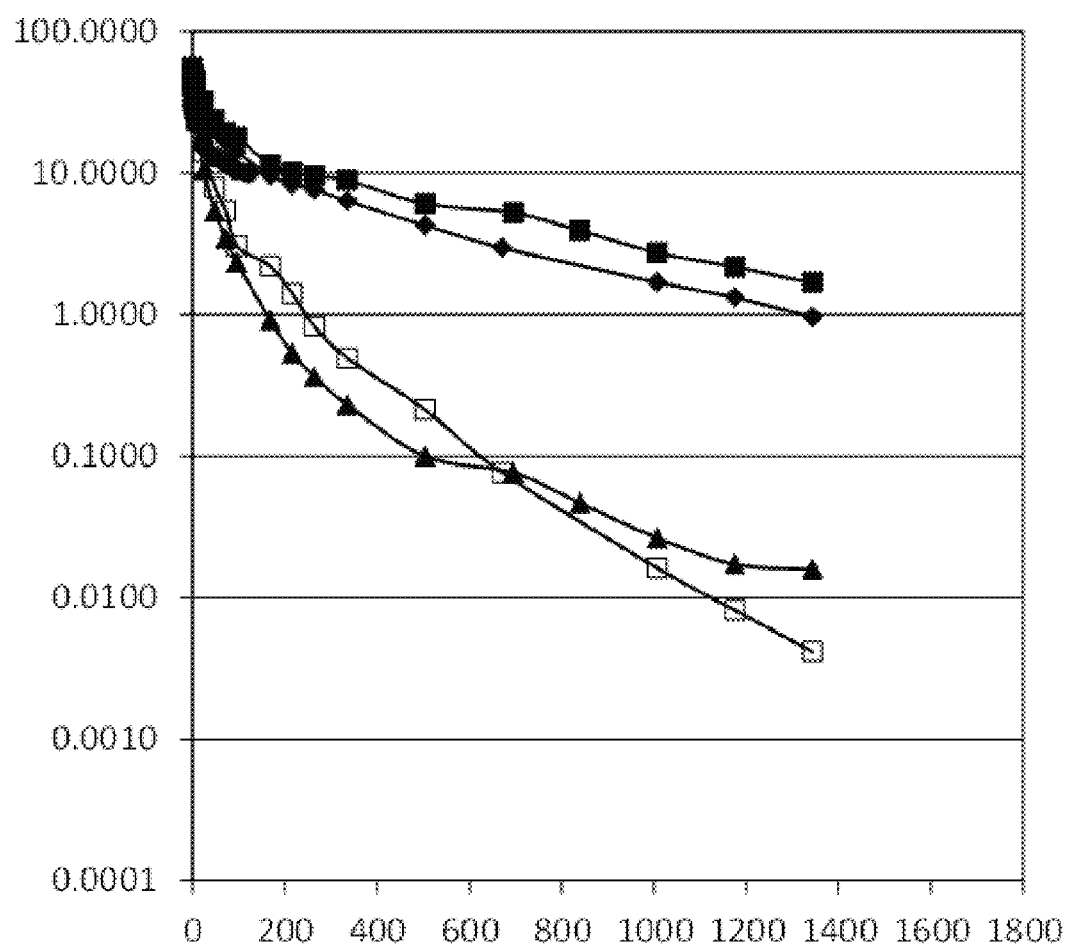
FIG. 1 shows the result of a pharmacokinetic study in cynomolgus; solid diamond: VH35H5/VL31A1; open square: VH35H5/VL35F2; solid square: VH76A6/VL35G4; solid triangle: VH32/VL22; solid circle: VH00/VL00; X-axis: time after dosing [h]; y-axis: Serum concentration, dose-norm. [(μg/mL)/(mg/kg)].
Figure 2:
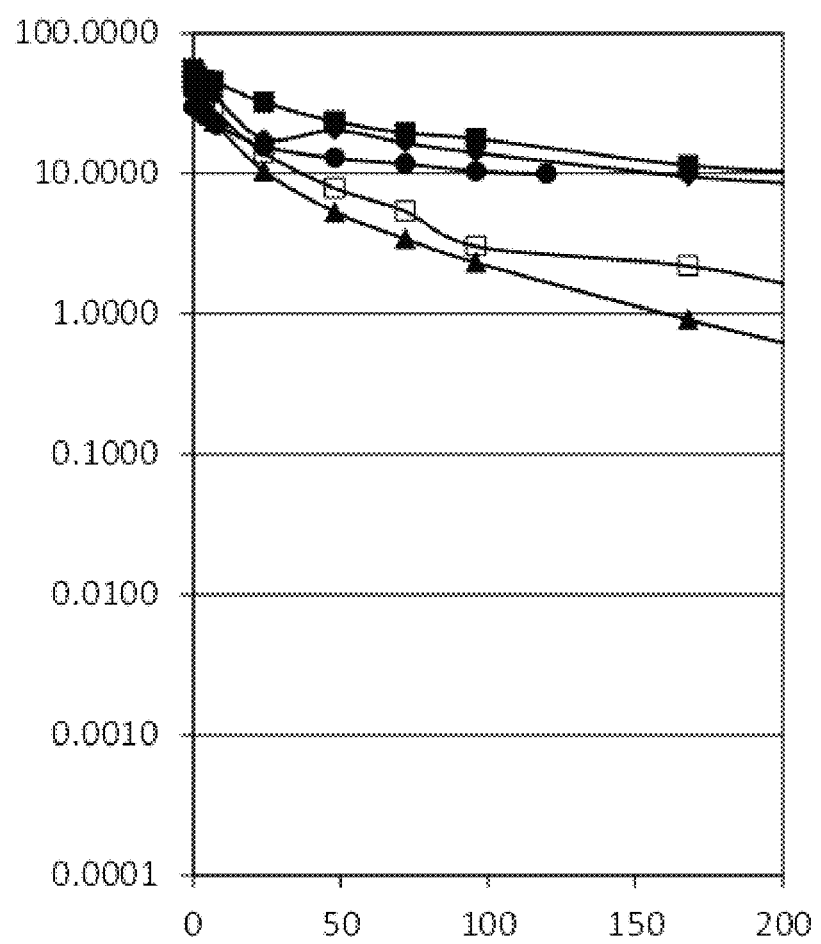
FIG. 2 shows the zoom to time range 0-200 h of FIG. 1.

SEQ ID NO: 01 human tau protein isoform F (441 residues)
SEQ ID NO: 02 human tau protein isoform F (441 residues) phosphorylated at the serine residue at position 422
SEQ ID NO: 03 fragment of human tau protein (residues 416 to 430 of SEQ ID NO: 01) with phosphorylated serine at position 7 (corresponding to position 422 of SEQ ID NO: 01): Ser-Ile-Asp-Met-Val-Asp-Ser(PO$_3$H$_2$)—Pro-Gln-Leu-Ala-Thr-Leu-Ala-Asp
SEQ ID NO: 04 rabbit antibody 086 CDRL1—QSSQSVRTNKLA
SEQ ID NO: 05 rabbit antibody 086 CDRL2—SASTLDF
SEQ ID NO: 06 rabbit antibody 086 CDRL3—LGYFDCSIADCVA
SEQ ID NO: 07 rabbit antibody 086 VL00
SEQ ID NO: 08 rabbit antibody 086 CDRH1—SNAIN
SEQ ID NO: 09 rabbit antibody 086 CDRH2—YIAVSGNTYYASWAKG
SEQ ID NO: 10 rabbit antibody 086 CDRH3—SNI
SEQ ID NO: 11 rabbit antibody 086 VH00
SEQ ID NO: 12 humanized CDRL1 variant 1—RSSQSVRTNKLA
SEQ ID NO: 13 humanized CDRL1 variant 2—RSSQSVRTNRLA
SEQ ID NO: 14 humanized CDRL2 variant 1—SASTLDY
SEQ ID NO: 15 humanized CDRL3 variant 1—LGYFDSSADIVA
SEQ ID NO: 16 humanized VL variant 1—VL21
SEQ ID NO: 17 humanized VL variant 2—VL22
SEQ ID NO: 18 humanized CDRH2—YIAVSGNTYYADSVKG
SEQ ID NO: 19 humanized VH variant 1—VH32
SEQ ID NO: 20 humanized VH variant 2—VH20
SEQ ID NO: 21 humanized VH variant 3—VH33
SEQ ID NO: 22 humanized CDRL2 variant 2—SASTLQS
SEQ ID NO: 23 humanized CDRL2 variant 3—SASTLES
SEQ ID NO: 24 humanized CDRL3 variant 2—LGYFDSSIADSVA
SEQ ID NO: 25 humanized CDRL3 variant 3—LGYFDSSIADRVA
SEQ ID NO: 26 humanized CDRL3 variant 4—LGYFDPSIADPVA
SEQ ID NO: 27 humanized CDRL3 variant 5—LGYFDSSIADIVA
SEQ ID NO: 28 humanized CDRL3 variant 6—LGYFDPSADPIA
SEQ ID NO: 29 humanized CDRL3 variant 7—LGYFDPSADPVA
SEQ ID NO: 30 humanized CDRL1 variant 3—RASQGVRTNKLA
SEQ ID NO: 31 humanized CDRL1 variant 4—RASQSVRTNKLA
SEQ ID NO: 32 humanized VL variant 4—VL01
SEQ ID NO: 33 humanized VL variant 5—VL09
SEQ ID NO: 34 humanized VL variant 6—VL12
SEQ ID NO: 35 humanized VL variant 7—VL15
SEQ ID NO: 36 humanized VL variant 8—VL16
SEQ ID NO: 37 humanized VL variant 9—VL17
SEQ ID NO: 38 humanized VL variant 10—VL19
SEQ ID NO: 39 humanized VL variant 11—VL28
SEQ ID NO: 40 humanized VL variant 12—VL33
SEQ ID NO: 41 humanized VL variant 13—VL35
SEQ ID NO: 42 humanized VL variant 14—VL39
SEQ ID NO: 43 humanized VL variant 15—VL40
SEQ ID NO: 44 humanized VL variant 16—VL41
SEQ ID NO: 45 humanized VL variant 17—VL42
SEQ ID NO: 46 humanized VH variant 4—VH01
SEQ ID NO: 47 humanized VH variant 5—VH02
SEQ ID NO: 48 humanized VH variant 6—VH03
SEQ ID NO: 49 humanized VH variant 7—VH04
SEQ ID NO: 50 humanized VH variant 8—VH14
SEQ ID NO: 51 humanized VH variant 9—VH15
SEQ ID NO: 52 humanized VH variant 10—VH18
SEQ ID NO: 53 humanized VH variant 11—VH19
SEQ ID NO: 54 humanized VH variant 12—VH22
SEQ ID NO: 55 humanized VH variant 13—VH23
SEQ ID NO: 56 humanized VH variant 14—VH24
SEQ ID NO: 57 humanized VH variant 15—VH31
SEQ ID NO: 65 humanized VH variant 16—VH35H5
SEQ ID NO: 66 humanized VL variant 18—VL31A1
SEQ ID NO: 67 humanized VL variant 19—VL49G1
SEQ ID NO: 68 humanized VL variant 20—VL35F2
SEQ ID NO: 69 humanized VL variant 21—VL53A2
SEQ ID NO: 70 humanized CDRL1 variant 5
SEQ ID NO: 71 humanized CDRL1 variant 6
SEQ ID NO: 72 humanized CDRL2 variant 4
SEQ ID NO: 73 humanized CDRL2 variant 5
SEQ ID NO: 74 humanized CDRL3 variant 8
SEQ ID NO: 75 humanized CDRL3 variant 9
SEQ ID NO: 76 humanized VH variant 17—VH76A6
SEQ ID NO: 77 humanized CDRH1 variant 1
SEQ ID NO: 78 humanized VL variant 22—VL35G4
SEQ ID NO: 79 humanized CDRL3 variant 10
SEQ ID NO: 80 humanized VL variant 23—VL145B12
SEQ ID NO: 81 humanized CDRL2 variant 6
SEQ ID NO: 82 anti-transferrin receptor antibody heavy chain 1
SEQ ID NO: 83 anti-transferrin receptor antibody heavy chain 2
SEQ ID NO: 84 anti-transferrin receptor antibody heavy chain 3
SEQ ID NO: 85 anti-transferrin receptor antibody light chain
SEQ ID NO: 86 humanized VL variant 24—VL4G1
SEQ ID NO: 87 humanized CDRL3 variant 11

Sequence correspondence table:

| variable domain | CDR1 | CDR2 | CDR3 | complete sequence |
|---|---|---|---|---|
| VL00 | 04 | 05 | 06 | 07 |
| VL01 | 04 | 05 | 06 | 32 |
| VL4G1 | 12 | 05 | 87 | 86 |
| VL09 | 31 | 23 | 06 | 33 |
| VL12 | 30 | 22 | 06 | 34 |
| VL15 | 30 | 22 | 24 | 35 |
| VL16 | 30 | 22 | 25 | 36 |
| VL17 | 12 | 05 | 06 | 37 |
| VL19 | 12 | 05 | 06 | 38 |
| VL21 | 12 | 05 | 15 | 16 |
| VL22 | 13 | 14 | 15 | 17 |
| VL28 | 13 | 05 | 29 | 39 |
| VL31A1 | 70 | 72 | 15 | 66 |
| VL33 | 13 | 05 | 27 | 40 |
| VL35 | 13 | 05 | 27 | 41 |
| VL35F2 | 12 | 14 | 74 | 68 |
| VL35G4 | 12 | 14 | 79 | 78 |
| VL39 | 13 | 05 | 26 | 42 |
| VL40 | 13 | 05 | 29 | 43 |
| VL41 | 13 | 05 | 28 | 44 |
| VL42 | 13 | 05 | 28 | 45 |
| VL49G1 | 71 | 73 | 15 | 67 |
| VL53A2 | 12 | 14 | 75 | 69 |
| VL145B12 | 71 | 81 | 15 | 80 |
| VH00 | 08 | 09 | 10 | 11 |
| VH01 | 08 | 09 | 10 | 46 |
| VH02 | 08 | 09 | 10 | 47 |
| VH03 | 08 | 09 | 10 | 48 |
| VH04 | 08 | 09 | 10 | 49 |
| VH14 | 08 | 09 | 10 | 50 |
| VH15 | 08 | 09 | 10 | 51 |
| VH18 | 08 | 18 | 10 | 52 |
| VH19 | 08 | 18 | 10 | 53 |
| VH20 | 08 | 18 | 10 | 20 |
| VH22 | 08 | 18 | 10 | 54 |
| VH23 | 08 | 18 | 10 | 55 |
| VH24 | 08 | 18 | 10 | 56 |
| VH31 | 08 | 09 | 10 | 57 |
| VH32 | 08 | 09 | 10 | 19 |
| VH33 | 08 | 09 | 10 | 21 |
| VH35H5 | 8 | 9 | 10 | 65 |
| VH76A6 | 8 | 77 | 10 | 76 |

DETAILED DESCRIPTION OF THE INVENTION

The present invention relates to a binding peptide or protein or a functional part thereof, particularly to an antibody, particularly a monoclonal antibody or a functional part thereof, particularly a binding peptide or antibody, which binding peptide or antibody recognizes and specifically binds to a phospho-epitope on a mammalian, particularly on the human tau protein or on a fragment thereof, particularly to a pathological protein tau conformer, but, in one embodiment, does not bind to the corresponding unphosphorylated epitope and/or to non-related epitopes wherein said binding peptide or antibody binds to an epitope on a mammalian, particularly on the human tau protein as shown in SEQ ID NO: 02, consisting of tau amino acid residues 416-430 comprising a phosphorylated Ser at position 422 (pS422).

I. DEFINITIONS

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-human Tau(pS422) antibody" and "an antibody that specifically binds to human Tau(pS422)" refer to an antibody that is capable of binding human Tau(pS422) with sufficient affinity such that the antibody is useful as a diagnostic and/or therapeutic agent in targeting human Tau (pS422). In one embodiment, the extent of binding of an anti-human Tau(pS422) antibody to an unrelated, non-human Tau(pS422) protein is less than about 10% of the binding of the antibody to human Tau(pS422) as measured, e.g., by a radioimmunoassay (RIA).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. In one embodiment an antibody binding to the same epitope as a reference antibody blocks binding of the reference antibody to its antigen by 50% or more. In one embodiment an antibody binding to the same epitope as a reference antibody blocks binding of the reference antibody to its antigen by 80% or more. In one embodiment an antibody binding to the same epitope as a reference antibody blocks binding of the reference antibody to its antigen by 90% or more. In one embodiment an antibody binding to the same epitope as a reference antibody blocks binding of the reference antibody to its antigen by 95% or more. In one preferred embodiment an antibody binding to the same epitope as a reference antibody has binding interactions with the same residues as the reference antibody on the antigen.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgA_1$, and $IgA_2$. The heavy chain constant domains that correspond to the different classes of immunoglobulins are called α, δ, ε, γ, and μ, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

The terms "full length antibody", "intact antibody", and "whole antibody" are used herein interchangeably to refer to an antibody having a structure substantially similar to a native antibody structure or having heavy chains that contain an Fc-region as defined herein. The term "full length antibody" denotes a multimeric polypeptide consisting of two antibody light chain polypeptides and two antibody heavy chain polypeptides linked by disulfide bonds wherein in the two antibody heavy chain polypeptides the C-terminal lysine residue (K) can be present or not.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include:
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "immunoconjugate" is an antibody conjugated to one or more heterologous molecule(s).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human Tau (pS422) antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (x) and lambda (k), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "human Tau(pS422)", as used herein, refers to native human Tau(pS422) (UniProt P37840). The term encompasses "full-length", unprocessed human Tau(pS422) as well as any form of human Tau(pS422) that results from processing in the cell. The term also encompasses naturally occurring variants of human Tau(pS422), e.g., mutants, splice variants or allelic variants. The amino acid sequence of human Tau(pS422) is shown in SEQ ID NO: 02.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. COMPOSITIONS AND METHODS

A. Exemplary Humanized Anti-Human Tau(pS422) Antibodies

The humanized antibodies as reported herein were not available by standard humanization methods. It was required to introduce non-standard mutations in the amino acid sequence in order to obtain a humanized antibody with comparable binding characteristics and pharmacokinetic properties as the parent rabbit antibody. This is especially important as the antibodies as reported herein are intended to cross the human blood-brain-barrier and to be effective within the human brain. Thus, the generally applied criteria for the selection of humanized antibodies were not sufficiently stringent in order to be applied directly in the current case.

It has been found that in order to obtain a suitable and developable humanized antibody two cysteines forming a disulfide-bridge in the CDRL3 (light chain CDR3) had to be replaced by serine and isoleucine, respectively. In addition, to ensure proper orientation of the same CDRL3 an isoleucine residue present in the middle of the rabbit CDRL3 was deleted resulting in a humanized CDRL3 that is one amino acid residue smaller than the parent rabbit CDRL3.

It has also been found that to maintain in vivo pharmacokinetic properties the amino acid residue at position 32 in the light chain should be a lysine (numbering according to Kabat). The removal of the disulfide bridge in the light chain HVR-L3 does not have an impact on the kinetic behavior in vivo.

It has further been found that it is advantageous to maintain three valine amino acid residues in the heavy chain at positions 4, 24 and 78 (numbering according to Kabat). Without being bound by this theory it is assumed that these residues are required to ensure proper presentation of the antigen binding loops of the heavy chain variable region. Additionally the presence of an arginine residue at position 71 in the heavy chain variable domain is advantageous (numbering according to Kabat).

The HVR-L3 comprises two aspartic acid residues which might be a deamidation hotspot, especially during prolonged storage. In the light chain variable domain variant VL35G4 one of these two aspartic acid residues has been changed.

All numbering as used herein is based on the Kabat variable domain numbering scheme.

In the following Table characteristics of the different humanized variants of the rabbit light chain variable domain in combination with the humanized heavy chain variable domains VH14 and VH20, respectively, are shown. The binding partner was human Tau(pS422).

| | ka [1/Ms] | kd [1/s] | KD [M] | t/2 diss [min] | T [° C.] |
|---|---|---|---|---|---|
| VH14 with | | | | | |
| VL00 | | 1.04E-03 | | 11 | 25 |
| VL01 | | 3.82E-03 | | 3 | 25 |
| VL09 | | 2.35E-03 | | 5 | 25 |
| VL12 | | 2.48E-03 | | 5 | 25 |
| VL15 | | 3.63E-03 | | 3 | 25 |
| VL16 | | n.d. | | | |
| VL17 | | 2.39E-03 | | 5 | 25 |
| VL17 | | 3.03E-03 | | 4 | 25 |
| VL19 | | 1.98E-03 | | 6 | 25 |
| VL21 | | 2.93E-03 | | 4 | 25 |
| VL22 | | 3.30E-03 | | 4 | 25 |
| VL28 | | 3.84E-03 | | 3 | 25 |
| VL33 | | 1.02E-02 | | 1 | 25 |
| VL35 | | 1.10E-02 | | 1 | 25 |
| VL39 | | 5.22E-03 | | 2 | 25 |
| VL40 | | 3.01E-03 | | 4 | 25 |
| VL41 | | n.d. | | | |
| VL42 | | n.d. | | | |
| VH20 with | | | | | |
| VL00 | | n.d. | | | |
| VL01 | | n.d. | | | |
| VL09 | | 2.14E-03 | | 5 | 25 |
| VL12 | | n.d. | | | |
| VL15 | | n.d. | | | |
| VL16 | | n.d. | | | |
| VL17 | | 5.35E-04 | | 22 | 25 |
| VL19 | | 3.66E-04 | | 32 | 25 |
| VL19 | 1.94E+04 | 1.13E-03 | 5.84E-8 | 10.2 | 37 |
| VL21 | | 7.88E-04 | | 15 | 25 |
| VL21 | 3.03E+04 | 2.10E-03 | 6.95E-08 | 5.5 | 37 |
| VL22 | | 8.39E-04 | | 14 | 25 |
| VL22 | 3.44E+04 | 2.37E-03 | 6.90E-08 | 4.9 | 37 |
| VL28 | | 1.27E-03 | | 9 | 25 |
| VL28 | 2.50E+04 | 3.61E-03 | 1.45E-07 | 3.2 | 37 |
| VL33 | | 1.61E-03 | | 7 | 25 |
| VL35 | | 1.59E-03 | | 7 | 25 |
| VL39 | | 1.91E-03 | | 6 | 25 |
| VL40 | | 9.98E-04 | | 12 | 25 |
| VL41 | | 4.29E-03 | | 3 | 25 |
| VL42 | | 4.57E-03 | | 3 | 25 |

Reference values VH00 with VL00 (rabbit antibody):

25° C.: kd=2.6E-04; t/2=44 minutes

37° C.: ka=3.7E+04, kd=5.25E-03, KD=1.4E-08, t/2=22 minutes

In the following Table characteristics of the different humanized variants of the rabbit light chain variable domain in combination with the humanized light chain variable domains VL17 and VL19, respectively, are shown.

|  | ka [1/Ms] | kd [1/s] | KD [M] | t/2 diss [min] | T [° C.] |
|---|---|---|---|---|---|
| VL17 with |  |  |  |  |  |
| VH00 |  | 4.98E−04 |  | 23 | 25 |
| VH01 |  | 2.3E−03 |  | 5 | 25 |
| VH02 |  | 3.71E−03 |  | 3 | 25 |
| VH03 |  | 3.93E−03 |  | 3 | 25 |
| VH04 |  | 4.16E−03 |  | 3 | 25 |
| VH14 |  | 3.0E−03 |  | 4 | 25 |
| VH15 |  | 3.26E−03 |  | 4 | 25 |
| VH18 |  | 2.3E−03 |  | 5 | 25 |
| VH19 |  | n.d. |  |  |  |
| VH20 |  | 5.4E−04 |  | 22 | 25 |
| VH22 |  | 2.0E−03 |  | 6 | 25 |
| VH23 |  | 7.0E−04 |  | 17 | 25 |
| VH24 |  | 7.9E−04 |  | 15 | 25 |
| VH31 |  | n.d. |  |  |  |
| VH32 |  | n.d. |  |  |  |
| VH33 |  | n.d. |  |  |  |

Reference values VH00 with VL00 (rabbit antibody):

25° C.: kd=2.6E-04; t/2=44 minutes

37° C.: ka=3.7E+04, kd=5.25E-03, KD=1.4E-08, t/2=22 minutes

In the following Table the kinetic constants for different VH/VL combinations are shown (determined according to Example 8).

| VH/VL combination | KD 25° C. [nM] | t/2diss 25° C. [min] | MR | KD 37° C. [nM] | t/2diss 37° C. [min] | MR |
|---|---|---|---|---|---|---|
| VH00/VL00 | 8 | 54 | 0.6 | 12 | 24 | 0.8 |
| VH20/VL22 | 37 | 16 | 0.4 | 68 | 5 | 0.5 |
| VH32/VL21 | 18 | 26 | 0.5 | 32 | 9 | 0.6 |
| VH32/VL22 | 14 | 29 | 0.5 | 31 | 8 | 0.6 |
| VH33/VL22 | 20 | 25 | 0.4 | 39 | 8 | 0.5 |

The biochemical binding of different combinations of humanized VH and VL is shown in FIG. 3A-FIG. 3D and FIG. 4A-FIG. 4B.

In the following Table the binding specificity for different VH/VL combinations are shown ($EC_{50}$ values in [ng/ml]).

| VH/VL combination | Tau(pS422) fragment SEQ ID NO: 03 | full length Tau(pS422) SEQ ID NO: 02 | Tau(pS422) aggregates | full length tau SEQ ID NO: 01 | tau peptide residues 416 to 430 of SEQ ID NO: 01 | microtubuli associated tau | S422A tau mutant S422A SEQ ID NO: 01 |
|---|---|---|---|---|---|---|---|
| VH00/VL00 | 6.3 | 5.2 | 18.1 | no binding | >1000 | no binding | 47.9 |
| VH20/VL22 | 4.8 | 4.0 | 27.2 | no binding | >1000 | no binding | 110.6 |
| VH32/VL21 | 4.4 | 2.9 | 9.4 | no binding | 634 | no binding | 21.5 |
| VH32/VL22 | 5.6 | 3.5 | 8.3 | no binding | 48 | no binding | 17.4 |
| VH33/VL22 | 5.6 | 3.8 | 13.5 | no binding | 120 | no binding | 34.5 |

-continued

|  | ka [1/Ms] | kd [1/s] | KD [M] | t/2 diss [min] | T [° C.] |
|---|---|---|---|---|---|
| VL19 with |  |  |  |  |  |
| VH00 |  | n.d. |  |  |  |
| VH01 |  | 1.9E−03 |  | 6 | 25 |
| VH02 |  | n.d. |  |  |  |
| VH03 |  | n.d. |  |  |  |
| VH04 |  | n.d. |  |  |  |
| VH14 |  | 2.0E−03 |  | 6 | 25 |
| VH15 |  | n.d. |  |  |  |
| VH18 |  | 1.9E−03 |  | 6 | 25 |
| VH19 |  | 2.0E−03 |  | 6 | 25 |
| VH20 |  | 3.7E−04 |  | 32 | 25 |
| VH20 | 1.94E+04 | 1.13E−03 | 5.84E−08 | 10.2 | 37 |
| VH22 |  | 2.1E−03 |  | 6 | 25 |
| VH23 |  | 5.7E−04 |  | 20 | 25 |
| VH24 |  | 6.3E−04 |  | 18 | 25 |
| VH31 |  | n.d. |  |  |  |
| VH32 |  | n.d. |  |  |  |
| VH33 |  | n.d. |  |  |  |

Figure 5:
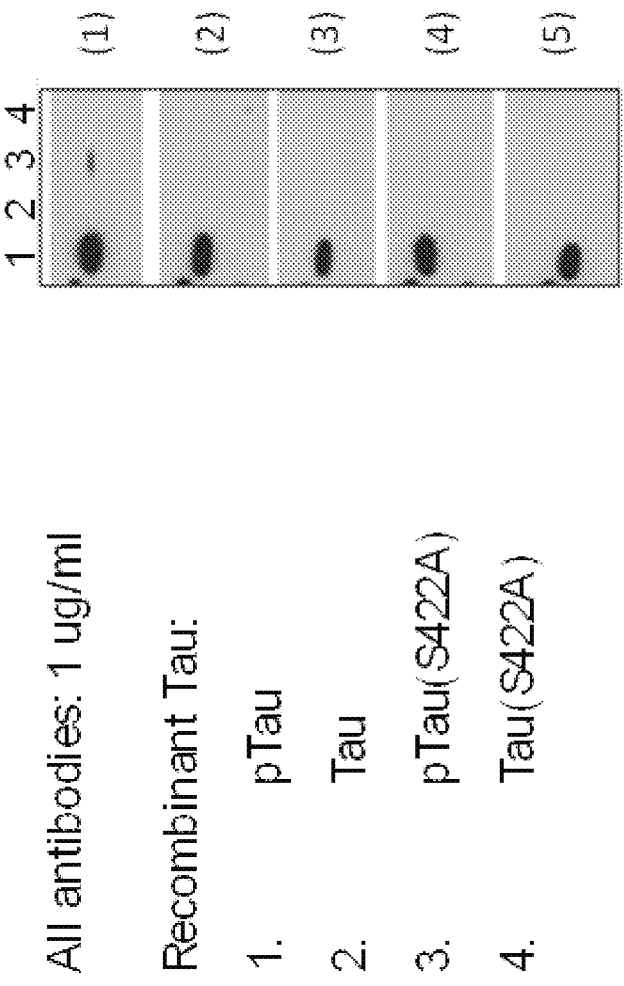
FIG. 5 is a Western Blot showing the selectivity of selected humanized VH/VL combinations; (1)=VH00/VL00, (2)=VH32/VL21, (3)=VH20/VL22, (4)=VH32/VL22, (5)=VH33/VL22.

The sensitivity of selected humanized VH/VL combinations to the human tau mutant S422A can be seen from the Western Blots shown in FIG. 5. All humanized variants selectively bind to human tau phosphorylated at S422. There is low level cross-reactivity to non-S422 phosphoepitopes of the parent rabbit antibody but the humanized variants shown are less cross-reactive in this respect than the parental rabbit antibody.

Figure 6:
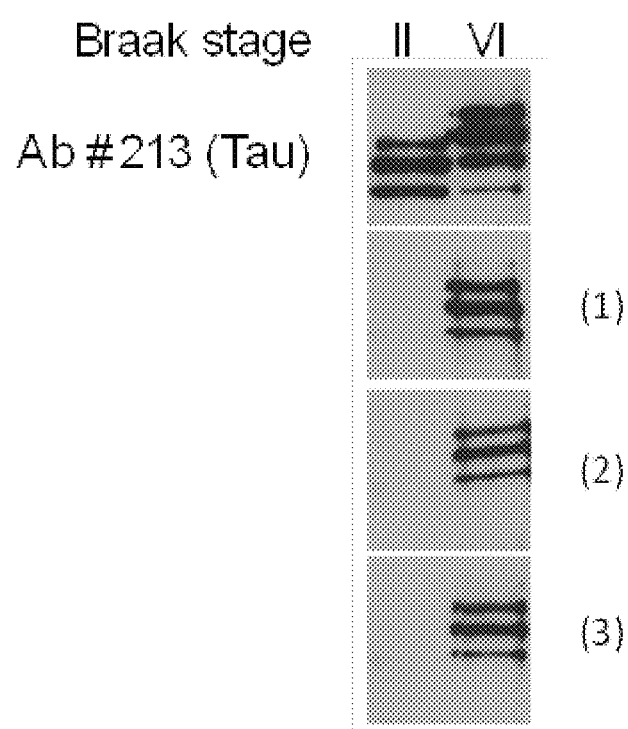
FIG. 6 shows binding to hyperphosphorylated tau in brain extracts of Alzheimer's disease patients; (1)=VH00/VL00, (2)=VH32/VL21, (3)=VH32/VL22.

In FIG. 6 the binding to PHF-tau in brain extracts of Alzheimer's disease patients for the parental rabbit antibody and for selected humanized anti-human Tau(pS422) antibodies is shown.

Based on the above, the combination of VH32/VL22 was chosen as humanized antibody.

The following average clearance rates in cynomolgus have been found with the parental VH/VL combination and the humanized VH/VL combination (normal clearance for human IgG is 0.18-0.36 ml/hr/kg).

| VH/VL combination | average clearance @ 1 mg/kg [ml/hr/kg] | average clearance @ 10 mg/kg [ml/hr/kg] |
|---|---|---|
| VH00/VL00 | 0.15 | n.d. |
| VH32/VL22 | 1.03 | 2.5 | n.d. = not determined

It can be seen that the VH32/VL22 combination has an increased clearance rate that is dose dependent.

In the following Table the kinetic constants for further VH/VL combinations generated to address the increased, dose-dependent clearance rate of VH32/VL22 with Tau (pS422) fragment are shown (determined according to Example 10).

| VH/VL combination | ka [1/Ms] | kd [1/s] | KD [nM] |
|---|---|---|---|
| VH35H5/VL31A1 | 3.80E+05 | 6.16E-04 | 1.62 nM |
| VH35H5/VL35F2 | 1.40E+05 | 3.21E-04 | 2.29 nM |
| VH35H5/VL49G1 | 3.12E+05 | 6.24E-04 | 2.00 nM |
| VH76A6/VL145B12 | 2.40E+05 | 6.28E-04 | 2.61 nM |
| VH00/VL00 | 1.35E+05 | 2.65E-04 | 1.96 nM |
| VH32/VL35G4 | 1.03E+05 | 2.31E-04 | 2.25 nM |
| VH76A6/VL35G4 | 1.12E+05 | 8.65E-05 | 0.77 nM |

In the following Table the kinetic constants for VH/VL combinations as Fab fragment with full length Tau(pS422) and Tau(pS422) fragment are shown (determined according to Example 11 and Example 12).

| VH/VL combination | Tau(pS422) fragment | | | full length Tau(pS422) | | |
|---|---|---|---|---|---|---|
| | ka [1/Ms] | kd [1/s] | KD [nM] | ka [1/Ms] | kd [1/s] | KD [nM] |
| VH32/VL22 | 4.79E+05 | 2.76E-04 | 0.6 | 8.42E+05 | 4.23E-04 | 0.5 |
| VH35H5/VL31A1 | 4.10E+05 | 1.43E-04 | 0.3 | 6.68E+05 | 2.26E-04 | 0.3 |
| VH35H5/VL49G1 | 4.23E+05 | 6.03E-05 | 0.1 | 7.46E+05 | 9.38E-05 | 0.1 |

In the following Table the binding specificity for different VH/VL combinations determined by ELISA are shown (selectivity for phosphorylated versus non-phosphorylated tau).

| VH/VL combination | full length Tau(pS422) SEQ ID NO: 02 $EC_{50}$ [ng/ml] | Tau(pS422) fragment SEQ ID NO: 03 $EC_{50}$ [ng/ml] | Tau(pS422) aggregates $EC_{50}$ [ng/ml] | full length tau SEQ ID NO: 01 OD@1 µg/mL | tau peptide 416 to 430 of SEQ ID NO: 01 OD@1 µg/mL |
|---|---|---|---|---|---|
| VH00/VL00 | 26.2 | 40.0 | 62.9 | 0.04 | 0.54 |
| VH32/VL22 | 21.9 | 40.4 | 31.1 | 0.14 | 2.26 |
| VH35H5/VL31A1 | 21.1 | 33.0 | 36.6 | 0.04 | 1.03 |
| VH35H5/VL35F2 | 28.0 | 45.2 | 57.0 | 0.04 | 1.31 |
| VH35H5/VL49G1 | 20.4 | 34.0 | 30.6 | 0.04 | 1.42 |
| VH32/VL4G1 | 16.8 | 27.3 | 27.0 | 0.04 | 1.13 |
| VH76A6/VL145B12 | 23.8 | 40.3 | 39.0 | 0.04 | 0.44 |
| VH32/VL35G4 | 26.1 | 43.8 | 78.6 | 0.04 | 0.07 |
| VH76A6/VL35G4 | 23.3 | 33.4 | 79.6 | 0.04 | 0.07 |

The following average clearance rates in cynomolgus have been found with different VH/VL combinations (normal clearance for human IgG is 0.18-0.36 ml/hr/kg; n.d.=not determined).

| VH/VL combination | average clearance @ 1 mg/kg [ml/hr/kg] | average clearance @ 10 mg/kg [ml/hr/kg] | average clearance @ 25 mg/kg [ml/hr/kg] |
|---|---|---|---|
| VH00/VL00 | 0.15 | n.d. | n.d. |
| VH32/VL22 | 1.03 | 2.5 | n.d. |
| VH35H5/VL31A1 | 0.14 | 0.19 | 0.24 |
| VH35H5/VL35F2 | 0.62 | n.d. | n.d. |
| VH35H5/VL49G1 | 0.63 | n.d. | n.d. |
| VH76A6/VL35G4 | 0.10 | n.d. | n.d. |

The following average clearance rates in mouse have been found with different VH/VL combinations (normal clearance for human IgG is 0.18-0.36 ml/hr/kg).

| VH/VL combination | average clearance @ 5 mg/kg [ml/hr/kg] | average clearance @ 25 mg/kg [ml/hr/kg] | average clearance @ 50 mg/kg [ml/hr/kg] |
|---|---|---|---|
| VH00/VL00 | 0.17 | 0.21 | n.d. |
| VH32/VL22 | 0.27 | n.d. | 1.31 |
| VH35H5/VL31A1 | 0.20 | 0.29 | n.d. |
| VH35H5/VL35F2 | 0.18 | 0.30 | n.d. |
| VH35H5/VL49G1 | 0.28 | 0.58 | n.d. |
| VH76A6/VL35G4 | 0.19 | 0.52 | n.d. |

In one embodiment of all aspects as reported herein the humanized anti-human Tau(pS422) antibody has an average clearance rate after intraveneous application of less than 0.6 ml/hr/kg at a dose of up to 25 mg/kg. In one embodiment the average clearance rate is 0.3 ml/hr/kg or less at a dose of up to 25 mg/kg.

In one preferred aspect, the invention provides a (humanized) anti-human Tau(pS422) antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 71; (e) HVR-L2 comprising the amino acid sequence of SEQ ID NO: 73; and (f) HVR-L3 comprising the amino acid sequence of SEQ ID NO: 15.

In one preferred aspect, the invention provides a (humanized) anti-human Tau(pS422) antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 70; (e) HVR-L2 comprising the amino acid sequence of SEQ ID NO: 72; and (f) HVR-L3 comprising the amino acid sequence of SEQ ID NO: 15.

In one preferred aspect, the invention provides a (humanized) anti-human Tau(pS422) antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 14; and (f) HVR-L3 comprising the amino acid sequence of SEQ ID NO: 74.

In one preferred aspect, the invention provides a (humanized) anti-human Tau(pS422) antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 77; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 14; and (f) HVR-L3 comprising the amino acid sequence of SEQ ID NO: 75.

In one aspect, the invention provides a (humanized) anti-human Tau(pS422) antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 14; and (f) HVR-L3 comprising the amino acid sequence of SEQ ID NO: 79.

In one aspect, the invention provides a (humanized) antibody comprising at least one, at least two, or all three VH HVR sequences selected from (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 10.

In one embodiment, the antibody comprises (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 10.

In another embodiment the antibody further comprises at least one, at least two, or all three VL HVR sequences selected from
i) (a) HVR-L1 comprising the amino acid sequence of SEQ ID NO: 71; (b) HVR-L2 comprising the amino acid sequence of SEQ ID NO: 73; and (c) HVR-L3 comprising the amino acid sequence of SEQ ID NO: 15; or
ii) (a) HVR-L1 comprising the amino acid sequence of SEQ ID NO: 70; (b) HVR-L2 comprising the amino acid sequence of SEQ ID NO: 72; and (c) HVR-L3 comprising the amino acid sequence of SEQ ID NO: 15; or
iii) (a) HVR-L1 comprising the amino acid sequence of SEQ ID NO: 12; (b) HVR-L2 comprising the amino acid sequence of SEQ ID NO: 14; and (c) HVR-L3 comprising the amino acid sequence of SEQ ID NO: 79.

In a further embodiment, the antibody comprises
i) (a) HVR-L1 comprising the amino acid sequence of SEQ ID NO: 71; (b) HVR-L2 comprising the amino acid sequence of SEQ ID NO: 73; and (c) HVR-L3 comprising the amino acid sequence of SEQ ID NO: 15; or
ii) (a) HVR-L1 comprising the amino acid sequence of SEQ ID NO: 70; (b) HVR-L2 comprising the amino acid sequence of SEQ ID NO: 72; and (c) HVR-L3 comprising the amino acid sequence of SEQ ID NO: 15; or
iii) (a) HVR-L1 comprising the amino acid sequence of SEQ ID NO: 12; (b) HVR-L2 comprising the amino acid sequence of SEQ ID NO: 14; and (c) HVR-L3 comprising the amino acid sequence of SEQ ID NO: 79.

In one aspect, the invention provides a (humanized) antibody comprising
i) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 71; (e) HVR-L2 comprising the amino acid sequence of SEQ ID NO: 73; and (f) HVR-L3 comprising the amino acid sequence of SEQ ID NO: 15, or
ii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 70; (e) HVR-L2 comprising the amino acid sequence of SEQ ID NO: 72; and (f) HVR-L3 comprising the amino acid sequence of SEQ ID NO: 15, or
iii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 14; and (f) HVR-L3 comprising the amino acid sequence of SEQ ID NO: 79.

In another embodiment the VH or VL contains substitutions (e.g., conservative substitutions), insertions, or deletions relative to the reference sequence, but an anti-human Tau(pS422) antibody comprising that sequence retains the ability to bind to human Tau(pS422).

In a further aspect of the invention, an anti-human Tau (pS422) antibody according to any of the above embodiments is a monoclonal antibody, including a chimeric, humanized or human antibody. In one embodiment, an anti-human Tau(pS422) antibody is an antibody fragment, e.g., a Fv, Fab, Fab', scFv, diabody, or F(ab')$_2$ fragment. In another embodiment, the antibody is a full length antibody, e.g., an intact IgG1 or IgG 4 antibody or other antibody class or isotype as defined herein.

The (humanized) antibody as reported herein reduces Tau(pS422) levels in the brain of transgenic TauPS2APP mice.

In a further aspect, a (humanized) anti-human Tau(pS422) antibody according to any of the above embodiments may incorporate any of the features, singly or in combination, as described in Sections 1-7 below:

1. Antibody Affinity

In certain embodiments, an antibody provided herein has a dissociation constant (KD) of <100 nM, <50 nM, or between 1 nM and 100 nM (e.g., $10^{-7}$M or less, e.g., from $10^{-7}$M to $10^{-9}$M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM ($^{125}$I)-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN 20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN 20®) surfactant (PBST) at 25° C. at a flow rate of approximately 25 μl/minute. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. No. 5,571,894 and U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Humanized Antibodies

Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of or a full length human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. No. 5,821,337, U.S. Pat. No. 7,527,791, U.S. Pat. No. 6,982,321, and U.S. Pat. No. 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for human Tau(pS422) and the other is for any other antigen. In certain embodiments, bispecific antibodies may bind to two different epitopes of human Tau(pS422). Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g., Gruber, M et al., J. Immunol. 152 (1994) 5368-5374); and preparing trispecific antibodies as described, e.g., in Tutt, A. et al., J. Immunol. 147 (1991) 60-69). Engineered antibodies with three or more functional antigen binding sites, including "Octopus antibodies," are also included herein (see, e.g., US 2006/0025576).

The antibody or fragment herein also includes a "Dual Acting Fab" or "DAF" comprising an antigen binding site that binds to human Tau(pS422) as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion and Deletion Variants

In certain embodiments, antibody variants having one or more amino acid substitutions are provided. Sites of interest for substitutional mutagenesis include the HVRs and FRs. Conservative substitutions are shown in the following Table under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g., a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g., Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc-region mutants include Fc-region mutants with substitutions at two or more of amino acid positions 265, 269, 270, 297 and 327, including the so-called "DANA"

Fc-region mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In some embodiments, alterations are made in the Fc-region that result in altered (i.e., diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. No. 5,648,260; U.S. Pat. No. 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-human Tau(pS422) antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an anti-human Tau(pS422) antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human Tau(pS422) antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-human Tau(pS422) antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, alphaLISA, Western blot, antibody or reverse phase array, etc.

In an exemplary ELISA or alphaLISA assay, Tau(pS422) in solution (e.g., in cell supernatant, cell or tissue lysates, body fluids, etc.) is bound by a capture antibody, which specifically binds to a first epitope on Tau(pS422), or Tau(pS422) in a certain conformation and a detection antibody coupled to a detection entity, which specifically binds to a second epitope or conformation of Tau(pS422). The readout is based on the detection entity (chemiluminescence, fluorescence, energy transfer induced luminescence, etc.). In some instances the same antibody can be used in the same assay as capture and detection antibody to detect aggregated forms of Tau(pS422) (see e.g., Tokuda, T. et al., Neurology 75 (2010) 1766-1772).

In the case of antibody array, antibodies are spotted onto glass or nitrocellulose chips. The slides are blocked and incubated with Tau(pS422) containing solution, washed to remove unbound antibodies and bound antibodies are detected with a fluorescently labeled corresponding secondary antibody. The fluorescence signal is measured by a fluorescence slide scanner. Similarly for a reverse phase array, recombinant Tau(pS422), cell supernatant, cell or tissue lysates, body fluids, etc. are spotted onto glass or nitrocellulose chips. The slides are blocked and individual arrays are incubated with an antibody against a specific epitope on Tau(pS422). Unbound antibodies are washed off and bound antibodies are detected with a fluorescently labeled corresponding secondary antibody. The fluorescence signal is measured by a fluorescence slide scanner (Dernick, G., et al., J. Lipid Res. 52 (2011) 2323-2331).

In the example of Western blot, aggregated recombinant Tau(pS422) or Tau(pS422) derived, e.g., from cell supernatant, cell or tissue lysates, body fluids, etc. is separated by molecular weight in SDS PAGE or native gel conditions and blotted onto a nitrocellulose or PVDF membrane. After blocking the membrane is incubated with antibodies specific to amino acid sequence or conformations of Tau(pS422). Thereafter the membrane is washed to remove unbound antibody. Bound antibodies are detected by corresponding secondary antibodies coupled to detection entities for chemiluminescence or fluorescence or other means of detection. Antibodies specific to amino acid sequences of Tau(pS422) will bind to Tau(pS422) in various aggregated forms and hence molecular weights as long as the epitope is not masked by the aggregation. On the other hand, conformation specific antibodies will detect only certain aggregated forms of Tau(pS422) revealing only bands at specific molecular weights (see, e.g., Towbin, H., et al., Proc. Natl. Acad. Sci. USA 76 (1979) 4350-4353; Burnette, W. N., Anal. Biochem. 112 (1981) 195-203).

In another aspect, competition assays may be used to identify an antibody that competes with the (humanized) antibody as reported herein for binding to human Tau (pS422). In certain embodiments, such a competing antibody binds to the same epitope (e.g., a linear or a conformational epitope) that is bound by the (humanized) antibody as reported herein. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996).

In an exemplary competition assay, immobilized human Tau(pS422) is incubated in a solution comprising a first labeled antibody that binds to human Tau(pS422) and a second unlabeled antibody that is being tested for its ability to compete with the first antibody for binding to human Tau(pS422). As a control, immobilized human Tau(pS422) is incubated in a solution comprising the first labeled antibody but not the second unlabeled antibody. After incubation under conditions permissive for binding of the first antibody to human Tau(pS422), excess unbound antibody is removed, and the amount of label associated with immobilized human Tau(pS422) is measured. If the amount of label associated with immobilized human Tau(pS422) is substantially reduced in the test sample relative to the control sample, then that indicates that the second antibody is competing with the first antibody for binding to human Tau(pS422) (see, e.g., Harlow, E. and Lane, D., Antibodies: A Laboratory Manual, Chapter 14, Cold Spring Harbor Laboratory, Cold Spring Harbor, N.Y. (1988)).

2. Activity Assays

In one aspect, assays are provided for identifying anti-human Tau(pS422) antibodies thereof having biological activity. Biological activity may include, e.g., protection from/reduction of/inhibition of Tau(pS422)-induced cytotoxicity, and/or protection from/reduction of/inhibition of cell-to-cell transmission of oligomeric human Tau(pS422), and/or reduction of Tau(pS422)-induced caspase activity in LUHMES cells. Antibodies having such biological activity in vivo and/or in vitro are also provided.

In certain embodiments, an antibody of the invention is tested for such biological activity. The protective biological activity can be assessed by adding conditioned medium containing secreted Tau(pS422), which causes cell death on recipient neuronal cells. This toxicity can be reversed by adding protective antibodies as described herein. The toxic nature of secreted Tau(pS422) has been established previously (Emmanouilidou, E., et al., J. Neurosci., 30 (2010) 6838-6851).

D. Methods and Compositions for Diagnostics and Detection

In certain embodiments, any of the anti-human Tau (pS422) antibodies provided herein are useful for detecting the presence of human Tau(pS422) in a biological sample. The term "detecting" as used herein encompasses quantitative or qualitative detection. In certain embodiments, a biological sample comprises a cell or tissue, such as brain tissue.

In one embodiment, an anti-human Tau(pS422) antibody for use in a method of diagnosis or detection is provided. In a further aspect, a method of detecting the presence of human Tau(pS422) in a biological sample is provided. In certain embodiments, the method comprises contacting the biological sample with an anti-human Tau(pS422) antibody as described herein under conditions permissive for binding of the anti-human Tau(pS422) antibody to human Tau(pS422), and detecting whether a complex is formed between the anti-human Tau(pS422) antibody and human Tau(pS422). Such method may be an in vitro or in vivo method. In one embodiment, an anti-human Tau(pS422) antibody is used to select subjects eligible for therapy with an anti-human Tau(pS422) antibody, e.g., where human Tau(pS422) is a biomarker for selection of patients.

Exemplary disorders that may be diagnosed using an antibody of the invention include neurodegeneration with brain iron accumulation type 1 (NBIA1), pure autonomic failure, Down's syndrome, complex of Guam, and several Lewy body disorders, such as diffuse Lewy body disease (DLBD), the Lewy body variant of Alzheimer's disease (LBVAD), certain forms of Gaucher's disease, and Parkinson's disease dementia (PDD).

In certain embodiments, labeled anti-human Tau(pS422) antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-human Tau (pS422) antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO 2006/044908, the latter formulations including a histidine-acetate buffer.

The formulation herein may also contain more than one active ingredients as necessary for the particular indication being treated, preferably those with complementary activities that do not adversely affect each other. For example, where the indication being treated is Alzheimer's disease or prodromal Alzheimer's disease, the pharmaceutical formulation may also contain one or more additional active ingredients such as donepezil, memantine, rivastigmine, galantamine, rivastigmine, ergoloid mesylates, an anti-Abeta antibody and an anti-alpha-synuclein antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, e.g., by filtration through sterile filtration membranes.

F. Therapeutic Methods and Compositions

Any of the anti-human Tau(pS422) antibodies provided herein may be used in therapeutic methods.

In one aspect, an anti-human Tau(pS422) antibody for use as a medicament is provided. In further aspects, an anti-human Tau(pS422) antibody for use in treating Alzheimer's disease is provided. In certain embodiments, an anti-human Tau(pS422) antibody for use in a method of treatment is provided. In certain embodiments, the invention provides an anti-human Tau(pS422) antibody for use in a method of treating an individual having Alzheimer's disease comprising administering to the individual an effective amount of the anti-human Tau(pS422) antibody. In one such embodiment, the method further comprises administering to the individual an effective amount of at least one additional therapeutic agent, e.g., as described above. In further embodiments, the invention provides an anti-human Tau (pS422) antibody for use in inhibiting Tau(pS422)-induced cytotoxicity in human neurons and glia cells, or inhibiting cell-to-cell transmission of oligomeric human Tau(pS422) between neurons and glia cells, or reducing Tau(pS422)-induced caspase activity. In certain embodiments, the invention provides an anti-human Tau(pS422) antibody for use in a method of inhibiting Tau(pS422)-induced cytotoxicity in human neurons and glia cells, or inhibiting cell-to-cell transmission of oligomeric human Tau(pS422) between neurons and glia cells, or reducing Tau(pS422)-induced caspase activity in an individual comprising administering to the individual an effective of the anti-human Tau(pS422) antibody to inhibit Tau(pS422)-induced cytotoxicity in human neurons and glia cells, or inhibit cell-to-cell transmission of oligomeric human Tau(pS422) between neurons and glia cells, or reduce Tau(pS422)-induced caspase activity. An "individual" according to any of the above embodiments is preferably a human.

In a further aspect, the invention provides for the use of an anti-human Tau(pS422) antibody in the manufacture or preparation of a medicament. In one embodiment, the medicament is for treatment of Alzheimer's disease. In a further embodiment, the medicament is for use in a method of treating Alzheimer's disease comprising administering to an individual having Alzheimer's disease an effective amount of the medicament. In one such embodiment, the method further comprises administering to the individual an effective amount of at least one additional therapeutic agent. In a further embodiment, the medicament is for inhibiting Tau(pS422)-induced cytotoxicity in human neurons and glia cells, or for inhibiting cell-to-cell transmission of oligomeric human Tau(pS422) between neurons and glia cells, or for reducing Tau(pS422)-induced caspase activity. In a further embodiment, the medicament is for use in a method of inhibiting Tau(pS422)-induced cytotoxicity in human neurons and glia cells, or inhibiting cell-to-cell transmission of oligomeric human Tau(pS422) between neurons and glia cells, or reducing Tau(pS422)-induced caspase activity in an individual comprising administering to the individual an amount effective of the medicament to inhibit Tau(pS422)-induced cytotoxicity in human neurons and glia cells, or to inhibit cell-to-cell transmission of oligomeric human Tau (pS422) between neurons and glia cells, or to reduce Tau (pS422)-induced caspase activity. An "individual" according to any of the above embodiments may be a human.

In a further aspect, the invention provides a method for treating Alzheimer's disease. In one embodiment, the method comprises administering to an individual having such Alzheimer's disease an effective amount of an anti-human Tau(pS422) antibody. In one such embodiment, the method further comprises administering to the individual an effective amount of at least one additional therapeutic agent. An "individual" according to any of the above embodiments may be a human.

In a further aspect, the invention provides a method for inhibiting Tau(pS422)-induced cytotoxicity in human neurons and glia cells, or inhibiting cell-to-cell transmission of oligomeric human Tau(pS422) between neurons and glia cells, or reducing Tau(pS422)-induced caspase in an individual. In one embodiment, the method comprises administering to the individual an effective amount of an anti-human Tau(pS422) antibody to inhibit Tau(pS422)-induced cytotoxicity in human neurons and glia cells, or to inhibit cell-to-cell transmission of oligomeric human Tau(pS422) between neurons and glia cells, or to reduce Tau(pS422)-induced caspase activity. In one embodiment, an "individual" is a human.

In a further aspect, the invention provides pharmaceutical formulations comprising any of the anti-human Tau(pS422) antibodies provided herein, e.g., for use in any of the above therapeutic methods. In one embodiment, a pharmaceutical formulation comprises any of the anti-human Tau(pS422) antibodies provided herein and a pharmaceutically acceptable carrier. In another embodiment, a pharmaceutical formulation comprises any of the anti-human Tau(pS422) antibodies provided herein and at least one additional therapeutic agent.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-human Tau(pS422) antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-human Tau(pS422) antibody.

III. ARTICLES OF MANUFACTURE

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-human Tau(pS422) antibody.

IV. SPECIFIC EMBODIMENTS

1. A humanized antibody that specifically binds to human Tau(pS422), wherein the antibody comprises
   a) in the heavy chain variable domain the HVRs of SEQ ID NO: 08, 09 and 10, or
   b) in the heavy chain variable domain the HVRs of SEQ ID NO: 08, 77 and 10.
2. The humanized antibody according to item 1, further comprising
   a) in the light chain variable domain the HVRs of SEQ ID NO: 71, 73 and 15, or
   b) in the light chain variable domain the HVRs of SEQ ID NO: 70, 72 and 15, or
   c) in the light chain variable domain the HVRs of SEQ ID NO: 12, 14 and 79, or
   d) in the light chain variable domain the HVRs of SEQ ID NO: 71, 81 and 15, or
   e) in the light chain variable domain the HVRs of SEQ ID NO: 12, 14 and 74, or
   f) in the light chain variable domain the HVRs of SEQ ID NO: 12, 14 and 75.
3. The humanized antibody according to any one of items 1 to 2, comprising
   a) in the heavy chain variable domain the HVRs of SEQ ID NO: 08, 09 and 10, and in the light chain variable domain the HVRs of SEQ ID NO: 71, 73 and 15, or
   b) in the heavy chain variable domain the HVRs of SEQ ID NO: 08, 09 and 10, and in the light chain variable domain the HVRs of SEQ ID NO: 70, 72 and 15, or
   c) in the heavy chain variable domain the HVRs of SEQ ID NO: 08, 77 and 10, and in the light chain variable domain the HVRs of SEQ ID NO: 12, 14 and 79, or
   d) in the heavy chain variable domain the HVRs of SEQ ID NO: 08, 09 and 10, and in the light chain variable domain the HVRs of SEQ ID NO: 12, 14 and 79, or
   e) in the heavy chain variable domain the HVRs of SEQ ID NO: 08, 77 and 10, and in the light chain variable domain the HVRs of SEQ ID NO: 71, 81 and 15, or f) in the heavy chain variable domain the HVRs of SEQ ID NO: 08, 09 and 10, and in the light chain variable domain the HVRs of SEQ ID NO: 12, 14 and 74, or
g) in the heavy chain variable domain the HVRs of SEQ ID NO: 08, 77 and 10, and in the light chain variable domain the HVRs of SEQ ID NO: 12, 14 and 75.

4. The humanized antibody according to any one of items 1 to 3, comprising
  a) a heavy chain variable domain of SEQ ID NO: 19 and a light chain variable domain of SEQ ID NO: 67, or
  b) a heavy chain variable domain of SEQ ID NO: 65 and a light chain variable domain of SEQ ID NO: 66, or
  c) a heavy chain variable domain of SEQ ID NO: 76 and a light chain variable domain of SEQ ID NO: 78, or
  d) a heavy chain variable domain of SEQ ID NO: 19 and a light chain variable domain of SEQ ID NO: 78, or
  e) a heavy chain variable domain of SEQ ID NO: 76 and a light chain variable domain of SEQ ID NO: 80, or
  f) a heavy chain variable domain of SEQ ID NO: 65 and a light chain variable domain of SEQ ID NO: 67, or
  g) a heavy chain variable domain of SEQ ID NO: 65 and a light chain variable domain of SEQ ID NO: 68, or
  h) a heavy chain variable domain of SEQ ID NO: 76 and a light chain variable domain of SEQ ID NO: 69.

5. A humanized bispecific antibody comprising
  i) a first binding site selected from
    a) a heavy chain variable domain of SEQ ID NO: 20 and a light chain variable domain of SEQ ID NO: 17, or
    b) a heavy chain variable domain of SEQ ID NO: 19 and a light chain variable domain of SEQ ID NO: 16, or
    c) a heavy chain variable domain of SEQ ID NO: 19 and a light chain variable domain of SEQ ID NO: 17, or
    d) a heavy chain variable domain of SEQ ID NO: 21 and a light chain variable domain of SEQ ID NO: 17, or
    e) a heavy chain variable domain of SEQ ID NO: 65 and a light chain variable domain of SEQ ID NO: 67, or
    f) a heavy chain variable domain of SEQ ID NO: 19 and a light chain variable domain of SEQ ID NO: 66, or
    g) a heavy chain variable domain of SEQ ID NO: 76 and a light chain variable domain of SEQ ID NO: 78, or
    h) a heavy chain variable domain of SEQ ID NO: 65 and a light chain variable domain of SEQ ID NO: 78, or
    i) a heavy chain variable domain of SEQ ID NO: 65 and a light chain variable domain of SEQ ID NO: 66, or
    j) a heavy chain variable domain of SEQ ID NO: 65 and a light chain variable domain of SEQ ID NO: 68, or
    k) a heavy chain variable domain of SEQ ID NO: 76 and a light chain variable domain of SEQ ID NO: 69, or
    l) a heavy chain variable domain of SEQ ID NO: 76 and a light chain variable domain of SEQ ID NO: 80,
  and
  ii) a second binding site selected from
    a) a heavy chain variable domain of SEQ ID NO: 82 and a light chain variable domain of SEQ ID NO: 85, or
    b) a heavy chain variable domain of SEQ ID NO: 83 and a light chain variable domain of SEQ ID NO: 85, or
    c) a heavy chain variable domain of SEQ ID NO: 84 and a light chain variable domain of SEQ ID NO: 85.

6. The humanized antibody according to any one of items 1 to 5, wherein the antibody is for use in the treatment of Alzheimer's disease.

7. The humanized antibody according to any one of items 1 to 6, wherein the antibody is effector function silent.

8. The humanized antibody according to any one of items 1 to 7, wherein the antibody has no effector function.

9. The humanized antibody according to any one of items 1 to 8, wherein the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02).

10. The humanized antibody according to any one of items 2 to 9, wherein the antibody has an $EC_{50}$ value for
  a) the human Tau(pS422) fragment that has the amino acid sequence of SEQ ID NO: 03 of 6 ng/mL or less, and/or
  b) the full length human Tau(pS422) that has the amino acid sequence of SEQ ID NO: 02 of 4.5 ng/mL or less, and/or
  c) aggregates of human Tau(pS422) that has the amino acid sequence of SEQ ID NO: 02 of 30 ng/mL or less, and/or
  d) the human tau that has the amino acid sequence of SEQ ID NO: 01 and that has the amino acid mutation S422A of 125 ng/mL or less.

11. The humanized antibody according to any one of items 1 to 10, wherein the antibody specifically binds to human Tau(pS422) (SEQ ID NO: 02) and does not bind to human tau (SEQ ID NO: 01).

12. The humanized antibody according to any one of items 1 to 11, wherein the antibody has in the heavy chain variable domain at positions 4, 24 and 78, a valine residue.

13. The humanized antibody according to any one of items 1 to 12, wherein the antibody has in the heavy chain variable domain at position 71, an arginine residue.

14. The humanized antibody according to any one of items 1 to 13, wherein the antibody is a monoclonal antibody.

15. The humanized antibody according to any one of items 1 to 14, wherein the antibody is an antibody fragment that binds to human Tau(pS422) and
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau (pS422) that has the amino acid sequence of SEQ ID NO: 02 of 4.5 ng/mL or less, and/or
  viii) has an $EC_{50}$ value for aggregates of human Tau (pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

16. The humanized antibody according to any one of items 1 to 14, wherein the antibody is a) a full length antibody of the human subclass IgG1, or
b) a full length antibody of the human subclass IgG4, or
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
f) a full length antibody of the human subclass IgG4 with the mutations S228P and P329G in both heavy chains and the mutations T366W and S354C in one heavy chain and the mutations T366S, L368A, Y407V and Y349C in the respective other heavy chain.

17. A humanized anti-human Tau(pS422) antibody, wherein
a) the antibody comprises two antibody heavy chains each comprising a heavy chain variable domain and a heavy chain constant region, wherein
  i) the variable domain comprises the HVRs of SEQ ID NO: 08, SEQ ID NO: 09 and SEQ ID NO: 10,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain comprises the HVRs of SEQ ID NO: 71, SEQ ID NO: 73 and SEQ ID NO: 15,
  ii) the constant region is a human kappa light chain constant region or a human lambda light chain constant region,
and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau(pS422) that has the amino acid sequence of SEQ ID NO: 02 of 4.5 ng/mL or less, and/or
  viii) has an $EC_{50}$ value for aggregates of human Tau(pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

18. A humanized anti-human Tau(pS422) antibody, wherein
a) the antibody comprises two antibody heavy chains each comprising a heavy chain variable domain and a heavy chain constant region, wherein
  i) the variable domain comprises the HVRs of SEQ ID NO: 08, SEQ ID NO: 09 and SEQ ID NO: 10,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain comprises the HVRs of SEQ ID NO: 70, SEQ ID NO: 72 and SEQ ID NO: 15,
  ii) the constant region is a human kappa light chain constant region or a human lambda light chain constant region, and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human Tau(pS422) fragment that has the amino acid sequence of SEQ ID NO: 03 of 6 ng/mL or less, and/or
  vii) has an $EC_{50}$ value for the full length human Tau(pS422) that has the amino acid sequence of SEQ ID NO: 02 of 4.5 ng/mL or less, and/or
  viii) has an $EC_{50}$ value for aggregates of human Tau(pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

19. A humanized anti-human Tau(pS422) antibody, wherein
a) the antibody comprises two antibody heavy chains each comprising a heavy chain variable domain and a heavy chain constant region, wherein
  i) the variable domain comprises the HVRs of SEQ ID NO: 08, SEQ ID NO: 09 and SEQ ID NO: 10,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain comprises the HVRs of SEQ ID NO: 12, SEQ ID NO: 14 and SEQ ID NO: 74,
  ii) the constant region is a human kappa light chain constant region or a human lambda light chain constant region,
and
c) the antibody
  i) specifically binds to a polypeptide that has the amino acid sequence of SEQ ID NO: 03, and/or
  ii) does not bind to full length human tau (SEQ ID NO: 01) at 1 µg/mL, and/or iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

20. A humanized anti-human Tau(pS422) antibody, wherein
a) the antibody comprises two antibody heavy chains each comprising a heavy chain variable domain and a heavy chain constant region, wherein
   i) the variable domain comprises the HVRs of SEQ ID NO: 08, SEQ ID NO: 77 and SEQ ID NO: 10,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain comprises the HVRs of SEQ ID NO: 12, SEQ ID NO: 14 and SEQ ID NO: 75,
   ii) the constant region is a human kappa light chain constant region or a human lambda light chain constant region,
and
c) the antibody
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human Tau(pS422) fragment that has the amino acid sequence of SEQ ID NO: 03 of 6 ng/mL or less, and/or
   vii) has an $EC_{50}$ value for the full length human Tau(pS422) that has the amino acid sequence of SEQ ID NO: 02 of 4.5 ng/mL or less, and/or
   viii) has an $EC_{50}$ value for aggregates of human Tau(pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

21. A humanized anti-human Tau(pS422) antibody, wherein
a) the antibody comprises two antibody heavy chains each comprising a heavy chain variable domain and a heavy chain constant region, wherein
   i) the variable domain has the amino acid sequence of SEQ ID NO: 65,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain has the amino acid sequence of SEQ ID NO: 67,
   ii) the constant region is a human kappa light chain constant region or a human lambda light chain constant region,
and
c) the antibody
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human Tau(pS422) fragment that has the amino acid sequence of SEQ ID NO: 03 of 6 ng/mL or less, and/or
   vii) has an $EC_{50}$ value for the full length human Tau(pS422) that has the amino acid sequence of SEQ ID NO: 02 of 4.5 ng/mL or less, and/or
   viii) has an $EC_{50}$ value for aggregates of human Tau(pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

22. A humanized anti-human Tau(pS422) antibody, wherein
a) the antibody comprises two antibody heavy chains each comprising a heavy chain variable domain and a heavy chain constant region, wherein
   i) the variable domain has the amino acid sequence of SEQ ID NO: 65,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein i) the variable domain has the amino acid sequence of SEQ ID NO: 66,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 μg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

23. A humanized anti-human Tau(pS422) antibody, wherein
a) the antibody comprises two antibody heavy chains each comprising a heavy chain variable domain and a heavy chain constant region, wherein
i) the variable domain has the amino acid sequence of SEQ ID NO: 65,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain has the amino acid sequence of SEQ ID NO: 68,
ii) the constant region is a human kappa light chain constant region or a human lambda light chain constant region,
and
c) the antibody
i) specifically binds to a polypeptide that has the amino acid sequence of SEQ ID NO: 03, and/or
ii) does not bind to full length human tau (SEQ ID NO: 01) at 1 μg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

24. A humanized anti-human Tau(pS422) antibody, wherein
a) the antibody comprises two antibody heavy chains each comprising a heavy chain variable domain and a heavy chain constant region, wherein
i) the variable domain has the amino acid sequence of SEQ ID NO: 76,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain has the amino acid sequence of SEQ ID NO: 69,
ii) the constant region is a human kappa light chain constant region or a human lambda light chain constant region, and
c) the antibody
i) specifically binds to a polypeptide that has the amino acid sequence of SEQ ID NO: 03, and/or
ii) does not bind to full length human tau (SEQ ID NO: 01) at 1 μg/mL, and/or
iii) specifically binds to full length human tau phosphorylated at the serine at position 422 (SEQ ID NO: 02), and/or
iv) specifically binds to aggregates of human tau phosphorylated at the serine at position 422 (SEQ ID NO: 02), and/or
v) specifically binds to full length human tau that has the amino acid sequence of SEQ ID NO: 01 and that has the amino acid mutation S422A, and/or
vi) has an $EC_{50}$ value for the human Tau(pS422) fragment that has the amino acid sequence of SEQ ID NO: 03 of 6 ng/mL or less, and/or
vii) has an $EC_{50}$ value for the full length human Tau(pS422) that has the amino acid sequence of SEQ ID NO: 02 of 4.5 ng/mL or less, and/or
viii) has an $EC_{50}$ value for aggregates of human Tau(pS422) that has the amino acid sequence of SEQ ID NO: 02 of 30 ng/mL or less, and/or
ix) has an $EC_{50}$ value for the human tau that has the amino acid sequence of SEQ ID NO: 01 and that has the amino acid mutation S422A of 125 ng/mL or less.

25. The humanized antibody according to any one of items 1 to 24, wherein the antibody has in the light chain variable domain at position 32, a lysine (K) amino acid residue (numbering according to Kabat).

26. An isolated nucleic acid encoding a humanized antibody according to any one of items 1 to 25.

27. A host cell comprising the nucleic acid according to item 26.

28. A method of producing a humanized antibody according to any one of items 1 to 25 comprising the steps of culturing the host cell as reported herein so that the humanized antibody is produced.
29. The method according to item 28, further comprising the step of recovering the humanized antibody from the cell or the cultivation medium.
30. A pharmaceutical formulation comprising the humanized antibody according to any one of items 1 to 25 and a pharmaceutically acceptable carrier.
31. The pharmaceutical formulation according to item 30, further comprising an additional therapeutic agent.
32. The pharmaceutical formulation according to item 31, wherein the additional therapeutic agent is an anti-amyloid therapeutic agent.
33. The pharmaceutical formulation according to item 32, wherein the anti-amyloid therapeutic agent is an anti-human alpha-synuclein antibody or an anti-Abeta antibody.
34. The humanized antibody according to any one of items 1 to 25 for use as a medicament.
35. The humanized antibody according to any one of items 1 to 25 for use in treating Alzheimer's disease.
36. The humanized antibody according to any one of items 1 to 25 for use in treating prodromal Alzheimer's disease.
37. The humanized antibody according to any one of items 1 to 25 for use in treating mild Alzheimer's disease.
38. The humanized antibody according to any one of items 1 to 25 for use in reducing Tau(pS422)-induced neurodegeneration.
39. The humanized antibody according to any one of items 1 to 25 for use in maintaining cognition and function.
40. The humanized antibody according to any one of items 1 to 25 for use in slowing the rate of cognitive and functional decline.
41. Use of the humanized antibody according to any one of items 1 to 25 in the manufacture of a medicament.
42. Use according to any one of items 34 and 41, wherein the medicament is for treatment of Alzheimer's disease.
43. Use according to any one of items 34 and 41 to 42, wherein the medicament is for treatment of prodromal Alzheimer's disease.
44. Use according to any one of items 34 and 41 to 43, wherein the medicament is for treatment of mild Alzheimer's disease.
45. Use according to any one of items 34 and 41 to 44, wherein the medicament is for reducing Tau(pS422)-induced neurodegeneration.
46. Use according to any one of items 34 and 41 to 45, wherein the medicament is for maintaining cognition and function.
47. Use according to any one of items 34 and 41 to 46, wherein the medicament is for slowing the rate of cognitive and functional decline.
48. A method of treating an individual having Alzheimer's disease comprising administering to the individual an effective amount of the humanized anti-human Tau (pS422) antibody according to any one of items 1 to 25.
49. A method of reducing Tau(pS422)-induced neurodegeneration in an individual comprising administering to the individual an effective amount of the humanized anti-human Tau(pS422) antibody according to any one of items 1 to 25 to reduce Tau(pS422)-induced neurodegeneration.
50. A method of maintaining cognition and function in an individual comprising administering to the individual an effective amount of the humanized anti-human Tau (pS422) antibody according to any one of items 1 to 25 to maintain cognition and function.
51. A method of slowing the rate of cognitive and functional decline in an individual comprising administering to the individual an effective amount of the humanized anti-human Tau(pS422) antibody according to any one of items 1 to 25 to slow the rate of cognitive and functional decline.
52. Use of the humanized anti-human Tau(pS422) antibody according to any one of items 1 to 25 in the reduction of Tau(pS422)-induced neurodegeneration.
53. Use of the humanized anti-human Tau(pS422) antibody according to any one of items 1 to 25 in maintaining cognition and function.
54. Use of the humanized anti-human Tau(pS422) antibody according to any one of items 1 to 25 in slowing the rate of cognitive and functional decline.
55. The humanized antibody according to any one of items 1 to 25, wherein the antibody i) binds to Tau(pS422) on brain sections of Tau(pS422) transgenic mice and Alzheimer's disease patients; and/or labels Tau(pS422) in Tau(pS422) transgenic cells.
56. The humanized antibody according to any one of items 1 to 25, wherein the antibody specifically binds to/recognizes early and late stage disease-relevant forms of human Tau(pS422).
57. The use of the humanized antibody according to any one of items 1 to 25 for the prevention of human Tau (pS422)-related Alzheimer's disease spread.
58. The use of the humanized antibody according to any one of items 1 to 25 for the reduction of lysosomal membrane disintegration.
59. The use of the humanized antibody according to any one of items 1 to 25 for the stabilization of lysosome membrane against human Tau(pS422)-induced destabilization and/or disintegration.
60. The use of the humanized antibody according to any one of items 1 to 25 for the prevention of Alzheimer's disease progression.

V. EXAMPLES

The following are examples of methods and compositions of the invention. It is understood that various other embodiments may be practiced, given the general description provided above.

Materials and Methods

Recombinant DNA techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Example 1

Preparation and Purification of Rabbit Antibodies
Immunization

New Zealand White (NZW) rabbits from Charles River Laboratories International, Inc. were used for immunization. Phosphopeptide tau (416-430)[pS422] coupled on keyhole limpet hemocyanin (KLH) was solved in $K_3PO_4$ puffer, pH 7.0 at a concentration of 1 mg/ml and mixed (1:1) with complete Freund's adjuvant (CFA) till generation of stabile emulsion. Three rabbits received an intra-dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval. 10 ml peripheral whole blood samples of each animal was collected 4-6 days after third, fourth, fifth and sixth injection and used for single cell sorting in FACS. An additional 0.5 ml serum of each animal was collected at the same time and used for the determination of tau (416-463)[pS422] specific antibody response.

Antibody Response

The antibody response to the immunization was determined by serial dilution of sera using an ELISA, in which 30 ng per well of biotinylated tau (416-430)[pS422] was incubated in 1×PBS at 4° C. overnight on streptavidin pre-coated 96-well microtiter plates (MC1347, Micro Coat Biotechnologie GmbH, Bernried, Germany). For detection, goat anti-rabbit IgG linked to a horseradish peroxidase (The Jackson laboratory) was used at 1:16000 dilution. BM Blue POD Substrate, precipitating tetramethyl benzidine (TMB), ready-to-use solution from Roche Diagnostics GmbH was used for visualization. Reaction was stopped via 1 N HCl and measured in Tecan Infinite by 450/690 nm.

B-Cell Cloning
Coating of Plates

Sterile streptavidin-coated 6-well plates (cell culture grade) were incubated with either a mixture of 3 biotinylated control peptides (non-phosphorylated tau (416-430), MCAK Human (88-102)[95-pSer] and MAP2_Human (1802-1816) [pSer-1802]) or with the biotinylated phospho-peptide tau (416-430)[pS422] each in a concentration at 0.5-1 μg/ml in PBS at room temperature for 1 hour. Plates were washed in sterile PBS three times before use. Cell culture 6-well plates were coated with 2 μg/ml KLH (keyhole limpet hemocyanin) in carbonate buffer (0.1 M sodium bicarbonate, 34 mM Disodiumhydrogencarbonate, pH 9.55) overnight at 4° C. Plates were washed in sterile PBS three times before use.

Isolation of Rabbit Peripheral Blood Mononuclear Cells (PBMC)

EDTA containing whole blood was diluted twofold with 1×PBS before density centrifugation on lympholyte mammal (Cedarlane Laboratories) which was performed to isolate rabbit PBMC. PBMCs were washed twice before staining with antibodies.

EL-4 B5 Medium

RPMI 1640 (Pan Biotech, Aidenbach, Germany) supplemented with 10% FCS (Hyclone, Logan, Utah, USA), 2 mM glutamine, 1% penicillin/streptomycin solution (PAA, Pasching, Austria), 2 mM sodium pyruvate, 10 mM HEPES (PAN Biotech, Aidenbach, Germany) and 0.05 mM beta-mercaptoethanol (Gibco, Paisley, Scotland).

Depletion of Macrophages/Monocytes

Sterile 6-well plates (cell culture grade) were used to deplete macrophages and monocytes through unspecific adhesion. Wells were either coated with KLH (keyhole limpet hemocyanin) or with streptavidin and the control peptides. Each well was filled with at maximum 4 ml medium and up to 6×10$^6$ peripheral blood mononuclear cells from the immunized rabbit and allowed to bind for 1 hour at 37° C. in the incubator. 50% of the cells in the supernatant were used for the panning step; the remaining 50% of cells were directly subjected to immune fluorescence staining and single cell sorting.

Panning B-Cells on Peptides 6-well tissue culture plates coated with streptavidin and the biotinylated peptide tau (416-430)[pS422] were seeded with up to 6×10$^6$ cells per 4 ml medium and allowed to bind for 1 hour at 37° C. in the incubator. Non-adherent cells were removed by carefully washing the wells 1-2 times with 1×PBS. The remaining sticky cells were detached by trypsin for 10 minutes at 37° C. in the incubator and then washed twice in media. The cells were kept on ice until the immune fluorescence staining.

Immune Fluorescent Staining and Single Cell Sorting

Anti-rabbit IgG FITC used for single cell sorting was from AbD Serotec (STAR121F, Dusseldorf, Germany). For surface staining, cells from the depletion and panning step were incubated with anti-rabbit IgG FITC antibody in PBS for 30 minutes rolling in the cold room at 4° C. in the dark. Following centrifugation, the supernatants were removed by aspiration. The PBMCs were subjected to 2 cycles of centrifugation and washing with ice cold PBS. Finally the PBMCs were resuspended in ice cold PBS and immediately subjected to the FACS analysis. Propidium iodide at a concentration of 5 μg/ml (BD Pharmingen, San Diego, Calif., USA) was added prior to the FACS analyses to discriminate between dead and live cells. FACS was performed using a Becton Dickinson FACSAria equipped the FACSDiva software (BD Biosciences, USA) and single, FITC-labeled, live cells were deposited in 96-well plates.

B-Cell Culture

B-cell cultures were prepared by a method similar to that described by Zubler, R. H. et al., J. Immunol. 134 (1985) 3662-3668. Briefly, single sorted B cells were cultured in 96-well plates with 210 μl/well EL-4 B5 medium with Pansorbin Cells (1:20000) (Calbiochem (Merck), Darmstadt, Deutschland), 5% rabbit thymocyte supernatant and gamma-irradiated EL-4-B5 murine thymoma cells (2×10$^4$/well) for 7 days at 37° C. in an atmosphere of 5% CO$_2$ in the incubator. B cell culture supernatants were removed for screening and the cells harvested immediately for variable region gene cloning or frozen at −80° C. in 100 μl RLT buffer (Qiagen, Hilden, Germany).

B-Cell Clone Screening

B-cell culture supernatants were screened for binding to biotinylated tau (416-430)[pS422] by ELISA. Non-phosphorylated tau (416-430), KLH (keyhole limpet hemocyanin) and the unrelated phospho-peptide MCAK Human (88-102)[95-pSer] were used as control antigens. For the preparation of ELISA plates, streptavidin pre-coated microtiter plates were incubated with biotinylated tau (415-430) [pS422] at 50 ng/ml for 1 hour at room temperature. Coating with KLH or control peptides was performed at 1 μg/ml. B cell supernatants were diluted 1:5 to 1:10 and were incubated in the antigen coated microtiter plates for 60 minutes. After intensive washing, the binding of the rabbit antibodies was detected using a sheep anti-rabbit IgG digoxigenin conjugated detection antibody (Chemicon AQ301D). After incubation with TMB at room temperature, absorbance at 370 nm-492 nm was measured. B-cell clones yielding signals above background with biotinylated tau (416-430) [pS422] but not with KLH and MCAK Human (88-102) [95-pSer] were further considered and subjected to variable region gene cloning.

PCR Amplification of V-Domains and Sequencing

Total RNA was prepared using the NucleoSpin® 8/96 RNA kit (Macherey&Nagel; 740709.4, 740698) according to manufacturer's protocol. All steps were done on an epMotion 5075 liquid handling system (Eppendorf). RNA was eluted with 60 µl RNAse free water. 6 µl of RNA was used to generate cDNA by reverse transcriptase reaction using the Superscript III First-Strand Synthesis SuperMix (Invitrogen 18080-400) and an oligo dT-primer according to the manufacturer's instructions. 4 µl of cDNA were used to amplify the immunoglobulin heavy and light chain variable regions (VH and VL) with the AccuPrime SuperMix (Invitrogen 12344-040) in a final volume of 50 µl using the primers rbHCfinal.up and rbHCfinal.do for the heavy chain and rbLCfinal.up and rbLCfinal.do for the light chain (see Table below). The PCR conditions were as follows: Hot start at 94° C. for 5 minutes; 35 cycles of 20 seconds at 94° C., 20 seconds at 70° C., 45 seconds at 68° C., and a final extension at 68° C. for 7 minutes.

TABLE

| | |
|---|---|
| rbHCfinal.up (SEQ ID NO: 61) | AAGCTTGCCACCATGGAGACTGGGCTGCGCTGGC TTC |
| rbHCfinal.do (SEQ ID NO: 62) | CCATTGGTGAGGGTGCCCGAG |
| rbLCfinal.up (SEQ ID NO: 63) | AAGCTTGCCACCATGGACAYGAGGGCCCCCACTC |
| rbLCfinal.do (SEQ ID NO: 64) | CAGAGTRCTGCTGAGGTTGTAGGTAC |

8 µl of the 50 µl PCR solution were loaded on a 48 E-Gel 2% (Invitrogen G8008-02). Positive PCR reactions were cleaned using the NucleoSpin® Extract II kit (Macherey&Nagel; 740609250) according to manufacturer's protocol and eluted in 50 µl elution buffer. 12 µl of purified PCR products were sequenced directly in both directions using the rbHCfinal.up and rbHCfinal.do for heavy chains and rbLCfinal.up and rbLCfinal.do for light chains (see Table above).

Recombinant Expression of Rabbit Monoclonal Antibodies and Rabbit/Mouse Chimeric Antibodies For recombinant expression of rabbit monoclonal antibodies, PCR-products coding for VH or VL were cloned as cDNA into expression vectors by the overhang cloning method (Haun, R. S. et al., BioTechniques 13 (1992) 515-518; Li, M. Z., et al., Nature Methods 4 (2007) 251-256). Linearized expression plasmids coding for the rabbit kappa or gamma constant region and VL of VH inserts were amplified by PCR using overlapping primers. Purified PCR products were incubated with T4 DNA-polymerase which generated single-strand overhangs. The reaction was stopped by dCTP addition. In the next step, plasmid and insert were combined and incubated with RecA which induced site specific recombination. The recombined plasmids were transformed into E. coli. The next day the grown colonies were picked and tested for correct recombined plasmid by plasmid preparation, restriction analysis and DNA-sequencing. For antibody expression, the isolated HC and LC plasmids were transiently co-transfected into HEK293 cells and the supernatants were harvested after 1 week. For cloning and expression of rabbit mouse chimeric antibodies, the VH and VL regions were amplified by PCR and subcloned into expression vectors containing the mouse constant kappa or mouse constant gamma 1 region. The rabbit/mouse chimeric HC and LC plasmids were isolated, tested by restriction analysis and DNA-sequencing for correct insertion and transiently co-transfected into HEK293 cells. Supernatants were harvested one week after transfection.

Antibody Purification

Recombinantly expressed rabbit antibodies were purified from cell culture supernatants on MabSelectSuRe™ columns (GE Healthcare). Prior to sample loading, the column was equilibrated with 25 mmol/L Tris-HCl, 25 mmol/L NaCl, pH 7.4. Elution of the antibody was achieved with 50 mmol/L acetate, pH 3.14. The eluted sample was immediately loaded onto a desalting column (Sephadex G25, GE Healthcare) and eluted in 20 mmol/L His-HCl, 140 mmol/L NaCl, pH 6.0. This buffer was also used for the storage of purified antibody. General storage temperature was 4° C., room temperature during the purification process and −80° C. after aliquotation. Recombinantly expressed rabbit/ mouse chimaeras antibodies from cell culture supernatants were purified on MabSelectSuRe™ columns (GE Healthcare). Prior to sample loading, the column was equilibrated with 1×PBS, pH 7.4. Elution of the antibodies was achieved with 100 mmol/L citrate, pH 3.0. The eluted sample was immediately neutralized with 2 mol/L Tris/HCl, pH 9.0. Afterwards the antibodies were loaded onto a size exclusion column (Superdex 200, GE Healthcare) and eluted in 20 mmol/L His-HCl, 140 mmol/L NaCl, pH 6.0. This buffer was also used for the storage of purified antibodies. General storage temperature was 4° C., room temperature during the purification process and −80° C. after aliquotation.

Example 2

Anti-Tau(pS422) Monoclonal Rabbit Antibodies are Highly Selective for Tau Phosphorylated at pS422 and Bind to Fibrillary Aggregates of Tau(pS422)

ELISA

Rabbit monoclonal antibodies were recombinantly expressed in HEK293 cells. Cell culture supernatants or purified rabbit antibodies were tested for binding to biotinylated tau (416-430)[pS422], non-phosphorylated tau (416-430), KLH and the unrelated phospho-peptide MCAK Human (88-102)[95-pSer] by ELISA. For preparation of ELISA plates, streptavidin pre-coated microtiter plates were incubated with biotinylated tau (415-430)[pS422] at 50 ng/ml for 1 hour at room temperature. Coating with KLH or control peptides was performed at 1 µg/ml. Rabbit anti-Tau (pS422) antibody (Abcam AB51071) or rabbit antibody containing supernatants were incubated in the antigen labeled microtiter plates for 60 minutes at various concentrations. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its $EC_{50}$ values. Antibody binding to biotinylated tau (416-430)[pS422] and non-phosphorylated tau (416-430) peptides was characterized by its $EC_{50}$ values. Cross-reactivity with KLH or MCAK phosphopeptide was estimated by single-point measurement at high concentrations, i.e., at 1:5 dilution of the cell culture supernatants. Results are shown in the Table below. $EC_{50}$ values of binding to tau phosphopeptide were found to be more than 100 times lower than $EC_{50}$ values of binding to tau peptide, indicating at least 100 fold selectivity for phosphorylated tau fragment compared to non-phosphorylated tau peptide. Binding to KLH and MCAK control phosphopeptide was at background level with all antibodies, which is about 1 to 3% of the maximal value measures with tau phosphopeptide.

TABLE

| | $EC_{50}$ phosphorylated tau peptide (µg/ml) | $EC_{50}$ non-phosphorylated tau peptide (µg/ml) | IgG titer of supernatant (µg/ml) | OD 1:5 dilution of supernatant | |
|---|---|---|---|---|---|
| | | | | KLH (mE) | MCAK (mE) |
| mAb 005 | <0.003 | 3.727 | 5.818 | 0.026 | 0.067 |
| mAb 019 | <0.003 | 1.076 | 6.958 | 0.026 | 0.023 |
| mAb 020 | 0.002 | >3.369 | 3.369 | 0.016 | 0.010 |
| mAb 085 | 0.0009 | 0.146 | 6.46 | 0.029 | 0.062 |
| mAb 086 | 0.0011 | 0.266 | 8.84 | 0.046 | 0.104 |
| mAb 097 | 0.0013 | 1.281 | 19.87 | 0.042 | 0.029 |

Specificity for soluble and aggregated full-length Tau (pS422) was also tested. Fibrillary aggregates of Tau(pS422) (300 µg/ml) were coated on a polystyrene based Maxisorb microtiter plate (Nunc) overnight at room temperature. In similar manner, soluble full-length tau and Tau(pS422) were coated on a Maxisorb microtiter plate. Rabbit anti-Tau (pS422) antibody control (Abcam AB51071), or purified rabbit antibodies were added and incubated for 60 minutes in concentrations up to 1000 ng/ml. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its $EC_{50}$ values. Results are shown in the following Table.

TABLE

| Rabbit mAb | $EC_{50}$ Tau(pS422) protein (µg/ml) | $EC_{50}$ tau protein (µg/ml) | $EC_{50}$ fibrillary Tau(pS422) (µg/ml) |
|---|---|---|---|
| mAb 005 | 0.00034 | no binding | 0.00755 |
| mAb 019 | 0.00038 | no binding | 0.00059 |
| mAb 020 | 0.00036 | no binding | 0.00042 |
| mAb 085 | 0.00025 | no binding | 0.00074 |
| mAb 086 | 0.00023 | no binding | 0.00048 |
| mAb 097 | 0.00040 | no binding | 0.01358 |

Rabbit monoclonal antibodies bound to Tau(pS422) protein with $EC_{50}$ values below 1 ng/ml. Fibrillary Tau(pS422) was detected with $EC_{50}$ values ranging from 0.4 ng/ml to 14 ng/ml. Signals for binding to non-phosphorylated full-lengths tau protein were indistinguishable from background levels. Therefore it was estimated that each of the antibodies binds to Tau(pS422) and fibrillary Tau(pS422) with a selectivity of at least 100-fold compared to tau. BIAcore™

Binding to fibrillary Tau(pS422) aggregates was further investigated and confirmed by BIAcore™ analysis. Measurements were performed using the BIAcore 3000 instrument at 37° C. The system and sample buffer was HBS-EP (10 mM HEPES, 150 mM NaCl, 3.4 mM EDTA, 0.005% Polysorbate 20 (v/v)). A BIAcore™ CM5 sensor chip was subjected to a preconditioning procedure. Sequentially 0.1% SDS, 50 mM NaOH, 10 mM HCl and 100 mM $H_3PO_4$ were injected for 30 seconds over the flow cells FC1, FC2, FC3 and FC4. The amine coupling procedure was done according to the manufacturer's instructions using the BIAcore 3000™ wizard v. 4.1. After an EDC/NHS activation of the sensor surface, a non-phosphoselective anti-tau antibody mAb <TAU>M-4/53-IgG was immobilized on sensor flow cells FC2, FC3 and FC4. As a control, an antibody against CK-MM (creatine kinase isotype), recognizing an irrelevant antigen, was captured on the FC1 flow cell. mAb <TAU>M-4/53-IgG and the antibody against CK-MM were diluted at 30 µg/ml in 10 mM NaAc, pH 5.0 and were injected at 10 µl/min for 7 minutes contact time to immobilize 10,000 RU of the antibody capturing system. The surface was deactivated by saturation with 1 M ethanolamine. The sensor was conditioned by 5 cycles with phosphorylated filamentous tau protein (stock 0.3 mg/ml diluted 1:100 in HBS-EP) as analyte in solution at 10 µl/min for 2 minutes. Regeneration was performed with 10 mM glycine, pH 2.5 at 30 µl/min for 3 minutes. It was assumed, that the analyte binding to mAb 4/53 does not dissociate the pTau filaments, because no dissociation of pTau filaments from the mAb 4/53 could be observed. For all further measurement cycles, 0.3 mg/ml pTau filaments were diluted 1:100 in HBS-EP buffer and were injected at 10 µl/min for 1 minute, in order to present pTau to the respective antibody analytes in a heterogeneous sandwich-mode. The antibody analytes were diluted in HBS-EP buffer to a concentration of 100 nM and were injected into the system at 20 µl/min for 3 minutes. After 3 minutes of dissociation, the sensor surface was regenerated by 2 injections of a 10 mM glycine, pH 2.5, for 1 minute at 100 followed by a HBS-wash for 15 seconds at 100 µl/minute The association and dissociation phase of the interactions were monitored. Since the antibody analyte in solution is bivalent, the avidity-burdened antibody-pTau kinetics were characterized by a biphasic dissociation model, consisting of a fast affinity-based early dissociation step followed by an avidity-stabilized, but rate-limiting kinetic step in the latter complex dissociation. 10 seconds (early) and 50 seconds (late) after analyte injection end, the kd and t/2(diss) were quantified, where possible. The kinetic measurements were evaluated using a double referencing procedure. First the signal from the FC1 reference was subtracted to correct the buffer bulk effect and unspecific binding. Second the 0 nM analyte injection was subtracted to correct the dissociation of the primary antibodies from the respective capturing system. The kinetic rates were evaluated using a Langmuir 1.1 dissociation fit model according to the BIAcore™ evaluation software v.4.1. The antigen/antibody complex stability halftime (min) was calculated according to the formula ln(2)/60*kd.

Results are summarized in the following Table.

TABLE

| | early (10 s) | | late (50 s) | |
|---|---|---|---|---|
| Clone | kd (1/s) | t/2diss (min) | kd (1/s) | t/2diss (min) |
| mAb 005 | 2.19E-03 | 5.3 | $3.12 \times 10^{-3}$ | 4 |
| mAb 019 | 1.43E-02 | 0.8 | $6.17 \times 10^{-4}$ | 19 |

TABLE-continued

| | early (10 s) | | late (50 s) | |
|---|---|---|---|---|
| Clone | kd (1/s) | t/2diss (min) | kd (1/s) | t/2diss (min) |
| mAb 020 | 3.28E−03 | 3.5 | 4.08 × 10⁻⁴ | 28 |
| mAb 085 | n.d. | n.d. | 6.60 × 10⁻⁴ | 18 |
| mAb 086 | 1.62E−03 | 7.2 | 3.68 × 10⁻⁴ | 32 |
| mAb 097 | n.d. | n.d. | n.d. | n.d. |

Example 3

Binding of Anti-Tau(pS422) Monoclonal Rabbit Antibodies to Intracellular pTau in Brain Sections of Alzheimer's Disease Patients The specific and sensitive immunohistochemical detection of pTau pathology in Alzheimer's disease brain tissue by monoclonal rabbit anti-Tau(pS422) antibodies was investigated by immunofluorescence staining experiments using cryosections of human brain tissue from AD patients. Rabbit IgGs were detected by goat anti-rabbit Alexa Fluor488® conjugated secondary antibodies (Invitrogen/Molecular Probes A11034). Specific and sensitive staining of pTau deposits and filaments was evident for clones mAb 005, mAb 019, mAb 020, mAb 085, mAb 086 and mAb 097. Intracellular pTau deposits, like large neurofibrillary tangles and elongated neutrophil threads, were noticeable. A minimal effective concentration ranging between 0.08 and 0.016 µg/ml was determined for all clones investigated, which indicates highly sensitive binding to genuine human pTau deposits.

Example 4

Humanization of Rabbit Anti-Human Tau(pS422) Antibodies

The "variable domain" (variable domain of a light chain (VL), variable domain of a heavy chain (VH)) as used herein denotes each of the pair of light and heavy chain domains which are involved directly in binding the antibody to the Tau(pS422) antigen. The variable light and heavy chain domains have the same general structure and each domain comprises four framework (FR) regions whose sequences are widely conserved, connected by three "hypervariable regions".

The structures of the VH and the VL domain of the rabbit antibody mAb 086 were analyzed in silico and compared to a structural database of human VH and VL domains (IMGT). A panel of structurally most similar V domains was chosen for grafting the CDRs of the rabbit antibody onto the chosen human VH and VL domains. In addition, similarities in the primary sequence were taken into account to narrow down the choice of the human V domains by aligning the primary sequence of the VH and VL domain of the rabbit antibody to the human V domain repertoire. Backmutations within the human framework regions to rabbit parent residues were introduced in some humanization variants. Similarly, mutations in the CDRs were introduced in some variants where appropriate to potentially increase the affinity to the antigen, to maintain the CDR tertiary structure, and to remove unwanted features like cysteine residues or residues that can undergo modification after antibody purification.

The heavy and light chain vectors containing each of the humanized variant were co-transfected into HEK293 suspension cells in microtiter culture plates in a matrix manner to obtain cell cultures expressing full size IgG of all possible light/heavy chain combinations. After 5 days cultivation at 37° C., the supernatants were harvested and purified by protein A affinity chromatography in the microtiter scale.

Example 5

Generation of Recombinant Expression Vectors
a) Generation of Vectors for the Expression of Immunoglobulin Heavy Chains Using the Human IgG1 Constant Region The humanized heavy chain encoding fusion gene comprising the human IgG1 constant region (CH1, hinge, CH2, CH3) and a humanized anti-human Tau(pS422) antibody VH domain derived from rabbit antibody mAb 086 was assembled by fusing a DNA fragment coding for the respective anti-human Tau(pS422)-specific antibody VH domain to a sequence element coding the human IgG1 constant region.

The human IgG1 constant region has the following amino acid sequence:

```
                                           (SEQ ID NO: 58)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK.
```

The expression vector also comprised an origin of replication from the vector pUC18, which allows replication of this plasmid in *E. coli*, and a beta-lactamase gene which confers ampicillin resistance in *E. coli*.

The transcription unit of the antibody heavy chain comprises the following functional elements in 5' to 3' direction:
the immediate early enhancer and promoter from the human cytomegalovirus (P-CMV) including intron A,
a human heavy chain immunoglobulin 5'-untranslated region (5'UTR),
a murine immunoglobulin heavy chain signal sequence,
a heavy chain variable (VH) domain encoding nucleic acid,
a human IgG1 constant region encoding nucleic acid, and
the bovine growth hormone polyadenylation sequence (BGH pA).

b) Generation of Vectors for the Expression of Immunoglobulin Light Chains Using the Human Ig-Kappa Constant Region The humanized kappa light chain encoding fusion gene comprising the human Ig-kappa constant region (CL-kappa) and an anti-human Tau(pS422) antibody VL (kappa) domain derived from rabbit antibody mAb 086 was assembled by fusing a DNA fragment coding for the respective anti-human Tau(pS422) antibody VL (kappa) domain to a sequence element coding for the human Ig-kappa constant region.

The human Ig-kappa constant region has the following amino acid sequence:

```
                                            (SEQ ID NO: 59)
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC.
```

The expression vector also comprised an origin of replication from the vector pUC18, which allows replication of this plasmid in *E. coli*, and a beta-lactamase gene which confers ampicillin resistance in *E. coli*.

The transcription unit of the antibody kappa light chain comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a light chain variable (VL) domain encoding nucleic acid,
- a human Ig-kappa constant region encoding nucleic acid, and
- the bovine growth hormone polyadenylation sequence (BGH pA).

c) Generation of Vectors for the Expression of Immunoglobulin Light Chains Using the Human Ig-Lambda Constant Region The humanized lambda light chain encoding fusion gene comprising the human Ig-lambda constant region (CL-lambda) and an anti-human Tau(pS422) antibody VL (lambda) domain derived from rabbit antibody mAb 086 was assembled by fusing a DNA fragment coding for the respective anti-human Tau(pS422) antibody VL (lambda) domain to a sequence element coding for the human Ig-lambda constant region.

The human Ig-lambda constant region has the following amino acid sequence:

```
                                            (SEQ ID NO: 60)
GQPKAAPSVT LFPPSSEELQ ANKATLVCLI SDFYPGAVTV

AWKADSSPVK AGVETTTPSK QSNNKYAASS YLSLTPEQWK

SHRSYSCQVT HEGSTVEKTV APTECS.
```

The expression vector also comprised an origin of replication from the vector pUC18, which allows replication of this plasmid in *E. coli*, and a beta-lactamase gene which confers ampicillin resistance in *E. coli*.

The transcription unit of the antibody lambda light chain comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a variable light chain (VL) domain encoding nucleic acid,
- a human Ig-lambda constant region encoding nucleic acid, and
- the bovine growth hormone polyadenylation sequence (BGH pA).

d) Generation of Vectors for the Expression of Immunoglobulin Kappa Light Chains Using the Human Ig-Kappa Constant Region The human Ig-kappa light chain encoding fusion gene comprising the human Ig-kappa constant region (CL-kappa) and an anti-human Tau(S422) antibody VL (kappa) domain derived from rabbit antibody mAb 086 was assembled by fusing a DNA fragment coding for the respective anti-human Tau(pS422)-antibody VL (kappa) domain to a sequence element coding for the human Ig-kappa constant region. The construct was in a genomic organization, i.e., introns were present in the signal peptide and between the VL (kappa) and the CL-kappa domains.

The expression vector also comprised an origin of replication from the vector pUC18, which allows replication of this plasmid in *E. coli*, and a beta-lactamase gene which confers ampicillin resistance in *E. coli*.

The transcription unit of the antibody kappa light chain comprises the following functional elements in 5' to 3' direction:
- the immediate early enhancer and promoter from the human cytomegalovirus (P-CMV),
- a human heavy chain immunoglobulin 5'-untranslated region (5'UTR),
- a murine immunoglobulin heavy chain signal sequence,
- a light chain variable (VL) domain encoding nucleic acid,
- a human IgG kappa constant region, and
- the bovine growth hormone polyadenylation sequence (BGH pA).

e) Generation of Vectors for the Expression of Immunoglobulin Lambda Light Chains Using the Human Ig-Lambda Constant Region The human Ig-lambda light chain encoding fusion gene comprising the human Ig-lambda constant region (CL-lambda) and an anti-human Tau(S422) antibody VL (lambda) domain derived from rabbit antibody mAb 086 was assembled by fusing a DNA fragment coding for the respective anti-human Tau(pS422) antibody VL (lambda) domain to a sequence element coding for the human Ig-lambda constant region. The construct was in a genomic organization, i.e., introns were present in the signal peptide and between the VL (lambda) and the CL-lambda domains.

The expression vector also comprised an origin of replication from the vector pUC18, which allows replication of this plasmid in *E. coli*, and a beta-lactamase gene which confers ampicillin resistance in *E. coli*.

The transcription unit of the antibody lambda light chain comprises the following functional elements in 5' to 3' direction:
- the immediate early enhancer and promoter from the human cytomegalovirus (P-CMV),
- a human heavy chain immunoglobulin 5'-untranslated region (5'UTR),
- a murine immunoglobulin heavy chain signal sequence,
- a light chain variable (VL) domain encoding nucleic acid,
- a human IgG lambda constant region, and
- the bovine growth hormone polyadenylation sequence (BGH pA).

Example 6

Recombinant Production of Anti-Human Tau(pS422) Antibodies

Antibodies were produced in transiently transfected HEK293 cells (human embryonic kidney cell line 293-derived), cultivated in F17 Medium (Invitrogen Corp.). For transfection of the respective vectors as described in Example 5 "293-Free" Transfection Reagent (Novagen) was used. The antibodies were expressed from individual expression plasmids. Transfections were performed as specified in the manufacturer's instructions. Recombinant antibody-containing cell culture supernatants were harvested three to seven days after transfection. Supernatants were stored at reduced temperature (e.g., −80° C.) until purification.

General information regarding the recombinant expression of human immunoglobulins in, e.g., HEK293 cells is given in: Meissner, P. et al., Biotechnol. Bioeng. 75 (2001) 197-203.

Example 7

Purification of Recombinant Anti-Human Tau(pS422) Antibodies

The antibody-containing culture supernatants were filtered and purified by two chromatographic steps.

The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.1, which was immediately after elution adjusted to pH 6.0 with 1 M Tris-base, pH 9.0.

Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass., USA) and stored at −80° C.

Example 8

Kinetic Screening

Kinetic screening was performed according to Schraeml et al. (Schraeml, M. and M. Biehl, Methods Mol. Biol. 901 (2012) 171-181) on a BIAcore 4000 instrument, mounted with a BIAcore CM5 sensor. The BIAcore 4000 instrument was under the control of the software version V1.1. A BIAcore CM5 series S chip was mounted into the instrument and was hydrodynamically addressed and preconditioned according to the manufacturer's instructions. The instrument buffer was HBS-EP buffer (10 mM HEPES (pH 7.4), 150 mM NaCl, 1 mM EDTA, 0.05% (w/v) P20). An antibody capture system was prepared on the sensor surface. A polyclonal goat anti-human antibody with human IgG-Fc specificity (Jackson Lab.) was immobilized at 30 µg/ml in 10 mM sodium acetate buffer (pH 5) to spots 1, 2, 4 and 5 in the instrument's flow cells 1, 2, 3 and 4 at 10,000 RU using NHS/EDC chemistry. In each flow cell the antibodies were captured on spot 1 and spot 5. Spot 2 and spot 4 were used as reference spots. The sensor was deactivated with a 1 M ethanolamine solution. Humanized antibody derivatives were applied at concentrations between 44 nM and 70 nM in instrument buffer supplemented with 1 mg/ml CMD (carboxymethyldextrane). The antibodies were injected at a flow rate of 30 µl/min for 2 minutes. The capture level (CL) of the surface-presented antibodies was measured in rel. response units (RU). The analytes in solution, phosphorylated human tau protein, non-phosphorylated human tau protein and the phosphorylated human tau mutant protein T422S, were injected at 300 nM for 3 minutes at a flow rate of 30 µl/minute The dissociation was monitored for 5 minutes. The capture system was regenerated by a 1 minute injection of 10 mM glycine buffer, pH 1.7 at 30 µL/min over all flow cells. Two report points, the recorded signal shortly before the end of the analyte injection, denoted as binding late (BL) and the recorded signal shortly before the end of the dissociation time, stability late (SL), were used to characterize the kinetic screening performance. Furthermore, the dissociation rate constant kd (1/s) was calculated according to a Langmuir model and the antibody/antigen complex half-life was calculated in minutes according to the formula ln(2)/(60*kd). The molar ratio (MR) was calculated according to the formula MR=(Binding Late (RU))/(Capture level (RU))*(MW(antibody)/(MW(antigen)). In case the sensor was configured with a suitable amount of antibody ligand capture level, each antibody should be able to functionally bind at least to one analyte in solution, which is represented by a molar ratio of MR=1.0. Then, the molar ratio is also an indicator for the valence mode of analyte binding. The maximum valence can be MR=2 for an antibody binding two analytes, one with each Fab valence.

In another embodiment, kinetic rates were determined at 25° C. and 37° C. using the same experimental setup, but using multiple concentration series of each analyte in solution at 0 nM (buffer), 1.2 nM, 3.7 nM, 11.1 nM, 33.3 nM, 100 nM and 300 nM. From the concentration-dependent binding behavior the kinetic data was calculated using the BIAcore evaluation software according to the manufacturer's instructions and a Langmuir 1.1 model with RMAX global.

Example 9

ELISA

Non-biotinylated peptide/protein/aggregate was added to non-coated Maxisorb plates, biotinylated peptide/protein/aggregate in PBS was added to streptavidin-coated Maxisorb plates, and plates were incubated over-night. The supernatant was discarded and the wells washed three times with 90 µl wash buffer (1×PBS/0.1% Tween 20). Remaining reactive spots were blocked with blocking buffer (1×PBS/2% BSA (Bovine Serum Albumin Fraction V, fatty acid free, Roche, Cat. No.: 10735078001)/0.05% Tween 20) by incubating for 1 hour. The supernatant was discarded and the wells washed three times with 90 µl wash buffer. Samples and control antibody were prepared in 12 dilutions (1:2) in ELISA buffer (1×PBS/0.5% BSA (Bovine Serum Albumin Fraction V, fatty acid free, Roche, Cat. No.: 10735078001)/0.05% Tween 20) with a start concentration of 500 ng/mL. The incubation time was 60 minutes at room temperature on a shaker. The supernatant was discarded and the wells washed three times with 90 µl wash buffer. Solutions of secondary antibody were prepared in ELISA buffer. A total of 25 µl antibody-mix was transferred to all wells of the assay plate and the plate was thereafter incubated on shaker for 60 minutes at room temperature. The supernatant was discarded and the wells were washed three times with 90 µl wash buffer. 25 µl of ABTS solution was added to all wells. The absorbance was read at 405 nm-492 nm.

Example 10

Kinetic Measurement of pTau Peptide Binding to Anti-pTau Antibodies (Capture Assay)

Binding of pTau fragment to anti-pTau antibodies was investigated by surface plasmon resonance using a BIACORE T200 instrument (GE Healthcare). Around 10,000 resonance units (RU) of the capturing system (10 µg/ml goat anti-human Fc antibody; Jackson Immuno Research; Order Code: JIR 109-005-098) were coupled on a CM5 chip (GE Healthcare BR-1005-30) at pH 5.0 by using an amine coupling kit supplied by the GE Healthcare. As running buffer, HBS-N pH 7.4 (10 mM HEPES, 150 mM NaCl, pH 7.4, GE Healthcare) was used. For measurement of the samples, running and dilution buffer was PBS-T (10 mM phosphate buffered saline including 0.05% Tween 20), pH 7.4. The sample block was set to 12° C. The flow cell was set to 25° C. and primed with running buffer twice.

The anti-pTau antibody was captured by injecting a 10 µg/ml solution for 300 seconds at a flow of 10 µl/minute Association was measured by injection of pTau fragment at various concentrations in solution for 180 seconds at a flow of 30 µl/min starting with 300 nM in 1:3 dilutions. The dissociation phase was monitored for up to 300 seconds and triggered by switching from the sample solution to running buffer. The surface was regenerated by 60 seconds of washing with a 0.85% phosphoric acid solution, followed by 60 seconds of washing with 5 mM sodium hydroxide solution at a flow rate of 10 µl/minute Bulk refractive index differences were corrected by subtracting the response obtained from a goat anti-human Fc antibody surface. Blank injections were also subtracted (=double referencing). For calculation of KD and other kinetic parameters the Langmuir 1:1 model was used.

Example 11

Kinetic Measurement of Anti-pTau Antibody Fab Fragments Binding to pTau Fragment (Direct Assay)

Binding of anti-pTau antibody Fab fragment samples to pTau fragment was investigated by surface plasmon resonance using a BIACORE T200 instrument (GE Healthcare). Approximately 20 resonance units (RU) of biotinylated pTau fragment (0.2 µg/ml; pTau(416-430)[Bi-XUUUU-416; pSer-422]amid) was coupled on a Series S SA chip (GE Healthcare BR-1005-31). Running and dilution buffer for immobilization was HBS-N, pH 7.4 (10 mM HEPES, 150 mM NaCl, pH 7.4, GE Healthcare). For the following kinetic characterization, running and dilution buffer was PBS-T (10 mM phosphate buffered saline including 0.05% Tween 20), pH 7.4. The sample block was set to 12° C. The flow cell was set to 25° C. and primed with running buffer twice.

Association was measured by injection of the anti-pTau antibody Fab fragment samples at various concentrations in solution for 180 seconds at a flow of 30 µl/min starting with 100 nM in 1:3 dilutions. The dissociation phase was monitored for up to 600 seconds and triggered by switching from the sample solution to running buffer. The surface was regenerated by washing with one injection of 10 mM glycine solution, pH 1.7 for 60 seconds at a flow rate of 10 µl/minute. Bulk refractive index differences were corrected by subtracting the response obtained from a blank surface. Blank injections were also subtracted (=double referencing). For calculation of KD and other kinetic parameters the Langmuir 1:1 model was used.

Example 12

Kinetic Measurement of Anti-pTau Antibody Fab Fragments Binding to Full Length pTau (Direct Assay)

Binding of anti-pTau antibody Fab fragment samples to full length pTau protein was investigated by surface plasmon resonance using a BIACORE T200 instrument (GE Healthcare). Approximately 200 resonance units (RU) of biotinylated pTau protein (2 µg/ml) was coupled on a Series S SA chip (GE Healthcare BR-1005-31). Running and dilution buffer for immobilization was HBS-N, pH 7.4 (10 mM HEPES, 150 mM NaCl, pH 7.4, GE Healthcare). For the following kinetic characterization, running and dilution buffer was PBS-T (10 mM phosphate buffered saline including 0.05% Tween 20), pH 7.4. The sample block was set to 12° C. The flow cell was set to 25° C. and primed with running buffer twice.

Association was measured by injection of the anti-pTau antibody Fab fragment samples at various concentrations in solution for 180 seconds at a flow of 30 µl/min starting with 300 nM in 1:3 dilutions. The dissociation phase was monitored for up to 600 seconds and triggered by switching from the sample solution to running buffer. The surface was regenerated by washing with one injection of 10 mM glycine solution, pH 1.7 for 60 seconds at a flow rate of 10 µl/minute. Bulk refractive index differences were corrected by subtracting the response obtained from a blank surface. Blank injections were also subtracted (=double referencing). For calculation of KD and other kinetic parameters the Langmuir 1:1 model was used.

Example 13

Effect of Anti-Tau(pS422) Antibody (VH35H5/VL31A1) and Anti-Tau(pS422) Antibody (VH35H5/VL49 G1) on Tau Pathology in Human Tau-Overexpressing Mice TauPS2APP transgenic mice overexpressing the longest human tau isoform (Grüninger et al., Neurobiol. Dis. 37 (2010) 294) were treated with either with antibody 1 (VH35H5/VL31A1), antibody 2 (VH35H5/VL49G1) or vehicle for a period of 16 weeks. Just before treatment, all mice were immunosuppressed by administration of a single dose of an anti-CD4 antibody (0.5 mg/mouse). The mice subsequently received weekly i.p. injections of the respective antibody or vehicle starting at 9 months of age. For each of the two antibodies, three separate doses were tested, namely, 1.7 mg/kg, 5 mg/kg and 15 mg/kg. Mice were sacrificed 4-6 days after the last injection, transcardially perfused and the brains were removed for analysis. An untreated group of mice (9 months old) was sacrificed at the beginning of the experiment and used as baseline comparator.

Each brain was sectioned sagittally and the individual hemispheres snap-frozen on dry ice. The left hemisphere was used for biochemical quantitation of tau, Tau(pS422) and tau aggregates by immunoassay. The right brain hemisphere was used for quantitative immunohistochemical analysis of Tau(pS422)-containing neurofibrillary tau.

Methods

Preparation of Brain Homogenates

One brain hemisphere from each mouse was weighed and added to 10 volumes of ice-cold extraction buffer (25 mM Tris-HCl, 800 mM NaCl, 10% sucrose, 1 mM EGTA, pH 7.5, supplemented with 1% Protease Inhibitor Cocktail (Calbiochem #539134) and 1% Phosphatase Inhibitor Cocktail (Sigma #P0044)). The tissue was then homogenized in a 2 ml glass Dounce homogenizer. Homogenate was centrifuged at 20.000×g for 20 minutes at 4° C. Pelleted material was discarded, homogenate was aliquoted and stored at −20° C. until further use.

AlphaLISA Quantitation of Tau and Tau(pS422) in Brain Homogenates

AlphaLISA streptavidin-coated Donor and unconjugated Acceptor beads were purchased from Perkin Elmer. Acceptor beads were coupled to either anti-tau antibody or anti-Tau(pS422) antibody.

Anti-tau antibody 5A6 (DSHB) was biotinylated on primary amine groups using biotin-N-hydroxysuccinamide (Thermo Fisher).

Tau measurement was performed in 1×HiBlock Assay Buffer (Perkin Elmer) using biotinylated-5A6 antibody, streptavidin Donor beads and anti-tau antibody Acceptor beads.

Tau(pS422) measurement was performed in Assay Buffer B (25 mM Hepes, pH 7.4, 0.5% Triton X-100, 0.1% TopBlock (LuBioscience), 1 mg/ml Dextran 500, ⅒ Blocking Reagent (Roche)) using biotinylated-5A6 antibody, streptavidin Donor beads and anti-Tau(pS422) antibody Acceptor beads.

Samples were prepared for assay in ½ AreaPlate-96 (Perkin Elmer) by mixing 5 µl of standard or sample with 10 µl of biotinylated-5A6 antibody and 10 µl of antibody-coupled Acceptor beads then incubating for 1 hour at room temperature with shaking. The mixture was then supplemented with 25 µl of streptavidin Donor beads and incubated for a further 30 minutes at room temperature in the dark with shaking. Plates were then measured in a Envision microtitre plate reader (Perkin Elmer) using laser excitation at 680 nm and a 615 nm emission filter. Standard curves were generated using recombinant human tau (longest isoform) and ERK-phosphorylated tau.

Quantitative Immunohistochemical Analysis of pTau Pathology

Sagittal cryosections (thickness 10 µm) were prepared on a cryostat and four sections per animal were immunofluorescence-stained with an antibody against Tau(S422) conjugated to goat anti-mouse/AlexaFluor555 at a concentration of 10 µg/ml.

Image acquisition of entire brain sections was done with a Metafer 4 slide scanning system (MetaSystems GmbH, Altlussheim, Germany). The Tau(pS422) immunopositive area was measured within the hippocampus and neocortical region and area of pTau-positive immunofluorescence signal determined by an unbiased morphometrical method by means of computer-assisted image analysis. Quantification of pTau positive area was done with Definiens image analysis software (Definiens A G, Munich, Germany).

Results

Figure 7A:
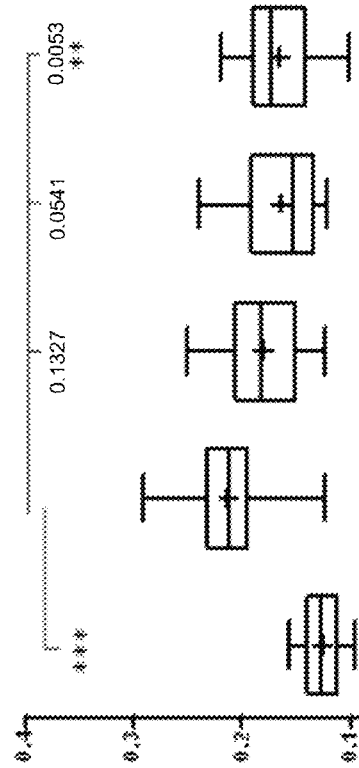
FIG. 7A-FIG. 7B show quantitation of Tau(pS442) levels in mouse brain extracts; max-min, median and mean (+); significance was calculated using Student's t-test, *p<0.05, p<0.01, *p<0.001.
Figure 7B:
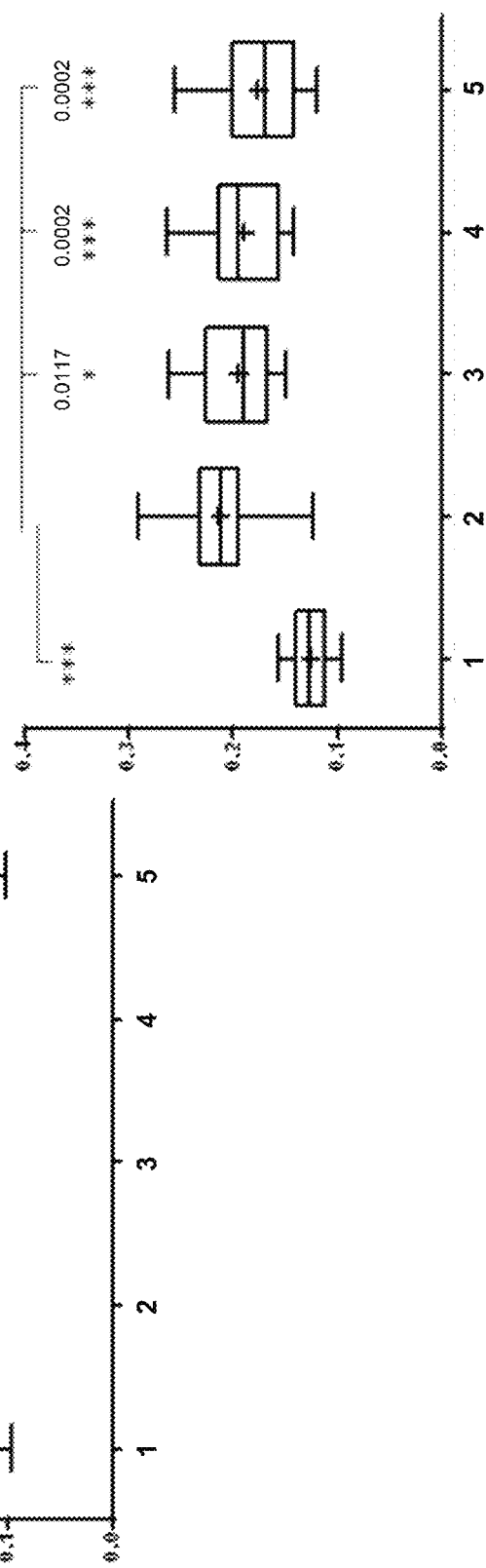
Figure 8A:
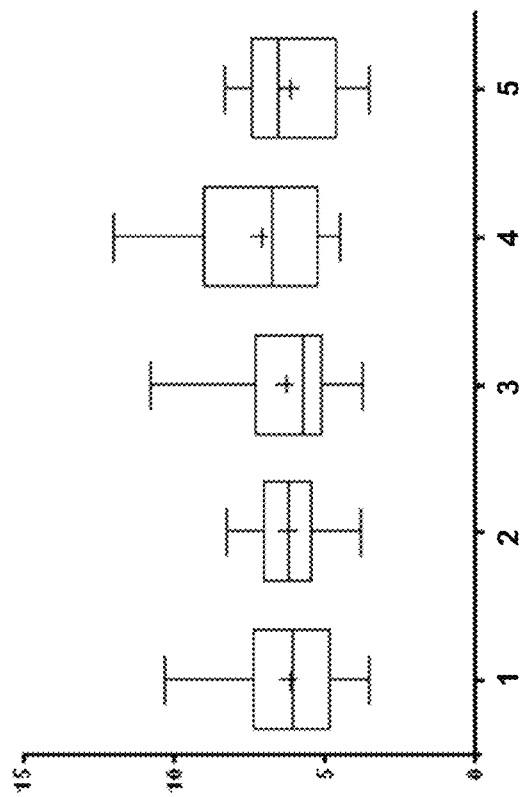
FIG. 8A-FIG. 8B show quantitation of total tau in mouse brain extracts; max-min, median and mean (+).
Figure 8B:
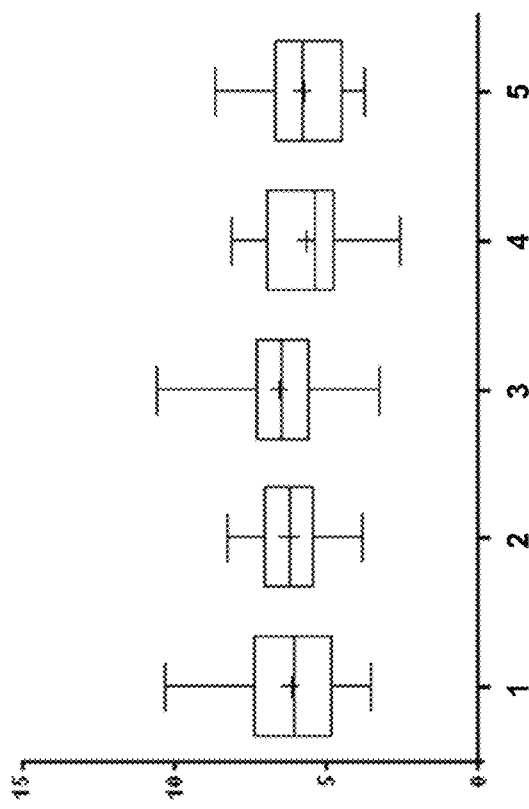
Figure 9A:
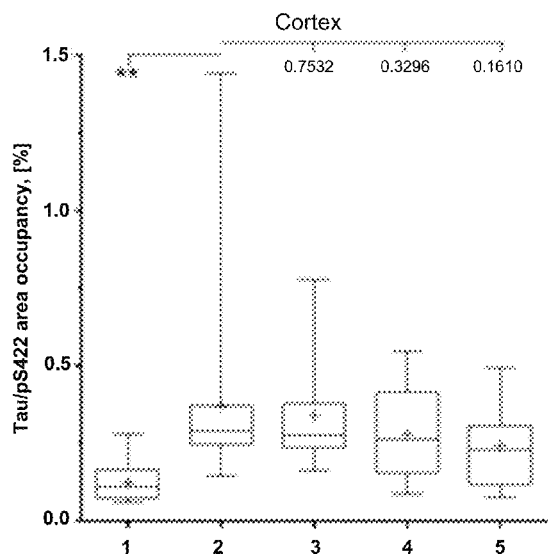
FIG. 9A-FIG. 9B show quantitative IHC analysis of Tau(pS422) pathology in anti-Tau(pS422) antibody (VH35H5/VL31A1)-treated TauPS2APP mice; max-min, median and mean (+), significance was calculated using Student's t-test, p<0.01, *p<0.001.
Figure 9B:
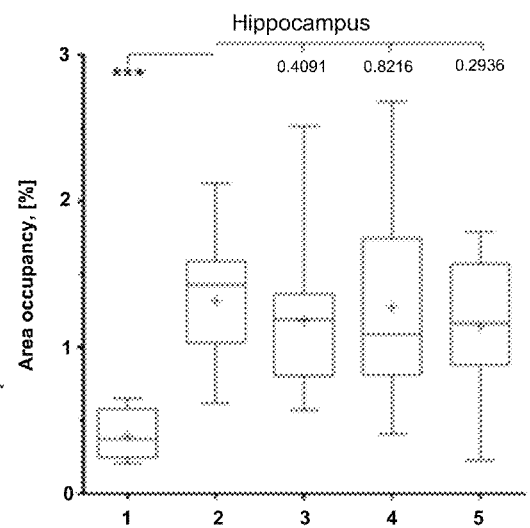

Treatment of TauPS2APP mice with either antibody 1 or antibody 2 resulted in a dose-dependent reduction in Tau (pS422) accumulation in brain homogenates (FIG. 7A-FIG. 7B). Using antibody 1 (VH35H5/VL31AS1), the reduction was statistically significant at 15 mg/kg. For antibody 2 (VH35H5/VL49G1) significantly less Tau(pS422) was accumulated in all dose groups. The overall level of tau was unchanged in all dose groups for both antibodies (FIG. 8A-FIG. 8B). Quantitative immunohistochemical analysis to detect Tau(pS422)-containing neurofibrillary aggrgates was performed on the brains of antibody 1 mice (FIG. 9A-FIG. 9B). Although there was no statistically significant lessening of tau pathology in any dose group, a trend to less pathology was observed with increasing dose. This was more apparent in the cortical region of the brains.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

---

The invention claimed is:

1. A humanized antibody that specifically binds to human Tau(pS422), wherein the antibody comprises
in the heavy chain variable domain the HVRs of SEQ ID NO: 08, 09 and 10, and
in the light chain variable domain
the HVRs of SEQ ID NO: 71, 73 and 15;
the HVRs of SEQ ID NO: 70, 72 and 15; or
the HVRs of SEQ ID NO: 12, 14 and 74.

2. The humanized antibody according to claim 1, comprising
a) a heavy chain variable domain of SEQ ID NO: 65 and a light chain variable domain of SEQ ID NO: 67;
b) a heavy chain variable domain of SEQ ID NO: 65 and a light chain variable domain of SEQ ID NO: 66; or
c) a heavy chain variable domain of SEQ ID NO: 65 and a light chain variable domain of SEQ ID NO: 68.

3. The humanized antibody according to claim 1, wherein the antibody is effector function silent.

4. The humanized antibody according to claim 1, wherein the antibody
i) specifically binds to a polypeptide that has the amino acid sequence of SEQ ID NO: 03, and/or
ii) does not bind to full length human Tau (SEQ ID NO: 01) at 1 μg/mL, and/or
iii) specifically binds to full length human Tau phosphorylated at the serine at position 422 (SEQ ID NO: 02), and/or
iv) specifically binds to aggregates of human Tau phosphorylated at the serine at position 422 (SEQ ID NO: 02).

5. The humanized antibody according to claim 1, wherein the antibody has an $EC_{50}$ value for
a) the human Tau(pS422) fragment that has the amino acid sequence of SEQ ID NO: 03 of 6 ng/mL or less, and/or
b) the full length human Tau(pS422) that has the amino acid sequence of SEQ ID NO: 02 of 4.5 ng/mL or less, and/or
c) aggregates of human Tau (pS422) that has the amino acid sequence of SEQ ID NO: 02 of 30 ng/mL or less, and/or
d) the human Tau that has the amino acid sequence of SEQ ID NO: 01 and that has the amino acid mutation S422A of 125 ng/mL or less.

6. The humanized antibody according to claim 1, wherein the antibody specifically binds to human Tau(pS422) (SEQ ID NO: 02) and does not bind to human Tau (SEQ ID NO: 01).

7. The humanized antibody according to claim 1, wherein the antibody is
a) a full length antibody of the human subclass IgG1;
b) a full length antibody of the human subclass IgG4;
c) a full length antibody of the human subclass IgG1 with the mutations L234A, L235A and P329G;
d) a full length antibody of the human subclass IgG4 with the mutations S228P, L235E and P329G;
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain; or
f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain.

8. A bispecific antibody comprising
i) a first binding site selected from
a) a heavy chain variable domain of SEQ ID NO: 65 and a light chain variable domain of SEQ ID NO: 66;
b) a heavy chain variable domain of SEQ ID NO: 65 and a light chain variable domain of SEQ ID NO: 67; or
c) a heavy chain variable domain of SEQ ID NO: 65 and a light chain variable domain of SEQ ID NO: 68, and
ii) a second binding site selected from
  a) a heavy chain variable domain of SEQ ID NO: 82 and a light chain variable domain of SEQ ID NO: 85;
  b) a heavy chain variable domain of SEQ ID NO: 83 and a light chain variable domain of SEQ ID NO: 85; or
  c) a heavy chain variable domain of SEQ ID NO: 84 and a light chain variable domain of SEQ ID NO: 85.

9. A pharmaceutical formulation comprising the antibody according to any one of claims 1 or 8 and optionally a pharmaceutically acceptable carrier.

10. A method of treating a subject suffering from Alzheimer's Disease, the method comprising administering to the subject an effective amount of an antibody according to any one of claim 1 or 8.

11. A method of treating a subject suffering from prodromal Alzheimer's Disease, the method comprising administering to the subject an effective amount of an antibody according to any one of claim 1 or 8.

12. A method for reducing Tau(pS422) induced neurodegeneration in a subject comprising administering to the subject an effective amount of an antibody according to claim 1 or 8.

13. A method of treatment comprising administering an antibody according to any one of claims 1 or 8 for treating Alzheimer's disease, for treating prodromal Alzheimer's disease, for treating mild Alzheimer's disease, for reducing Tau(pS422)-induced neurodegeneration, for maintaining cognition and function, for slowing the rate of cognitive and functional decline, or for slowing down the rate of neurofibrillary tangle accumulation.

* * * * *

SEQUENCE LISTING

```
<160> NUMBER OF SEQ ID NOS: 87

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

```
Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 441
<212> TYPE: PRT
<213> ORGANISM: Homo sapiens
<220> FEATURE:
<221> NAME/KEY: MISC_FEATURE
<222> LOCATION: (422)..(422)
<223> OTHER INFORMATION: X=phosphoserine

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60
```

```
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
             85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Xaa Pro Gln Leu Ala Thr Leu Ala Asp Glu Val
            420                 425                 430

Ser Ala Ser Leu Ala Lys Gln Gly Leu
            435                 440

<210> SEQ ID NO 3
<211> LENGTH: 15
<212> TYPE: PRT
<213> ORGANISM: Homo sapiens
<220> FEATURE:
<221> NAME/KEY: MISC_FEATURE
```

```
<222> LOCATION: (7)..(7)
<223> OTHER INFORMATION: X=phosphoserine

<400> SEQUENCE: 3

Ser Ile Asp Met Val Asp Xaa Pro Gln Leu Ala Thr Leu Ala Asp
1               5                   10                  15

<210> SEQ ID NO 4
<211> LENGTH: 12
<212> TYPE: PRT
<213> ORGANISM: Oryctolagus cuniculus

<400> SEQUENCE: 4

Gln Ser Ser Gln Ser Val Arg Thr Asn Lys Leu Ala
1               5                   10

<210> SEQ ID NO 5
<211> LENGTH: 7
<212> TYPE: PRT
<213> ORGANISM: Oryctolagus cuniculus

<400> SEQUENCE: 5

Ser Ala Ser Thr Leu Asp Phe
1               5

<210> SEQ ID NO 6
<211> LENGTH: 13
<212> TYPE: PRT
<213> ORGANISM: Oryctolagus cuniculus

<400> SEQUENCE: 6

Leu Gly Tyr Phe Asp Cys Ser Ile Ala Asp Cys Val Ala
1               5                   10

<210> SEQ ID NO 7
<211> LENGTH: 112
<212> TYPE: PRT
<213> ORGANISM: Oryctolagus cuniculus

<400> SEQUENCE: 7

Ala Gln Val Leu Thr Gln Thr Thr Ser Pro Val Ser Ala Ala Val Gly
1               5                   10                  15

Ser Thr Val Thr Ile Ser Cys Gln Ser Ser Gln Ser Val Arg Thr Asn
                20                  25                  30

Lys Leu Ala Trp Phe Gln Gln Lys Pro Gly Gln Pro Pro Lys Arg Leu
            35                  40                  45

Ile Tyr Ser Ala Ser Thr Leu Asp Phe Gly Val Pro Ser Arg Phe Ser
50                  55                  60

Ala Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Tyr Phe Asp Cys Ser
                85                  90                  95

Ile Ala Asp Cys Val Ala Phe Gly Gly Gly Thr Glu Val Val Val Lys
            100                 105                 110

<210> SEQ ID NO 8
<211> LENGTH: 5
<212> TYPE: PRT
<213> ORGANISM: Oryctolagus cuniculus

<400> SEQUENCE: 8

Ser Asn Ala Ile Asn
```

<210> SEQ ID NO 9
<211> LENGTH: 16
<212> TYPE: PRT
<213> ORGANISM: Oryctolagus cuniculus

<400> SEQUENCE: 9

Tyr Ile Ala Val Ser Gly Asn Thr Tyr Tyr Ala Ser Trp Ala Lys Gly
1               5                   10                  15

<210> SEQ ID NO 10
<211> LENGTH: 3
<212> TYPE: PRT
<213> ORGANISM: Oryctolagus cuniculus

<400> SEQUENCE: 10

Ser Asn Ile
1

<210> SEQ ID NO 11
<211> LENGTH: 108
<212> TYPE: PRT
<213> ORGANISM: Oryctolagus cuniculus

<400> SEQUENCE: 11

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
                20                  25                  30

Ile Asn Trp Val Arg Gln Ala Pro Gly Lys Gly Leu Glu Trp Ile Gly
            35                  40                  45

Tyr Ile Ala Val Ser Gly Asn Thr Tyr Tyr Ala Ser Trp Ala Lys Gly
        50                  55                  60

Arg Phe Thr Ile Ser Lys Ala Ser Thr Thr Val Asp Leu Lys Met Thr
65                  70                  75                  80

Ser Pro Thr Ala Glu Asp Thr Gly Thr Tyr Phe Cys Gly Lys Ser Asn
                85                  90                  95

Ile Trp Gly Pro Gly Thr Leu Val Thr Val Ser Leu
            100                 105

<210> SEQ ID NO 12
<211> LENGTH: 12
<212> TYPE: PRT
<213> ORGANISM: Artificial Sequence
<220> FEATURE:
<223> OTHER INFORMATION: humanized sequence

<400> SEQUENCE: 12

Arg Ser Ser Gln Ser Val Arg Thr Asn Lys Leu Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: humanized sequence

<400> SEQUENCE: 13

Arg Ser Ser Gln Ser Val Arg Thr Asn Arg Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: humanized sequence

<400> SEQUENCE: 14

Ser Ala Ser Thr Leu Asp Tyr
1               5

<210> SEQ ID NO 15
<211> LENGTH: 12
<212> TYPE: PRT
<213> ORGANISM: Artificial Sequence
<220> FEATURE:
<223> OTHER INFORMATION: humanized sequence

<400> SEQUENCE: 15

Leu Gly Tyr Phe Asp Ser Ser Ala Asp Ile Val Ala
1               5                   10

<210> SEQ ID NO 16
<211> LENGTH: 111
<212> TYPE: PRT
<213> ORGANISM: Artificial Sequence
<220> FEATURE:
<223> OTHER INFORMATION: humanized sequence

<400> SEQUENCE: 16

Ala Gln Val Met Thr Gln Ser Pro Ser Ser Leu Ser Ala Ser Val Gly
1               5                   10                  15

Asp Arg Val Thr Ile Thr Cys Arg Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: humanized sequence

<400> SEQUENCE: 17

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Tyr Gly Val Pro Ser Arg Phe Ser
    50                  55                  60

```
Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Tyr Phe Asp Ser Ser
                 85                  90                  95

Ala Asp Ile Val Ala Phe Gly Gly Gly Thr Lys Val Glu Ile Lys
            100                 105                 110

<210> SEQ ID NO 18
<211> LENGTH: 16
<212> TYPE: PRT
<213> ORGANISM: Artificial Sequence
<220> FEATURE:
<223> OTHER INFORMATION: humanized sequence

<400> SEQUENCE: 18

Tyr Ile Ala Val Ser Gly Asn Thr Tyr Tyr Ala Asp Ser Val Lys Gly
1               5                   10                  15

<210> SEQ ID NO 19
<211> LENGTH: 111
<212> TYPE: PRT
<213> ORGANISM: Artificial Sequence
<220> FEATURE:
<223> OTHER INFORMATION: humanized sequence

<400> SEQUENCE: 19

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: humanized sequence

<400> SEQUENCE: 20

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
```

```
                    85                  90                  95

Ile Ala Asp Ile Val Ala Phe Gly Gly Gly Thr Lys Val Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: humanizes sequence

<400> SEQUENCE: 21

Ala Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 22
<211> LENGTH: 7
<212> TYPE: PRT
<213> ORGANISM: Artificial Sequence
<220> FEATURE:
<223> OTHER INFORMATION: humanized sequence

<400> SEQUENCE: 22

Ser Ala Ser Thr Leu Gln Ser
1               5

<210> SEQ ID NO 23
<211> LENGTH: 7
<212> TYPE: PRT
<213> ORGANISM: Artificial Sequence
<220> FEATURE:
<223> OTHER INFORMATION: humanized sequence

<400> SEQUENCE: 23

Ser Ala Ser Thr Leu Glu Ser
1               5

<210> SEQ ID NO 24
<211> LENGTH: 13
<212> TYPE: PRT
<213> ORGANISM: Artificial Sequence
<220> FEATURE:
<223> OTHER INFORMATION: humanized sequence

<400> SEQUENCE: 24

Leu Gly Tyr Phe Asp Ser Ser Ile Ala Asp Ser Val Ala
1               5                   10

<210> SEQ ID NO 25
<211> LENGTH: 13
<212> TYPE: PRT
```

```
<213> ORGANISM: Artificial Sequence
<220> FEATURE:
<223> OTHER INFORMATION: humanized sequence

<400> SEQUENCE: 25

Leu Gly Tyr Phe Asp Ser Ser Ile Ala Asp Arg Val Ala
1               5                   10

<210> SEQ ID NO 26
<211> LENGTH: 13
<212> TYPE: PRT
<213> ORGANISM: Artificial Sequence
<220> FEATURE:
<223> OTHER INFORMATION: humanized sequence

<400> SEQUENCE: 26

Leu Gly Tyr Phe Asp Pro Ser Ile Ala Asp Pro Val Ala
1               5                   10

<210> SEQ ID NO 27
<211> LENGTH: 13
<212> TYPE: PRT
<213> ORGANISM: Artificial Sequence
<220> FEATURE:
<223> OTHER INFORMATION: humanized sequence

<400> SEQUENCE: 27

Leu Gly Tyr Phe Asp Ser Ser Ile Ala Asp Ile Val Ala
1               5                   10

<210> SEQ ID NO 28
<211> LENGTH: 12
<212> TYPE: PRT
<213> ORGANISM: Artificial Sequence
<220> FEATURE:
<223> OTHER INFORMATION: humanized sequence

<400> SEQUENCE: 28

Leu Gly Tyr Phe Asp Pro Ser Ala Asp Pro Ile Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: umanized sequence

<400> SEQUENCE: 29

Leu Gly Tyr Phe Asp Pro Ser Ala Asp Pro Val Ala
1               5                   10

<210> SEQ ID NO 30
<211> LENGTH: 12
<212> TYPE: PRT
<213> ORGANISM: Artificial Sequence
<220> FEATURE:
<223> OTHER INFORMATION: humanized sequence

<400> SEQUENCE: 30

Arg Ala Ser Gln Gly Val Arg Thr Asn Lys Leu Ala
1               5                   10

<210> SEQ ID NO 31
<211> LENGTH: 12
<212> TYPE: PRT
<213> ORGANISM: Artificial Sequence
```

```
<220> FEATURE:
<223> OTHER INFORMATION: humanized sequence

<400> SEQUENCE: 31

Arg Ala Ser Gln Ser Val Arg Thr Asn Lys Leu Ala
1               5                   10

<210> SEQ ID NO 32
<211> LENGTH: 112
<212> TYPE: PRT
<213> ORGANISM: Artificial Sequence
<220> FEATURE:
<223> OTHER INFORMATION: humanized sequence

<400> SEQUENCE: 32

Asp Ile Gln Met Thr Gln Ser Thr Ser Thr Leu Ser Ala Ser Val Gly
1               5                   10                  15

Asp Arg Val Thr Ile Thr Cys Gln Ser Ser Gln Ser Val Arg Thr Asn
            20                  25                  30

Lys Leu Ala Trp Phe Gln Gln Lys Pro Gly Lys Ala Pro Lys Arg Leu
        35                  40                  45

Ile Tyr Ser Ala Ser Thr Leu Asp Phe Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: humanized sequence

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Arg Thr Asn
            20                  25                  30

Lys Leu Ala Trp Tyr Gln Gln Lys Pro Gly Lys Ala Pro Lys Arg Leu
        35                  40                  45

Ile Tyr Ser Ala Ser Thr Leu Glu Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: humanized sequence

<400> SEQUENCE: 34
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110
```

<210> SEQ ID NO 35
<211> LENGTH: 112
<212> TYPE: PRT
<213> ORGANISM: Artificial Sequence
<220> FEATURE:
<223> OTHER INFORMATION: humanized sequence

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ser Val Ala Phe Gly Gly Gly Thr Lys Val Glu Ile Lys
            100                 105                 110
```

<210> SEQ ID NO 36
<211> LENGTH: 112
<212> TYPE: PRT
<213> ORGANISM: Artificial Sequence
<220> FEATURE:
<223> OTHER INFORMATION: humanized sequence

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
```

```
            85                  90                  95

Ile Ala Asp Arg Val Ala Phe Gly Gly Gly Thr Lys Val Glu Ile Lys
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: humanized sequence

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: humanized sequence

<400> SEQUENCE: 38

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: humanized sequence

<400> SEQUENCE: 39

Ala Ile Gln Met Thr Gln Ser Pro Ser Thr Leu Ser Ala Ser Val Gly
1               5                   10                  15
```

-continued

Asp Arg Val Thr Ile Thr Cys Arg Ser Ser Gln Ser Val Arg Thr Asn
            20                  25                  30

Arg Leu Ala Trp Phe Gln Gln Lys Pro Gly Lys Ala Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Tyr Phe Asp Pro Ser
                85                  90                  95

Ala Asp Pro Val Ala Phe Gly Gly Gly Thr Lys Val Glu Ile Lys
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: humanized sequence

<400> SEQUENCE: 40

Ala Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: humanized sequence

<400> SEQUENCE: 41

Ala Ile Gln Met Thr Gln Ser Thr Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys

-continued

<210> SEQ ID NO 42
<211> LENGTH: 112
<212> TYPE: PRT
<213> ORGANISM: Artificial Sequence
<220> FEATURE:
<223> OTHER INFORMATION: humanized sequence

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ile Ala Asp Pro Val Ala Phe Gly Gly Gly Thr Lys Val Glu Ile Lys
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: humanized sequence

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ala Asp Pro Val Ala Phe Gly Gly Gly Thr Lys Val Glu Ile Lys
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: humanized sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

```
Arg Leu Ala Trp Phe Gln Gln Lys Pro Gly Gln Pro Pro Lys Arg Leu
            35                  40                  45

Ile Tyr Ser Ala Ser Thr Leu Asp Phe Gly Val Pro Ser Arg Phe Ser
 50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ala Asp Pro Ile Ala Phe Gly Gly Gly Thr Lys Val Glu Ile Lys
            100                 105                 110

<210> SEQ ID NO 45
<211> LENGTH: 111
<212> TYPE: PRT
<213> ORGANISM: Artificial Sequence
<220> FEATURE:
<223> OTHER INFORMATION: humanized sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Lys Ala Pro Lys Arg Leu
        35                  40                  45

Ile Tyr Ser Ala Ser Thr Leu Asp Phe Gly Val Pro Ser Arg Phe Ser
 50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ala Asp Pro Ile Ala Phe Gly Gly Gly Thr Lys Val Glu Ile Lys
            100                 105                 110

<210> SEQ ID NO 46
<211> LENGTH: 110
<212> TYPE: PRT
<213> ORGANISM: Artificial Sequence
<220> FEATURE:
<223> OTHER INFORMATION: humanized sequence

<400> SEQUENCE: 46

Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
 50                  55                  60

Arg Phe Thr Ile Ser Arg Asp Asn Ser Lys Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
            100                 105                 110
```

-continued

```
<210> SEQ ID NO 47
<211> LENGTH: 110
<212> TYPE: PRT
<213> ORGANISM: Artificial Sequence
<220> FEATURE:
<223> OTHER INFORMATION: humanized sequence

<400> SEQUENCE: 47

Gln Ser Val Leu Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: humanized sequence

<400> SEQUENCE: 48

Gln Ser Val Leu Glu Ser Gly Gly Gly Leu Val Gln Pro Gly Gly Ser
1               5                   10                  15

Leu Arg Leu Ser Cys Ala Val Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 49
<211> LENGTH: 108
<212> TYPE: PRT
<213> ORGANISM: Artificial Sequence
<220> FEATURE:
<223> OTHER INFORMATION: humanized sequence

<400> SEQUENCE: 49

Gln Ser Val Leu Glu Ser Gly Gly Gly Leu Val Gln Pro Gly Gly Ser
1               5                   10                  15

Leu Arg Leu Ser Cys Ala Val Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45
```

```
Tyr Ile Ala Val Ser Gly Asn Thr Tyr Tyr Ala Ser Trp Ala Lys Gly
        50                  55                  60

Arg Phe Thr Ile Ser Arg Asp Ser Thr Thr Leu Tyr Leu Gln Met Asn
65                  70                  75                  80

Ser Leu Arg Ala Glu Asp Thr Ala Val Tyr Tyr Cys Gly Lys Ser Asn
                85                  90                  95

Ile Trp Gly Pro Gly Thr Leu Val Thr Val Ser Ser
                100                 105

<210> SEQ ID NO 50
<211> LENGTH: 110
<212> TYPE: PRT
<213> ORGANISM: Artificial Sequence
<220> FEATURE:
<223> OTHER INFORMATION: humanized sequence

<400> SEQUENCE: 50

Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
                20                  25                  30

Ile Asn Trp Val Arg Gln Ala Pro Gly Lys Gly Leu Glu Trp Val Gly
            35                  40                  45

Tyr Ile Ala Val Ser Gly Asn Thr Tyr Tyr Ala Ser Trp Ala Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: humanized sequence

<400> SEQUENCE: 51

Gln Ser Val Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
                20                  25                  30

Ile Asn Trp Val Arg Gln Ala Pro Gly Lys Gly Leu Glu Trp Val Gly
            35                  40                  45

Tyr Ile Ala Val Ser Gly Asn Thr Tyr Tyr Ala Ser Trp Ala Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 52
<211> LENGTH: 110
<212> TYPE: PRT
```

<213> ORGANISM: Artificial Sequence
<220> FEATURE:
<223> OTHER INFORMATION: humanized sequence

<400> SEQUENCE: 52

```
Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Asp Ser Val Lys Gly
    50                  55                  60

Arg Phe Thr Ile Ser Arg Asp Asn Ser Lys Asn Thr Leu Tyr Leu Gln
65              70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
            100                 105                 110
```

<210> SEQ ID NO 53
<211> LENGTH: 110
<212> TYPE: PRT
<213> ORGANISM: Artificial Sequence
<220> FEATURE:
<223> OTHER INFORMATION: humanized sequence

<400> SEQUENCE: 53

```
Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Asp Ser Val Lys Gly
    50                  55                  60

Arg Phe Thr Ile Ser Lys Asp Asn Ser Lys Asn Thr Leu Tyr Leu Gln
65              70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
            100                 105                 110
```

<210> SEQ ID NO 54
<211> LENGTH: 111
<212> TYPE: PRT
<213> ORGANISM: Artificial Sequence
<220> FEATURE:
<223> OTHER INFORMATION: humanized sequence

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Asp Ser Val Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: humanized sequence

<400> SEQUENCE: 55

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: humanized sequence

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: humanized sequence

<400> SEQUENCE: 57

```
Glu Val Gln Val Leu Glu Ser Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
            85                  90                  95

Lys Ser Asn Ile Trp Gly Gln Gly Thr Leu Val Thr Val Ser Ser
        100                 105                 110
```

<210> SEQ ID NO 58
<211> LENGTH: 330
<212> TYPE: PRT
<213> ORGANISM: Homo sapiens

<400> SEQUENCE: 58

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 107
<212> TYPE: PRT
<213> ORGANISM: Homo sapiens

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 60
<211> LENGTH: 106
<212> TYPE: PRT
<213> ORGANISM: Homo sapiens

<400> SEQUENCE: 60

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 61
<211> LENGTH: 37
<212> TYPE: DNA
<213> ORGANISM: Artificial Sequence
```

```
<220> FEATURE:
<223> OTHER INFORMATION: rbHCfinal.up

<400> SEQUENCE: 61
aagcttgcca ccatggagac tgggctgcgc tggcttc                                37

<210> SEQ ID NO 62
<211> LENGTH: 21
<212> TYPE: DNA
<213> ORGANISM: Artificial Sequence
<220> FEATURE:
<223> OTHER INFORMATION: rbHCfinal.do

<400> SEQUENCE: 62
ccattggtga gggtgcccga g                                                 21

<210> SEQ ID NO 63
<211> LENGTH: 34
<212> TYPE: DNA
<213> ORGANISM: Artificial Sequence
<220> FEATURE:
<223> OTHER INFORMATION: rbLCfinal.up

<400> SEQUENCE: 63
aagcttgcca ccatggacay gagggccccc actc                                   34

<210> SEQ ID NO 64
<211> LENGTH: 26
<212> TYPE: DNA
<213> ORGANISM: Artificial Sequence
<220> FEATURE:
<223> OTHER INFORMATION: rbLCfinal.do

<400> SEQUENCE: 64
cagagtrctg ctgaggttgt aggtac                                            26

<210> SEQ ID NO 65
<211> LENGTH: 111
<212> TYPE: PRT
<213> ORGANISM: Artificial Sequence
<220> FEATURE:
<223> OTHER INFORMATION: humanized sequence

<400> SEQUENCE: 65

Glu Val Gln Val Leu Glu Ser Gly Gly Gly Leu Val Gln Pro Gly Gly
1               5                   10                  15

Ser Leu Arg Leu Ser Cys Ala Val Ser Gly Ile Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 66
<211> LENGTH: 111
<212> TYPE: PRT
<213> ORGANISM: Artificial Sequence
```

```
<220> FEATURE:
<223> OTHER INFORMATION: humanized sequence

<400> SEQUENCE: 66

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Asn Asn
            20                  25                  30

Lys Leu Ala Trp Phe Gln Gln Lys Pro Gly Gln Pro Pro Lys Arg Leu
        35                  40                  45

Ile Tyr Ser Ala Ser Asp Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 67
<211> LENGTH: 111
<212> TYPE: PRT
<213> ORGANISM: Artificial Sequence
<220> FEATURE:
<223> OTHER INFORMATION: humanized sequence

<400> SEQUENCE: 67

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Ser Asn
            20                  25                  30

Lys Leu Ala Trp Phe Gln Gln Lys Pro Gly Gln Pro Pro Lys Arg Leu
        35                  40                  45

Ile Tyr Ser Ala Ser Asn Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 68
<211> LENGTH: 111
<212> TYPE: PRT
<213> ORGANISM: Artificial Sequence
<220> FEATURE:
<223> OTHER INFORMATION: humanized sequence

<400> SEQUENCE: 68

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60
```

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Pro
                85                  90                  95

Leu Asp Ile Val Ala Phe Gly Gly Gly Thr Lys Val Glu Ile Lys
            100                 105                 110

<210> SEQ ID NO 69
<211> LENGTH: 111
<212> TYPE: PRT
<213> ORGANISM: Artificial Sequence
<220> FEATURE:
<223> OTHER INFORMATION: humanized sequence

<400> SEQUENCE: 69

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Ala Gly Tyr Phe Asp Pro His
                85                  90                  95

Gln Asp Val Val Ala Phe Gly Gly Gly Thr Lys Val Glu Ile Lys
            100                 105                 110

<210> SEQ ID NO 70
<211> LENGTH: 12
<212> TYPE: PRT
<213> ORGANISM: Artificial Sequence
<220> FEATURE:
<223> OTHER INFORMATION: HVR-L1

<400> SEQUENCE: 70

Arg Ser Ser Gln Ser Val Arg Asn Asn Lys Leu Ala
1               5                   10

<210> SEQ ID NO 71
<211> LENGTH: 12
<212> TYPE: PRT
<213> ORGANISM: Artificial Sequence
<220> FEATURE:
<223> OTHER INFORMATION: HVR-L1

<400> SEQUENCE: 71

Arg Ser Ser Gln Ser Val Arg Ser Asn Lys Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: HVR-L2

<400> SEQUENCE: 72

Ser Ala Ser Asp Leu Asp Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: HVR-L2

<400> SEQUENCE: 73

Ser Ala Ser Asn Leu Asp Tyr
1               5

<210> SEQ ID NO 74
<211> LENGTH: 12
<212> TYPE: PRT
<213> ORGANISM: Artificial Sequence
<220> FEATURE:
<223> OTHER INFORMATION: HVR-L3

<400> SEQUENCE: 74

Leu Gly Tyr Phe Asp Ser Pro Leu Asp Ile Val Ala
1               5                   10

<210> SEQ ID NO 75
<211> LENGTH: 12
<212> TYPE: PRT
<213> ORGANISM: Artificial Sequence
<220> FEATURE:
<223> OTHER INFORMATION: HVR-L3

<400> SEQUENCE: 75

Ala Gly Tyr Phe Asp Pro His Gln Asp Val Val Ala
1               5                   10

<210> SEQ ID NO 76
<211> LENGTH: 111
<212> TYPE: PRT
<213> ORGANISM: Artificial Sequence
<220> FEATURE:
<223> OTHER INFORMATION: heavy chain variable domain

<400> SEQUENCE: 76

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Asn Ser
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 77
<211> LENGTH: 5
<212> TYPE: PRT
<213> ORGANISM: Artificial Sequence
<220> FEATURE:
<223> OTHER INFORMATION: HVR-H1

<400> SEQUENCE: 77

```
Asn Ser Ala Ile Asn
1               5

<210> SEQ ID NO 78
<211> LENGTH: 111
<212> TYPE: PRT
<213> ORGANISM: Artificial Sequence
<220> FEATURE:
<223> OTHER INFORMATION: VL35G4

<400> SEQUENCE: 78

Ala Gln Val Met Thr Gln Ser Pro Ser Leu Ser Ala Ser Val Gly
1               5                   10                  15

Asp Arg Val Thr Ile Thr Cys Arg Ser Gln Ser Val Arg Thr Asn
                20                  25                  30

Lys Leu Ala Trp Phe Gln Gln Lys Pro Gly Gln Pro Lys Arg Leu
            35                  40                  45

Ile Tyr Ser Ala Ser Thr Leu Asp Phe Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Ala Gly Tyr Phe Glu Ala Pro
                85                  90                  95

Ala Asp Ile Val Ala Phe Gly Gly Gly Thr Lys Val Glu Ile Lys
            100                 105                 110

<210> SEQ ID NO 79
<211> LENGTH: 12
<212> TYPE: PRT
<213> ORGANISM: Artificial Sequence
<220> FEATURE:
<223> OTHER INFORMATION: HVR-L3

<400> SEQUENCE: 79

Ala Gly Tyr Phe Glu Ala Pro Ala Asp Ile Val Ala
1               5                   10

<210> SEQ ID NO 80
<211> LENGTH: 111
<212> TYPE: PRT
<213> ORGANISM: Artificial Sequence
<220> FEATURE:
<223> OTHER INFORMATION: VL145B12

<400> SEQUENCE: 80

Ala Gln Val Met Thr Gln Ser Pro Ser Leu Ser Ala Ser Val Gly
1               5                   10                  15

Asp Arg Val Thr Ile Thr Cys Arg Ser Ser Gln Ser Val Arg Ser Asn
                20                  25                  30

Lys Leu Ala Trp Phe Gln Gln Lys Pro Gly Gln Pro Lys Arg Leu
            35                  40                  45

Ile Tyr Ala Ala Ser Asn Leu Asp Phe Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110
```

<210> SEQ ID NO 81
<211> LENGTH: 7
<212> TYPE: PRT
<213> ORGANISM: Artificial Sequence
<220> FEATURE:
<223> OTHER INFORMATION: HVR-L2

<400> SEQUENCE: 81

Ala Ala Ser Asn Leu Asp Phe
1               5

<210> SEQ ID NO 82
<211> LENGTH: 124
<212> TYPE: PRT
<213> ORGANISM: Artificial Sequence
<220> FEATURE:
<223> OTHER INFORMATION: 299-009 VH humanization variant_DANG

<400> SEQUENCE: 82

Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Asn Gly Phe Asp
            100                 105                 110

Pro Trp Gly Gln Gly Thr Leu Val Thr Val Ser Ser
        115                 120

<210> SEQ ID NO 83
<211> LENGTH: 124
<212> TYPE: PRT
<213> ORGANISM: Artificial Sequence
<220> FEATURE:
<223> OTHER INFORMATION: 299-009 VH humanization variant_DASG

<400> SEQUENCE: 83

Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Ser Gly Phe Asp
            100                 105                 110

Pro Trp Gly Gln Gly Thr Leu Val Thr Val Ser Ser

<210> SEQ ID NO 84
<211> LENGTH: 124
<212> TYPE: PRT
<213> ORGANISM: Artificial Sequence
<220> FEATURE:
<223> OTHER INFORMATION: 299-009 VH humanization variant_DAQG

<400> SEQUENCE: 84

```
Gln Gln Leu Leu Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Ala
            20                  25                  30

Met Ser Trp Val Arg Gln Ala Pro Gly Lys Gly Leu Glu Trp Val Gly
        35                  40                  45

Tyr Ile Trp Ser Gly Gly Ser Thr Asp Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Arg Tyr Gly Thr Ser Tyr Pro Asp Tyr Gly Asp Ala Gln Gly Phe Asp
            100                 105                 110

Pro Trp Gly Gln Gly Thr Leu Val Thr Val Ser Ser
        115                 120
```

<210> SEQ ID NO 85
<211> LENGTH: 110
<212> TYPE: PRT
<213> ORGANISM: Artificial Sequence
<220> FEATURE:
<223> OTHER INFORMATION: 299-009 VL humanization variant_NYA

<400> SEQUENCE: 85

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ala Ser Ser Asn
                85                  90                  95

Val Asp Asn Thr Phe Gly Gly Gly Thr Lys Val Glu Ile Lys
            100                 105                 110
```

<210> SEQ ID NO 86
<211> LENGTH: 111
<212> TYPE: PRT
<213> ORGANISM: Artificial Sequence
<220> FEATURE:
<223> OTHER INFORMATION: VL4G1

<400> SEQUENCE: 86

```
Ala Gln Val Met Thr Gln Ser Pro Ser Ser Leu Ser Ala Ser Val Gly
1               5                   10                  15
```

```
Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Tyr Phe Asp Ser Pro
                 85                  90                  95

Ala Asp Ile Val Ala Phe Gly Gly Gly Thr Lys Val Glu Ile Lys
             100                 105                 110

<210> SEQ ID NO 87
<211> LENGTH: 12
<212> TYPE: PRT
<213> ORGANISM: Artificial Sequence
<220> FEATURE:
<223> OTHER INFORMATION: VL4G1-HVR-L3

<400> SEQUENCE: 87

Leu Gly Tyr Phe Asp Ser Pro Ala Asp Ile Val Ala
 1               5                  10
```